US008321019B2

(12) United States Patent
Esch et al.

(10) Patent No.: US 8,321,019 B2
(45) Date of Patent: Nov. 27, 2012

(54) APPARATUS AND METHOD FOR ENSURING SAFE OPERATION OF A THERMAL TREATMENT CATHETER

(75) Inventors: Brady David Esch, San Jose, CA (US); Brian Eugene Farley, Los Altos, CA (US)

(73) Assignee: Covidien LP, Mansfield, MA (US)

( * ) Notice: Subject to any disclaimer, the term of this patent is extended or adjusted under 35 U.S.C. 154(b) by 1392 days.

(21) Appl. No.: 11/490,638

(22) Filed: Jul. 21, 2006

(65) Prior Publication Data

US 2007/0049999 A1 Mar. 1, 2007

Related U.S. Application Data

(60) Provisional application No. 60/780,948, filed on Mar. 9, 2006, provisional application No. 60/701,303, filed on Jul. 21, 2005.

(51) Int. Cl.
*A61B 18/08* (2006.01)
(52) U.S. Cl. ............... 607/27; 606/31; 607/96; 607/113
(58) Field of Classification Search ............... 606/32–50
See application file for complete search history.

(56) References Cited

U.S. PATENT DOCUMENTS

| | | |
|---|---|---|
| 3,301,258 A | 1/1967 | Werner et al. |
| 3,605,750 A | 9/1971 | Sheridan et al. |
| 4,154,246 A | 5/1979 | LeVeen |
| 4,564,011 A | 1/1986 | Goldman |
| 4,654,024 A | 3/1987 | Crittenden et al. |
| 4,672,962 A | 6/1987 | Hershenson |
| 4,709,698 A | 12/1987 | Johnston et al. |
| 4,748,979 A | 6/1988 | Hershenson |
| 4,765,331 A | 8/1988 | Petruzzi et al. |
| 4,907,589 A | 3/1990 | Cosman |
| 4,945,912 A | 8/1990 | Langberg |

(Continued)

FOREIGN PATENT DOCUMENTS

EP 1350481 10/2003

(Continued)

OTHER PUBLICATIONS

Introducing Closure ® Catheters with Graduation Marks. The depicted catheter, with the instructions for use enclosed, was on sale in the United States more than one year before the earliest effective priority date for the present application.

(Continued)

*Primary Examiner* — Michael Peffley
*Assistant Examiner* — Ronald Hupczey, Jr.
(74) *Attorney, Agent, or Firm* — Mark J. Kertz, Esq.

(57) ABSTRACT

A working end of a catheter includes at least one therapeutic element, such as a resistive heating element, usable to deliver energy for ligating, or reducing the diameter of, a hollow anatomical structure. In certain examples, the catheter includes a lumen to accommodate a guide wire or to allow fluid delivery. In certain embodiments, a balloon is inflated to place resistive element(s) into apposition with a hollow anatomical structure and to occlude the structure. Indexing devices and methods are also disclosed for successively treating portions of the hollow anatomical structure. In certain examples, marks along the catheter shaft provide visual verification to the physician of the relative position of the therapeutic element of the catheter. Embodiments of indexing devices may include pairs of rings and/or hinged arms that move a catheter a desired indexed position between successive treatments.

29 Claims, 47 Drawing Sheets

U.S. PATENT DOCUMENTS

| | | |
|---|---|---|
| 4,951,686 A | 8/1990 | Herlitze |
| 4,989,601 A | 2/1991 | Marchosky et al. |
| 5,022,399 A | 6/1991 | Biegeleisen |
| 5,042,486 A | 8/1991 | Pfeiler et al. |
| 5,047,025 A | 9/1991 | Taylor et al. |
| 5,057,106 A | 10/1991 | Kasevich et al. |
| 5,078,736 A | 1/1992 | Behl |
| 5,100,388 A | 3/1992 | Behl et al. |
| 5,188,602 A | 2/1993 | Nichols |
| 5,257,634 A | 11/1993 | Kroll |
| 5,263,963 A | 11/1993 | Garrison et al. |
| 5,370,678 A | 12/1994 | Edwards et al. |
| 5,405,346 A | 4/1995 | Grundy et al. |
| 5,425,367 A | 6/1995 | Shapiro et al. |
| 5,433,708 A | 7/1995 | Nichols et al. |
| 5,437,664 A | 8/1995 | Cohen et al. |
| 5,441,516 A | 8/1995 | Wang et al. |
| 5,470,309 A | 11/1995 | Edwards et al. |
| 5,472,441 A | 12/1995 | Edwards et al. |
| 5,474,080 A | 12/1995 | Hughes |
| 5,505,730 A | 4/1996 | Edwards |
| 5,540,680 A | 7/1996 | Guglielmi et al. |
| 5,542,928 A | 8/1996 | Evans et al. |
| 5,556,396 A | 9/1996 | Cohen et al. |
| 5,582,609 A | 12/1996 | Swanson et al. |
| 5,584,830 A | 12/1996 | Ladd et al. |
| 5,588,432 A | 12/1996 | Crowley |
| 5,607,422 A | 3/1997 | Smeets et al. |
| 5,611,778 A | 3/1997 | Brinon |
| 5,643,257 A | 7/1997 | Cohen et al. |
| 5,709,224 A | 1/1998 | Behl et al. |
| 5,722,975 A | 3/1998 | Edwards et al. |
| 5,743,903 A | 4/1998 | Stern et al. |
| 5,746,224 A * | 5/1998 | Edwards ................. 128/898 |
| 5,752,951 A | 5/1998 | Yanik |
| 5,755,715 A | 5/1998 | Stern et al. |
| 5,775,338 A | 7/1998 | Hastings |
| 5,779,698 A | 7/1998 | Clayman et al. |
| 5,797,905 A | 8/1998 | Fleischman et al. |
| 5,807,269 A | 9/1998 | Quinn et al. |
| 5,810,802 A | 9/1998 | Panescu et al. |
| 5,827,268 A | 10/1998 | Laufer |
| 5,837,003 A | 11/1998 | Ginsburg |
| 5,843,152 A | 12/1998 | Tu et al. |
| 5,851,210 A | 12/1998 | Torossian |
| 5,860,923 A | 1/1999 | Lenker et al. |
| 5,871,523 A | 2/1999 | Fleischman et al. |
| 5,879,347 A | 3/1999 | Saadat |
| 5,885,278 A | 3/1999 | Fleischman |
| 5,906,614 A | 5/1999 | Stern et al. |
| 5,919,187 A | 7/1999 | Guglielmi et al. |
| 5,931,835 A * | 8/1999 | Mackey ................. 606/34 |
| 5,954,717 A | 9/1999 | Behl et al. |
| 5,976,131 A | 11/1999 | Guglielmi et al. |
| 6,010,500 A | 1/2000 | Sherman et al. |
| 6,011,995 A | 1/2000 | Guglielmi et al. |
| 6,019,757 A | 2/2000 | Scheldrup |
| 6,030,382 A | 2/2000 | Fleischman et al. |
| 6,033,383 A | 3/2000 | Ginsburg |
| 6,033,397 A | 3/2000 | Laufer et al. |
| 6,033,398 A | 3/2000 | Farley et al. |
| 6,036,687 A | 3/2000 | Laufer et al. |
| 6,039,721 A | 3/2000 | Johnson et al. |
| 6,041,260 A | 3/2000 | Stern et al. |
| 6,042,590 A | 3/2000 | Sporri et al. |
| 6,090,104 A | 7/2000 | Webster, Jr. |
| 6,112,123 A | 8/2000 | Kelleher et al. |
| 6,122,549 A | 9/2000 | Sharkey et al. |
| 6,126,654 A | 10/2000 | Giba et al. |
| 6,176,856 B1 | 1/2001 | Jandak et al. |
| 6,183,466 B1 | 2/2001 | Wong et al. |
| 6,183,468 B1 * | 2/2001 | Swanson et al. ............. 606/40 |
| 6,200,333 B1 | 3/2001 | Laufer |
| 6,217,573 B1 * | 4/2001 | Webster ................. 606/41 |
| 6,228,080 B1 | 5/2001 | Gines |
| 6,231,572 B1 | 5/2001 | Hart et al. |
| 6,235,024 B1 | 5/2001 | Tu |
| 6,258,084 B1 | 7/2001 | Goldman et al. |
| 6,290,715 B1 | 9/2001 | Sharkey et al. |
| 6,302,904 B1 | 10/2001 | Wallstén et al. |
| 6,304,776 B1 | 10/2001 | Muntermann |
| 6,306,134 B1 | 10/2001 | Goble et al. |
| 6,322,559 B1 | 11/2001 | Daulton et al. |
| 6,322,584 B2 | 11/2001 | Ingle et al. |
| 6,327,505 B1 | 12/2001 | Medhkour et al. |
| 6,346,102 B1 | 2/2002 | Harrington et al. |
| 6,355,033 B1 | 3/2002 | Moorman et al. |
| 6,391,024 B1 * | 5/2002 | Sun et al. ................. 606/34 |
| 6,398,777 B1 | 6/2002 | Navarro et al. |
| 6,401,719 B1 | 6/2002 | Farley et al. |
| 6,408,199 B1 | 6/2002 | Goldin |
| 6,416,511 B1 | 7/2002 | Lesh et al. |
| 6,478,793 B1 | 11/2002 | Cosman et al. |
| 6,485,430 B1 | 11/2002 | Quinn et al. |
| 6,490,488 B1 | 12/2002 | Rudie et al. |
| 6,493,589 B1 | 12/2002 | Medhkour et al. |
| 6,494,880 B1 | 12/2002 | Swanson et al. |
| 6,508,815 B1 | 1/2003 | Strul et al. |
| 6,517,534 B1 | 2/2003 | McGovern et al. |
| 6,539,265 B2 | 3/2003 | Medhkour et al. |
| 6,547,810 B1 | 4/2003 | Sharkey et al. |
| 6,551,310 B1 | 4/2003 | Ganz et al. |
| 6,554,827 B2 | 4/2003 | Chandrasekaran et al. |
| 6,565,557 B1 | 5/2003 | Sporri et al. |
| 6,587,731 B1 | 7/2003 | Ingle et al. |
| 6,605,084 B2 | 8/2003 | Acker et al. |
| 6,613,002 B1 | 9/2003 | Clark et al. |
| 6,620,159 B2 | 9/2003 | Hegde |
| 6,635,076 B1 | 10/2003 | Ginsburg |
| 6,640,138 B1 | 10/2003 | Schaefermeyer |
| 6,669,692 B1 | 12/2003 | Nelson et al. |
| 6,679,904 B2 | 1/2004 | Gleeson et al. |
| 6,689,127 B1 | 2/2004 | Gough et al. |
| 6,699,268 B2 | 3/2004 | Kordis et al. |
| 6,712,815 B2 | 3/2004 | Sampson et al. |
| 6,716,192 B1 | 4/2004 | Orosz, Jr. |
| 6,723,094 B1 | 4/2004 | Desinger |
| 6,740,084 B2 | 5/2004 | Ryan |
| 6,745,080 B2 | 6/2004 | Koblish |
| 6,752,803 B2 | 6/2004 | Goldman et al. |
| 6,752,804 B2 | 6/2004 | Simpson et al. |
| 6,796,981 B2 | 9/2004 | Wham et al. |
| 6,805,129 B1 | 10/2004 | Pless et al. |
| 6,905,494 B2 | 6/2005 | Yon et al. |
| 6,964,652 B2 | 11/2005 | Guiles et al. |
| 6,964,661 B2 | 11/2005 | Rioux et al. |
| 6,981,971 B2 | 1/2006 | Caldera et al. |
| 6,986,766 B2 | 1/2006 | Caldera et al. |
| 7,179,255 B2 | 2/2007 | Lettice et al. |
| 7,276,061 B2 | 10/2007 | Schaer et al. |
| 7,364,577 B2 | 4/2008 | Wham et al. |
| 7,396,355 B2 | 7/2008 | Goldman et al. |
| 7,458,967 B2 | 12/2008 | Appling et al. |
| 7,517,349 B2 | 4/2009 | Truckai et al. |
| 7,524,316 B2 | 4/2009 | Hennings et al. |
| 7,593,778 B2 | 9/2009 | Chandran et al. |
| 7,625,352 B1 | 12/2009 | Ashby et al. |
| 7,625,372 B2 | 12/2009 | Esch et al. |
| 7,655,033 B2 | 2/2010 | Fearnot et al. |
| 7,828,793 B2 | 11/2010 | Thompson et al. |
| 7,837,677 B2 | 11/2010 | Thompson et al. |
| 7,837,678 B2 | 11/2010 | Thompson et al. |
| 7,842,076 B2 | 11/2010 | Zikorus et al. |
| 2001/0012956 A1 | 8/2001 | Behl et al. |
| 2001/0041888 A1 | 11/2001 | Goldman et al. |
| 2002/0165529 A1 | 11/2002 | Danek |
| 2002/0177846 A1 | 11/2002 | Mulier et al. |
| 2003/0028180 A1 | 2/2003 | Franco |
| 2003/0078569 A1 | 4/2003 | Caldera |
| 2003/0191460 A1 | 10/2003 | Hobbs et al. |
| 2003/0212395 A1 | 11/2003 | Woloszko et al. |
| 2004/0010289 A1 | 1/2004 | Biggs et al. |
| 2004/0059397 A1 | 3/2004 | Sinofsky et al. |
| 2004/0068190 A1 | 4/2004 | Cespedes |
| 2004/0087936 A1 | 5/2004 | Stern et al. |
| 2004/0111136 A1 | 6/2004 | Sharkey et al. |
| 2004/0122420 A1 | 6/2004 | Amoh |

| | | | | | | |
|---|---|---|---|---|---|---|
| 2004/0127963 | A1 | 7/2004 | Uchida et al. | WO | WO 2004/093693 A1 | 11/2004 |
| 2004/0138519 | A1 | 7/2004 | Viole et al. | WO | WO 2005034783 A | 4/2005 |
| 2004/0153060 | A1 | 8/2004 | Lindenbaum et al. | WO | WO 2006/054170 | 5/2006 |
| 2004/0199151 | A1 | 10/2004 | Neuberger | WO | WO 2006069313 A | 6/2006 |
| 2004/0199156 | A1 | 10/2004 | Rioux et al. | | | |
| 2005/0054954 | A1 | 3/2005 | Lidgren et al. | | | |
| 2005/0085804 | A1 | 4/2005 | McGaffigan | | | |
| 2005/0192654 | A1 | 9/2005 | Chanduszko et al. | | | |
| 2005/0277918 | A1 | 12/2005 | Shah et al. | | | |
| 2006/0030849 | A1 | 2/2006 | Mirizzi et al. | | | |
| 2006/0079870 | A1 | 4/2006 | Barry | | | |
| 2006/0084968 | A1 | 4/2006 | Truckai et al. | | | |
| 2006/0142824 | A1 | 6/2006 | Zikorus et al. | | | |
| 2007/0016272 | A1 | 1/2007 | Thompson | | | |
| 2007/0049918 | A1 | 3/2007 | Van Der Weide et al. | | | |
| 2007/0050000 | A1 | 3/2007 | Esch et al. | | | |
| 2007/0055327 | A1 | 3/2007 | Esch | | | |
| 2007/0078569 | A1 | 4/2007 | Schox et al. | | | |
| 2007/0135791 | A1 | 6/2007 | Slater et al. | | | |
| 2007/0156126 | A1 | 7/2007 | Flaherty | | | |
| 2007/0185554 | A1 | 8/2007 | Appling et al. | | | |
| 2007/0191825 | A1 | 8/2007 | Cronin et al. | | | |
| 2008/0015664 | A1 | 1/2008 | Podhajsky | | | |
| 2008/0033425 | A1 | 2/2008 | Davis et al. | | | |
| 2008/0051776 | A1 | 2/2008 | Bliweis et al. | | | |
| 2008/0097424 | A1 | 4/2008 | Wizeman et al. | | | |
| 2008/0097557 | A1 | 4/2008 | Eggers et al. | | | |
| 2008/0167643 | A1 | 7/2008 | Mizrahi et al. | | | |
| 2008/0188843 | A1 | 8/2008 | Appling et al. | | | |
| 2009/0149932 | A1 | 6/2009 | Thompson | | | |
| 2009/0157066 | A1 | 6/2009 | Satake | | | |
| 2009/0192544 | A1 | 7/2009 | Merchant, Jr. | | | |
| 2010/0036465 | A1 | 2/2010 | Glukhovsky et al. | | | |
| 2010/0082040 | A1 | 4/2010 | Sahni | | | |
| 2010/0106150 | A1 | 4/2010 | Thompson | | | |
| 2010/0106151 | A1 | 4/2010 | Longo et al. | | | |
| 2010/0114085 | A1 | 5/2010 | Thompson | | | |
| 2010/0145327 | A1 | 6/2010 | Thompson | | | |
| 2010/0145424 | A1 | 6/2010 | Podhajsky et al. | | | |
| 2010/0204697 | A1 | 8/2010 | Dumbauld et al. | | | |
| 2011/0034922 | A1 | 2/2011 | Thompson | | | |
| 2011/0046617 | A1 | 2/2011 | Thompson | | | |

FOREIGN PATENT DOCUMENTS

| | | |
|---|---|---|
| EP | 1527748 A | 5/2005 |
| GB | 2333964 | 8/1999 |
| WO | WO 9308755 | 5/1993 |
| WO | WO 9308755 A | 5/1993 |
| WO | WO 95/10322 | 4/1995 |
| WO | WO 9855046 A | 12/1998 |
| WO | WO 9911185 A | 3/1999 |

OTHER PUBLICATIONS

U.S. Appl. No. 12/686,323, filed Jan. 12, 2010, Thompson et al.
U.S. Appl. No. 12/691,703, filed Jan. 21, 2010, Thompson et al.
U.S. Appl. No. 11/491,065, filed Jul. 21, 2006, Esch.
U.S. Appl. No. 11/491,067, filed Jul. 21, 2006, Esch.
U.S. Appl. No. 11/491,346, filed Jul. 21, 2006, Farley.
U.S. Appl. No. 11/491,348, filed Jul. 21, 2006, Thompson.
U.S. Appl. No. 11/491,424, filed Jul. 21, 2006, Esch.
Avitall et al, "The Effects of Electrode-Tissue Contact on Radiofrequency Lesion Generation", Dec. 1997, PACE, vol. 20, 2899-2910.
Cao et al, "Using Electrical Impedance to Predict Catheter-Endocardial Contact During RF Cardiac Ablation", Mar. 2002, IEEE Transactions on Biomedical Engineering, vol. 49 No. 3, 247-252.
Zheng et al, "Electrode Impedance: An Indicator of Electrode-Tissue Contact and Lesion Dimensions During Linear Ablation", 2000, Journal of Interventional Cardiac Electrophysiology, 645-654.
International Search Report for PCT Application No. PCT/US2006/028454 mailed Mar. 28, 2007.
Becker, Catheter for Endoluminal Bipolar Electrocoagulation, Radiology, p. 561, vol. 170. No. 2, 1989.
Brunelle, A Bipolar Electrode for Vascular Electrocoagulation with Alternating Current, Radiology, 137:239-240, Oct. 1990.
Clegg, Microwave Soft Tissue Ablation, Thermal Treatment of Tissue: Energy Delivery and Assessment III, p. 56, Proceedings of SPIE, vol. 5698, 2005.
Crockett et al., Preliminary Experience with an Endovascular Catheter for Electrocoagulation of Peripheral Veins, p. 19-22, JVT 1996.
Expert Review, Progress in the development of neural prosthetic devices, Future Drugs LTD., 2007.
Mordon et al., Mathematical modeling of endovenous laser treatment (ELT), Biomed Eng Online, vol. 5, Published online Apr. 25, 2006.
Perkowski, Endovenous Laser Ablation of the Saphenous Vein for Treatment of Venous Insufficiency and Varicose Veins: Early Results From a Large Single-Center Experience, p. 132, Journal Endovascular Therapy, 2004.
Perrin, Endoluminal treatment of lower limb varicose veins by endovenous laser and radiofrequency techniques, Phlebology, p. 170-178, vol. 19 No. 4, 2004.
U.S. Appl. No. 13/151,950, filed Jun. 2, 2011, Russell Blake Thompson.

* cited by examiner

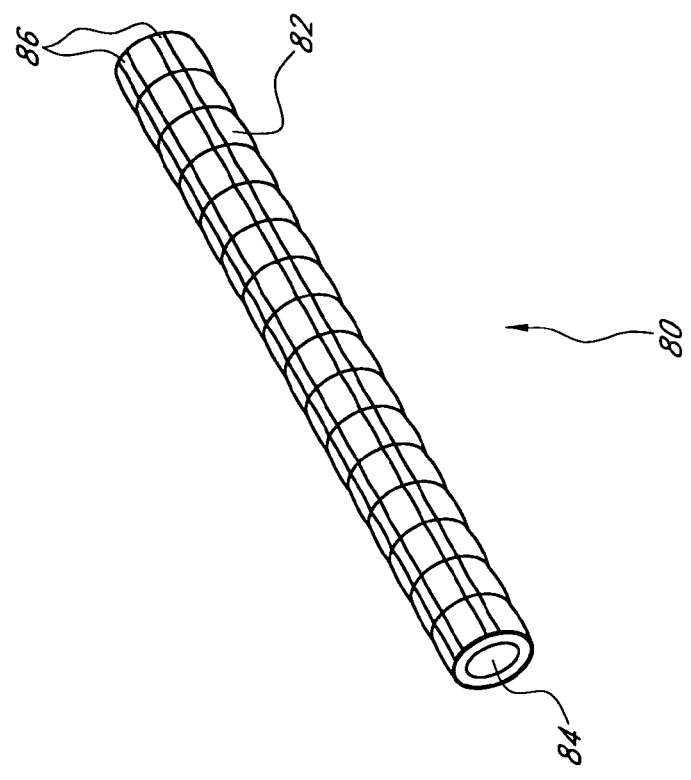
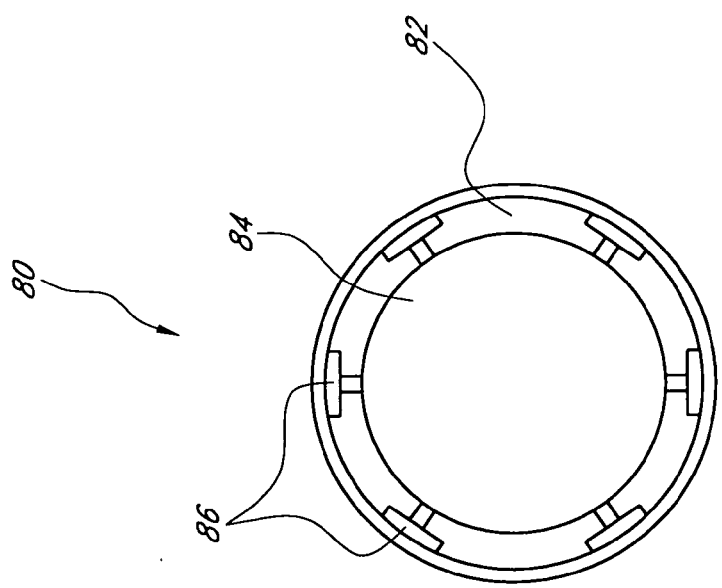
FIG. 7C

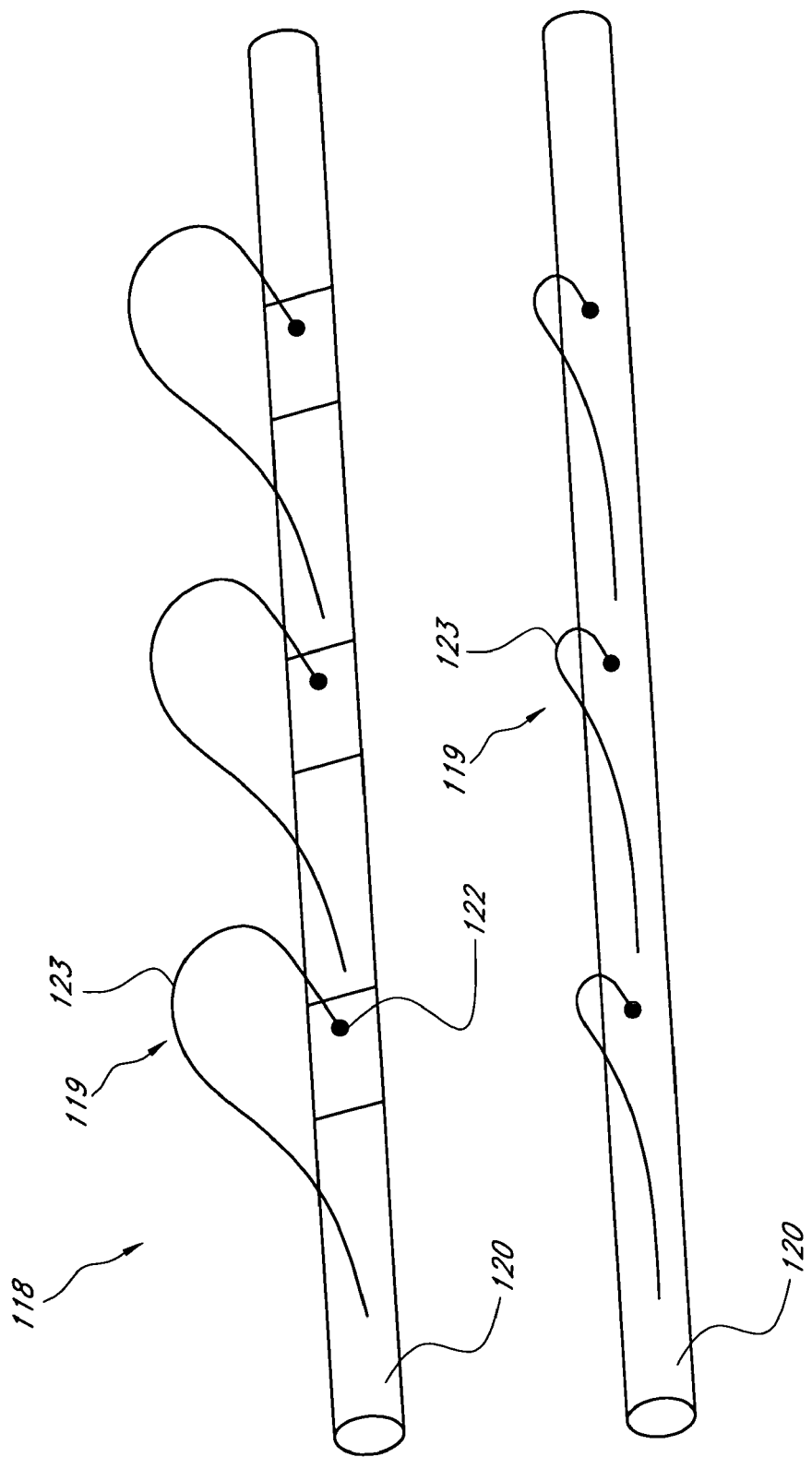

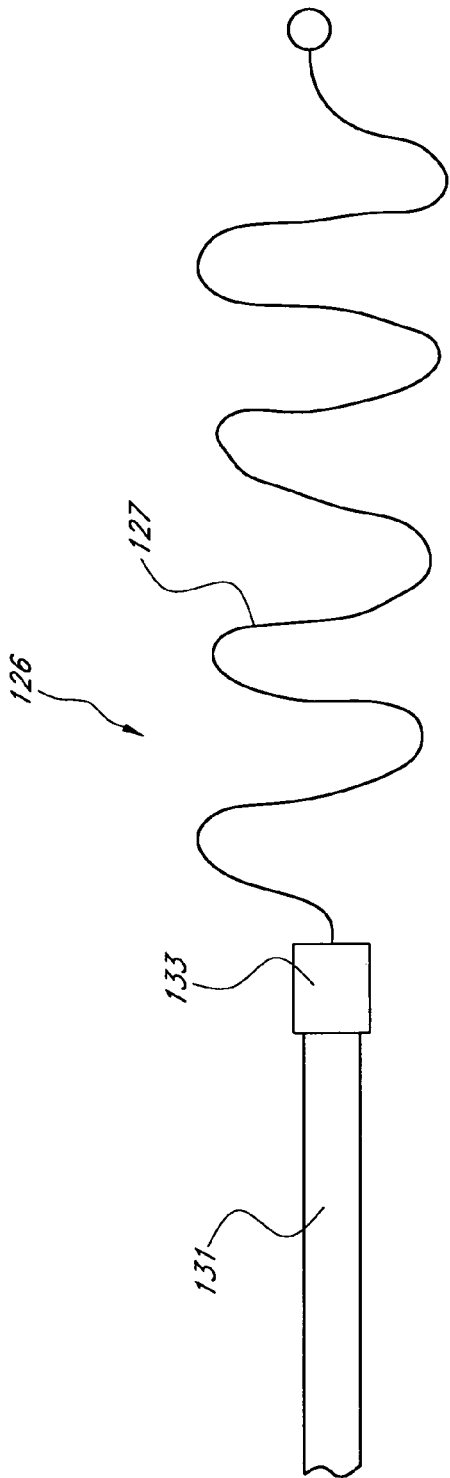
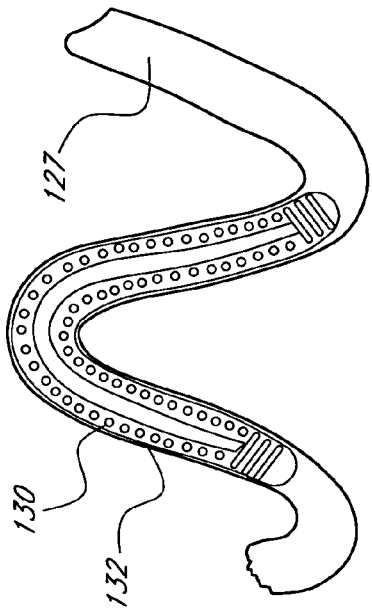
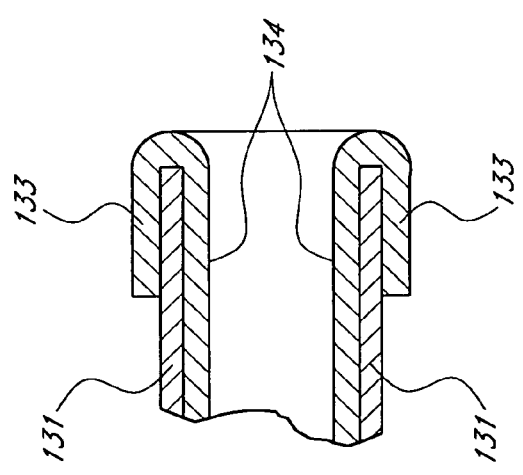
FIG. 10B
FIG. 10D
FIG. 10C

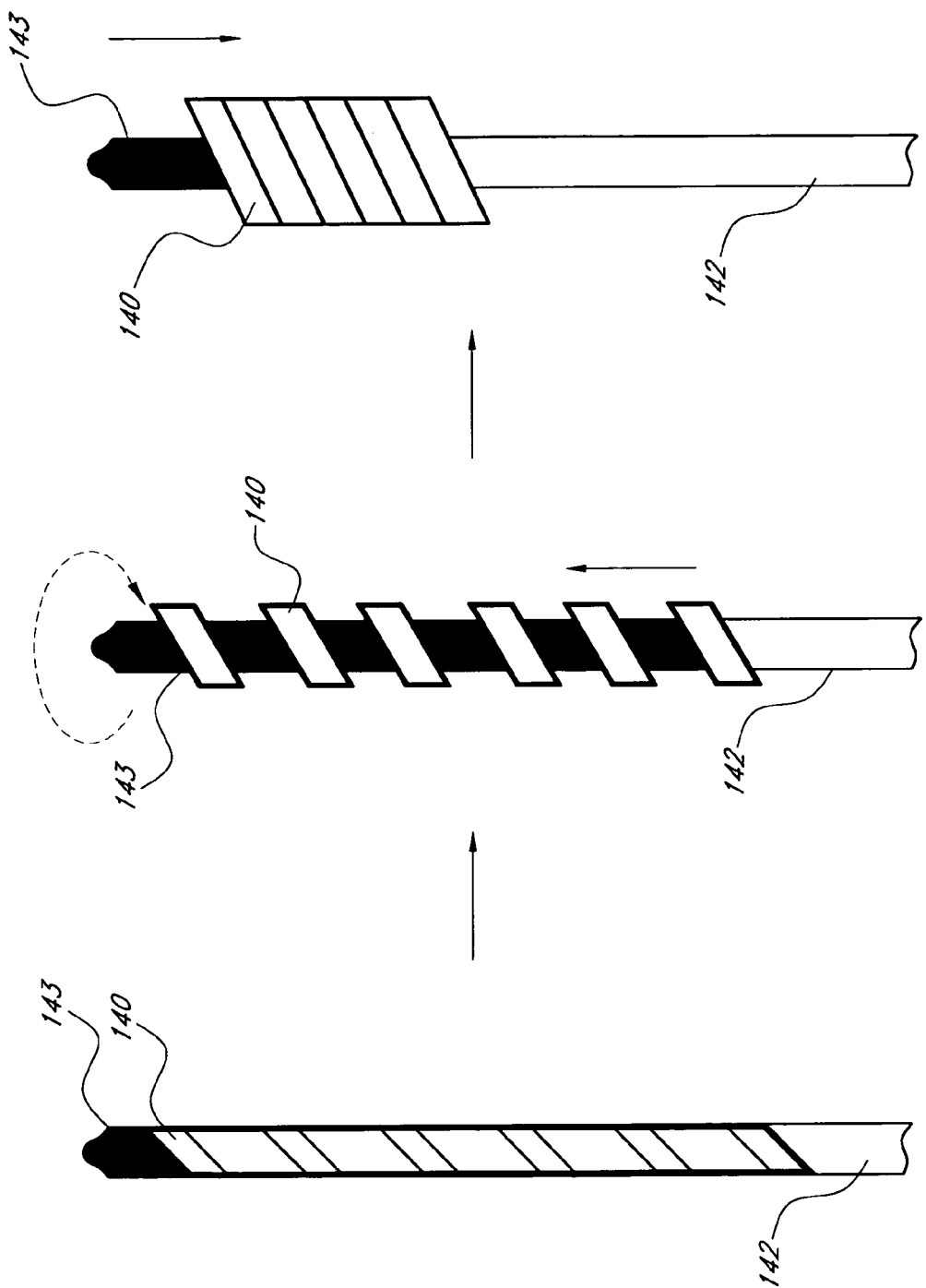

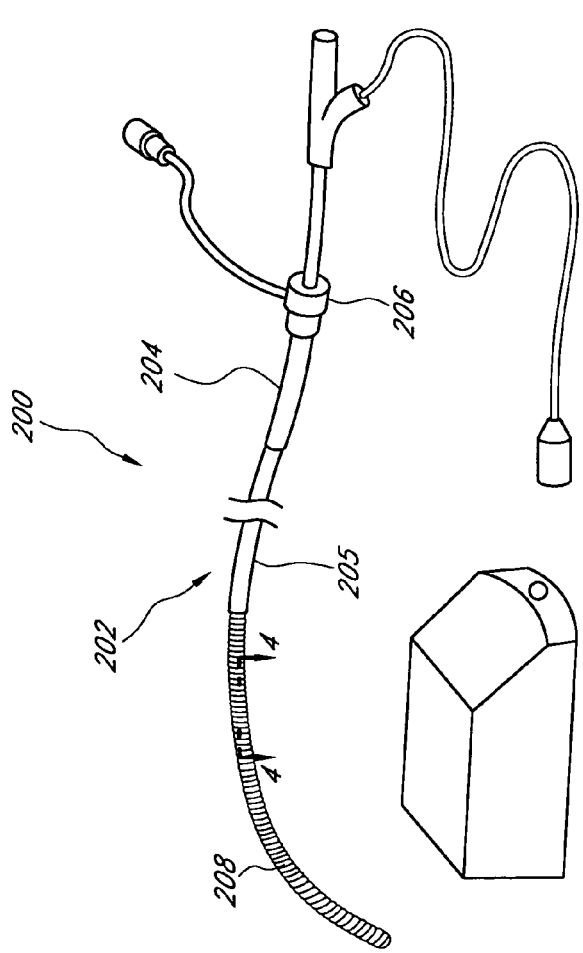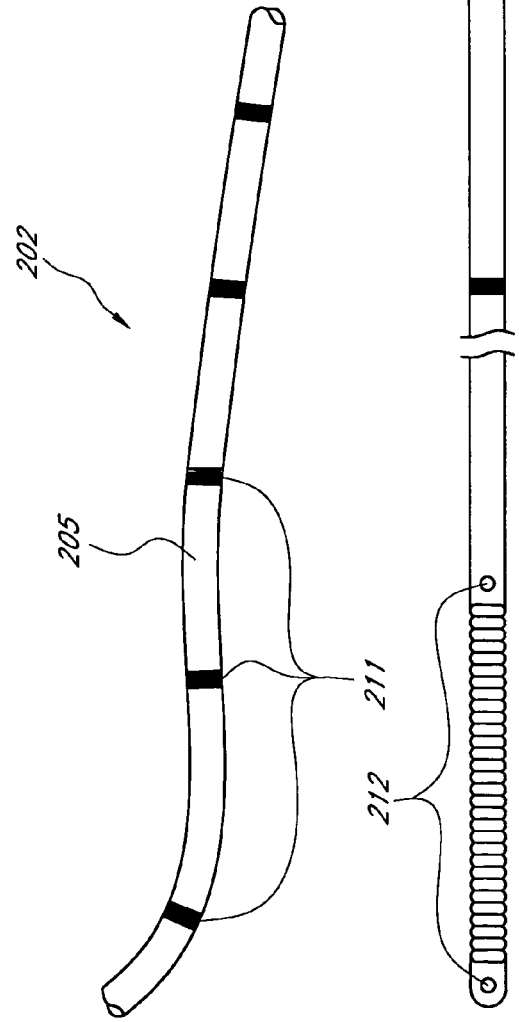
FIG. 14
FIG. 15A
FIG. 15B

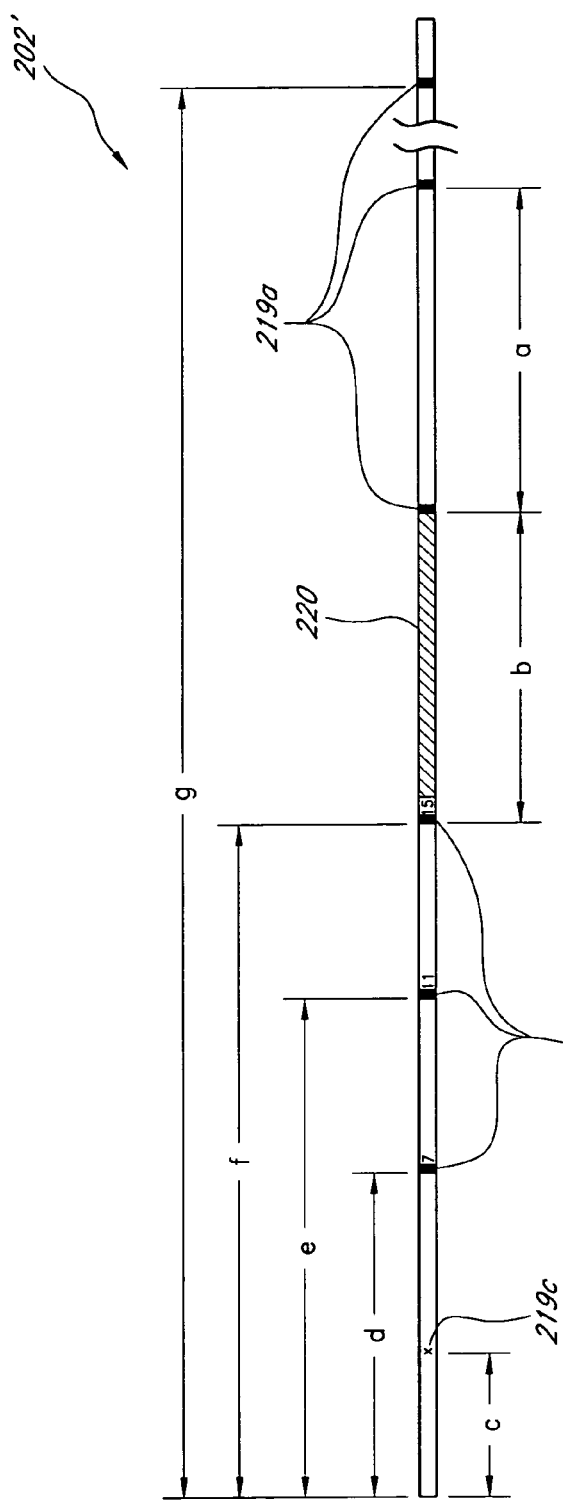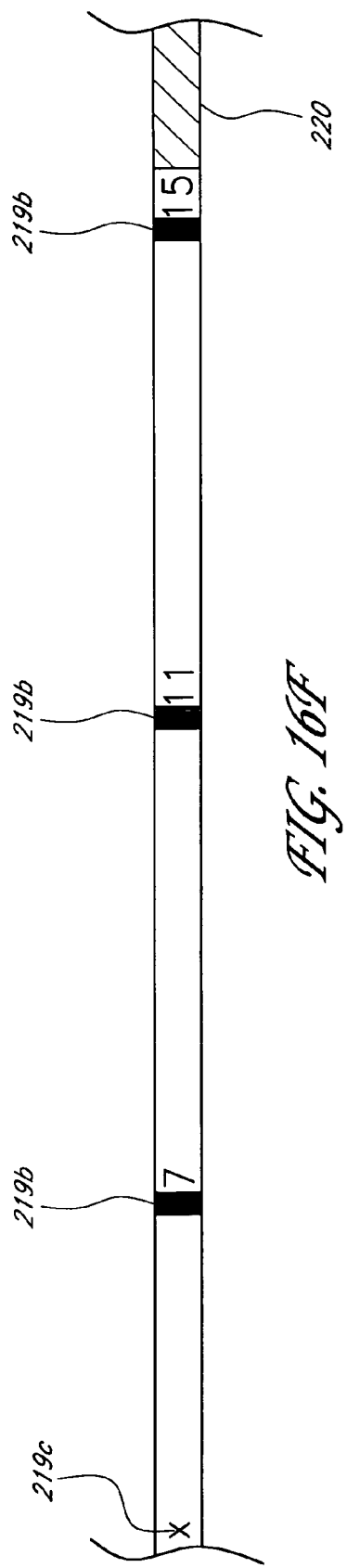
FIG. 16E
FIG. 16F

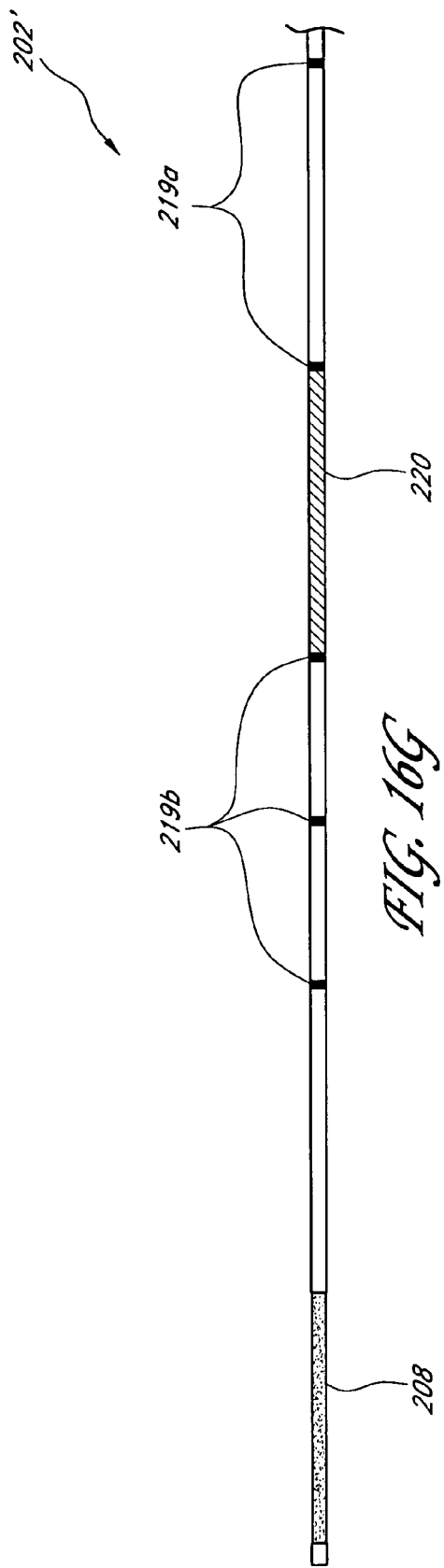
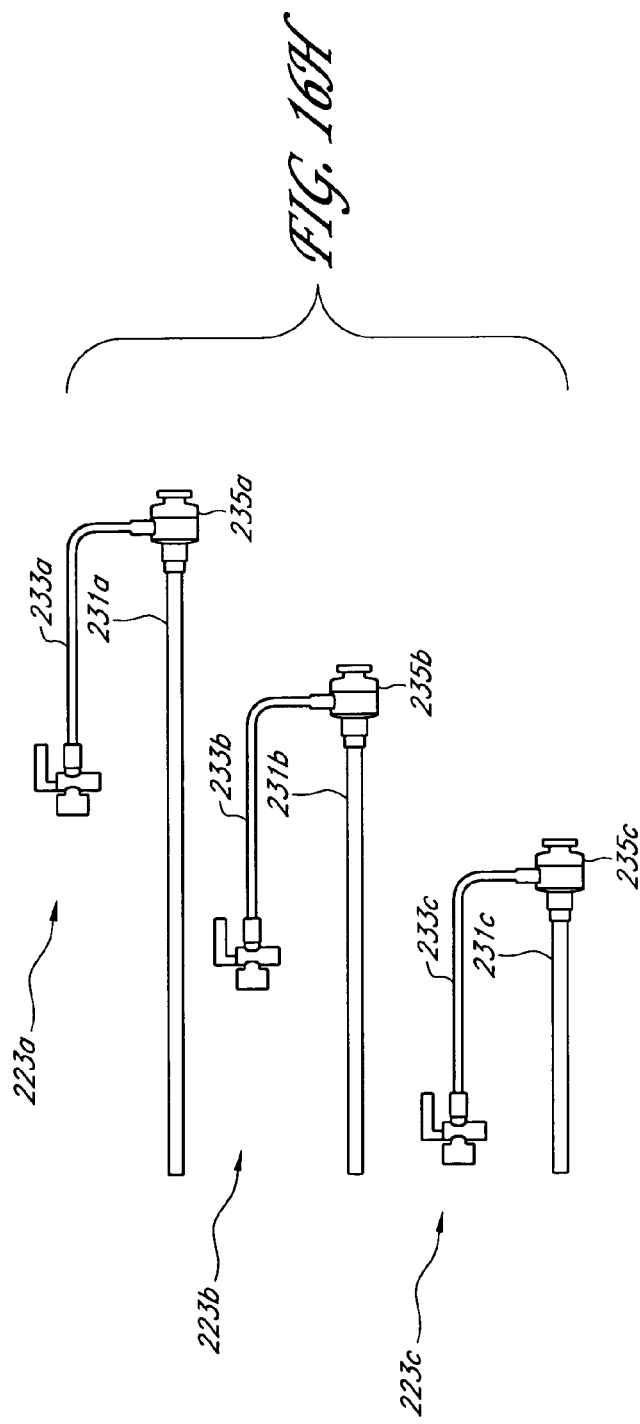
FIG. 16G
FIG. 16H

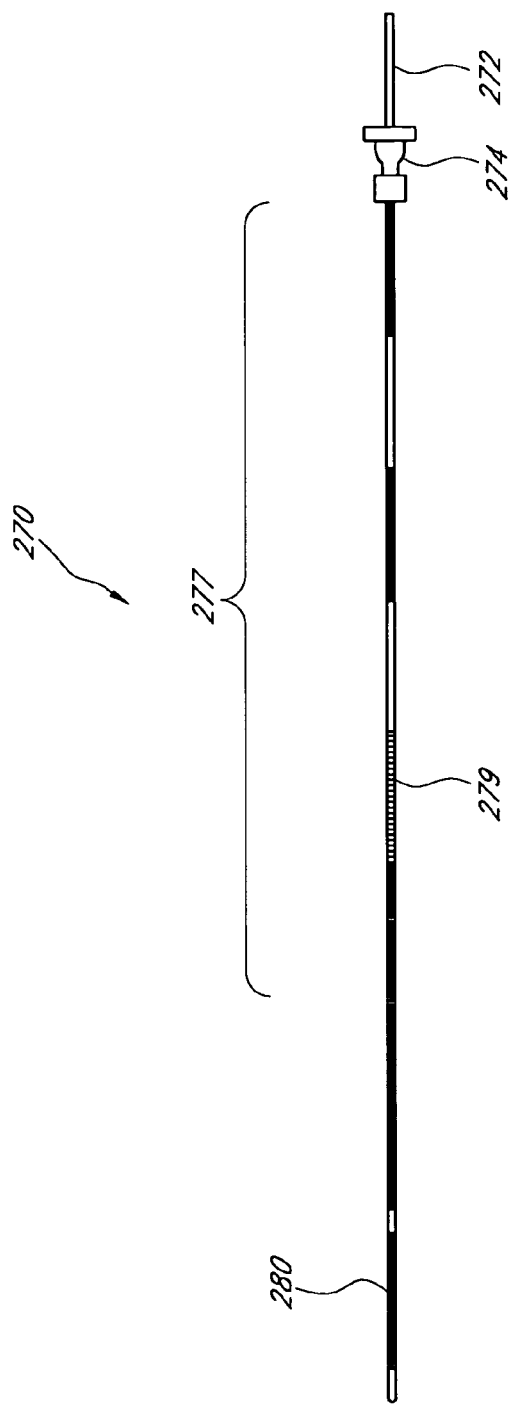
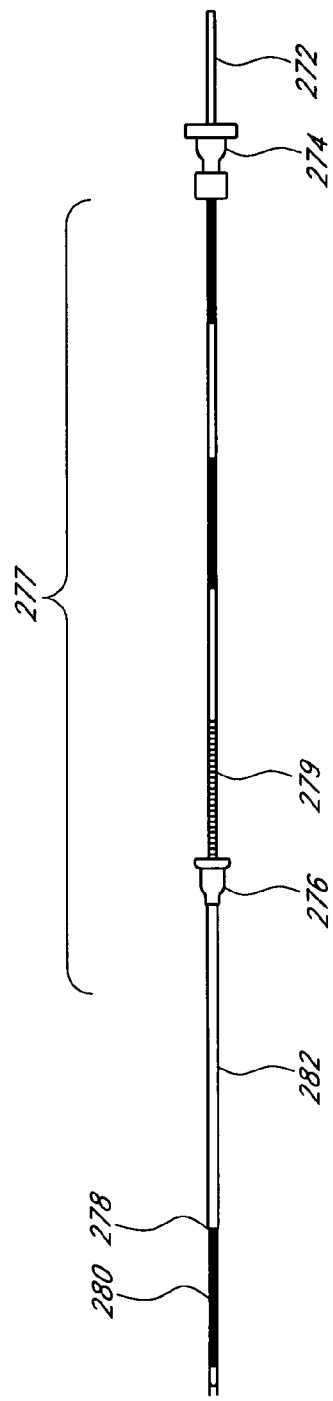

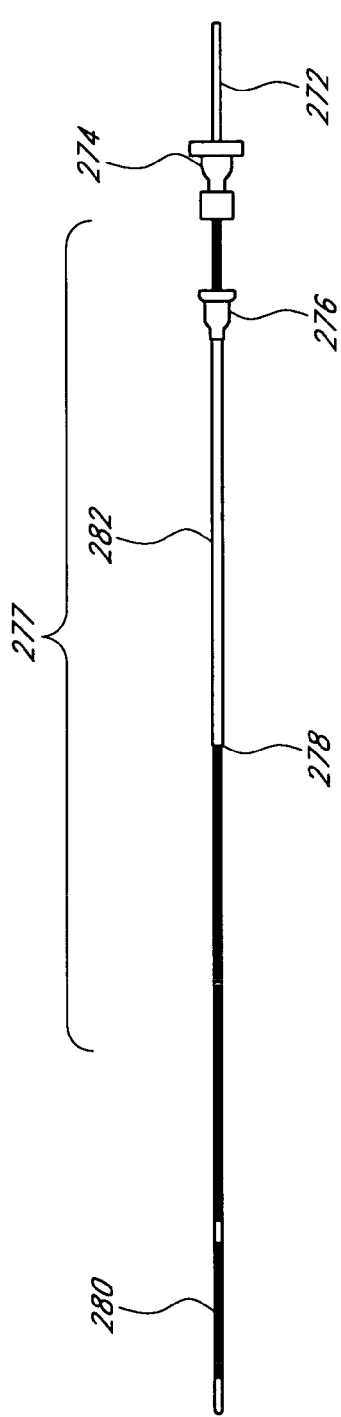
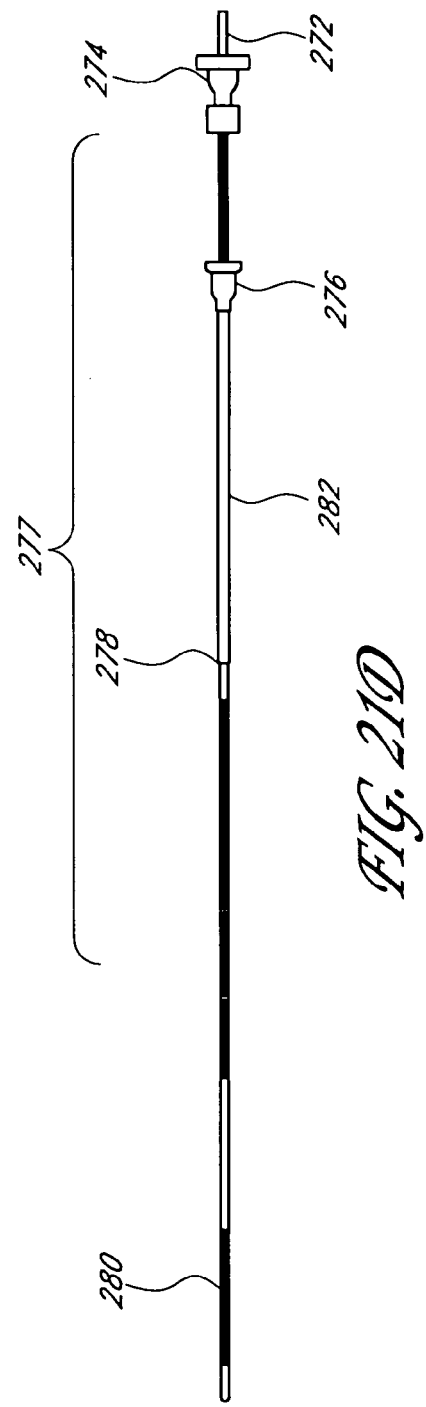
FIG. 21C
FIG. 21D

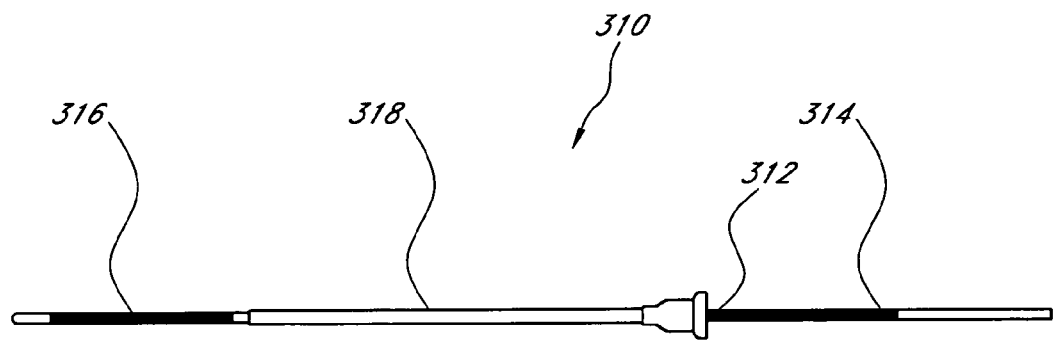
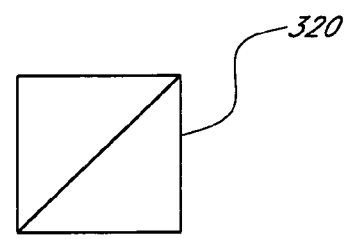
FIG. 23
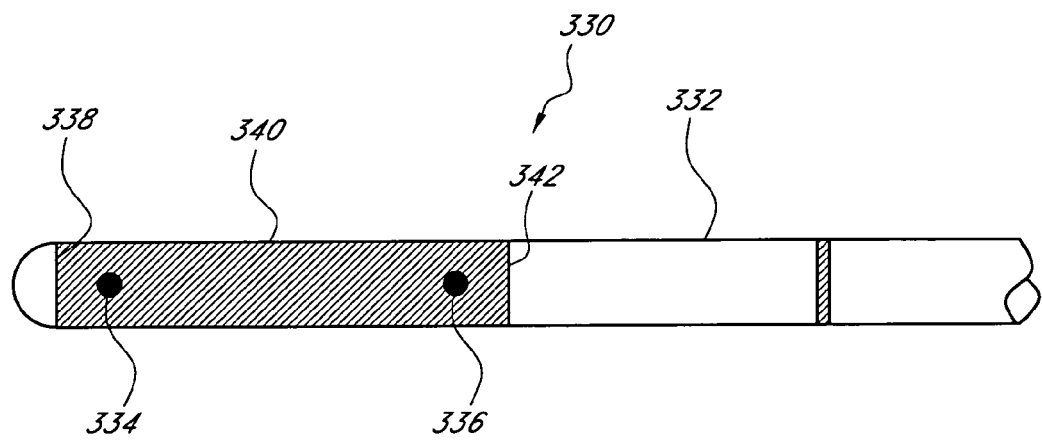
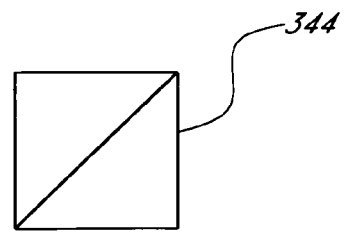
FIG. 24

APPARATUS AND METHOD FOR ENSURING SAFE OPERATION OF A THERMAL TREATMENT CATHETER

RELATED APPLICATIONS

This application claims the benefit of priority under 35 U.S.C. §119(e) of each of U.S. Provisional Application No. 60/780,948, filed on Mar. 9, 2006, entitled "SYSTEMS AND METHODS FOR TREATING A HOLLOW ANATOMICAL STRUCTURE," and U.S. Provisional Application No. 60/701,303, filed on Jul. 21, 2005, entitled "RESISTIVE ELEMENT SYSTEM," each of which is hereby incorporated herein by reference in its entirety and is to be considered a part of this specification.

BACKGROUND

1. Field

Certain disclosed embodiments relate to methods and apparatus for applying energy to constrict and/or shrink a hollow anatomical structure, such as a vein.

2. Description of the Related Art

The human venous system of the lower extremities consists essentially of the superficial venous system and the deep venous system with perforating veins connecting the two systems. The superficial system includes the long or great saphenous vein and the small saphenous vein. The deep venous system includes the anterior and posterior tibial veins which unite to form the popliteal vein, which in turn becomes the femoral vein when joined by the short saphenous vein.

The venous system contains numerous one-way valves for directing blood flow back to the heart. Venous valves are usually bicuspid valves, with each cusp forming a sack or reservoir for blood. Retrograde blood flow forces the free surfaces of the cusps together to prevent continued retrograde flow of the blood and allows only antegrade blood flow to the heart. When an incompetent valve is in the flow path, the valve is unable to close because the cusps do not form a proper seal, and retrograde flow of the blood cannot be stopped. When a venous valve fails, increased strain and pressure occur within the lower venous sections and overlying tissues, sometimes leading to additional, limb-distal valvular failure. Two venous conditions or symptoms which often result from valve failure are varicose veins and more symptomatic chronic venous insufficiency.

SUMMARY

Disclosed herein are systems and methods for ligating and/or substantially occluding a hollow anatomical structure (HAS), such as, for example, a vein. In particular, certain disclosed embodiments include devices having a therapeutic element, such as a resistive heating element, that is capable of directly applying energy to the inner wall of the hollow anatomical structure. In certain embodiments, this application of energy causes collagen denaturation and shrinkage such that the HAS diameter is substantially reduced and the HAS wall becomes thickened such that the end result is generally a HAS "lumen" filled with fibrin whereas fluid can no longer flow therethrough. Also disclosed are indexing methods and devices that facilitate treatment of successive portions of the hollow anatomical structure.

One embodiment comprises a catheter for use in treating a hollow anatomical structure. The catheter comprises an elongated shaft having a distal end and a proximal end; and an energy application device located proximate the distal end of the shaft. The energy application device has a first length. The catheter further comprises a plurality of index markers located along the shaft and proximal of the energy application device such that consecutive index markers are spaced apart by a second length. The second length comprises an indexing distance of the energy application device.

In one variation of the catheter, the second length is approximately equal to or slightly shorter than the first length. In a further variation, the first length is between approximately 2 centimeters and approximately 10 centimeters and the second length is between approximately 0.1 centimeter and approximately 1.5 centimeters less than the first length. In another further variation, the first length is approximately 7 centimeters and the second length is approximately 6.5 centimeters.

In some variations of the catheter, the shaft further comprises a stop-treatment marker or a last-treatment marker located proximal of the energy application device and distal of the plurality of index markers. In a further variation, the stop-treatment marker can include a plurality of warning markers corresponding to a plurality of introducer lengths.

In some variations of the catheter, the plurality of index markers can comprise any of the following: alphanumeric markers, color-coded markers, geometrically coded markers, at least one magnetic ink marker readable by an external sensor, or at least one detent in the shaft.

In one variation of the catheter, at least a portion of the catheter is sterile. In a further variation, a method can comprise sterilizing the catheter.

In some variations of the catheter, the energy application device can have an adjustable active length, and/or an active region which is adjustable in size. In a further variation, the energy application device comprises a heater element with a plurality of separately operable heater sections which are arranged longitudinally along the first length.

Another embodiment comprises a method for treating a hollow anatomical structure. The method comprises inserting a catheter having an energy application device having a first length and indexing marks on the catheter shaft proximal to the energy application device through an introducer sheath in a hollow anatomical structure of a patient. The method further comprises positioning the energy application device at a first treatment location in the hollow anatomical structure. The method further comprises, while the energy application device is at the first treatment location of the hollow anatomical structure, withdrawing the sheath or adjusting a reference point of the sheath until the reference point of the sheath is aligned with one of the indexing marks on the catheter shaft. The method further comprises applying energy with the energy application device to the first treatment location in the hollow anatomical structure; and positioning the catheter at one or more subsequent treatment locations in the hollow anatomical structure by moving the catheter shaft through the sheath until another one or more of the indexing marks is aligned with the reference point of the sheath. The method further comprises applying energy with the energy application device to each subsequent treatment location.

In some variations of the method, the reference point of the sheath comprises the proximal end of the sheath, or an adjustable reference marker.

In one variation, the method further comprises securing the sheath with respect to the hollow anatomical structure before moving the catheter to one or more subsequent treatment locations. Securing the sheath can optionally comprise securing the sheath to the patient.

Another embodiment comprises a method for treating a hollow anatomical structure. The method comprises inserting a catheter into a hollow anatomical structure of a patient. The catheter has an energy application device with a first length. The method further comprises applying energy, with the energy application device, to a first treatment location of the hollow anatomical structure. The method further comprises moving the catheter proximally to one or more additional treatment locations of the hollow anatomical structure, wherein each additional treatment location is offset by an indexing length from the preceding treatment location. The method further comprises applying energy, with the energy application device, to the one or more additional treatment locations of the hollow anatomical structure.

In one variation of the method, the indexing length is approximately equal to or slightly shorter than the first length.

In another variation of the method, moving the catheter proximally comprises aligning an index marking on the catheter with a reference point. The reference point can optionally be on an introducer through which the catheter is inserted.

Another variation of the method further comprises monitoring a temperature within the hollow anatomical structure.

In some variations of the method, applying energy to the first location can comprise applying energy to the first location at two distinct times, or applying energy to the first location for a longer duration than to any one of the additional locations. Where energy is applied to the first location for a longer duration, the hollow anatomical structure can optionally have a larger cross-sectional profile, as viewed along a longitudinal axis of the hollow anatomical structure, in the first location than in any of the additional locations. Where energy is applied to the first location for a longer duration, the hollow anatomical structure can comprise the great saphenous vein, and the first location can be closer to the saphenofemoral junction than is any of the additional locations.

Another embodiment comprises an apparatus. The apparatus comprises a catheter shaft extending from a proximal end to a distal end; an energy application device proximate the distal end of the catheter shaft; and markers along the length of the catheter shaft. The markers are spaced apart at a multiple of the length of the energy application device.

In one variation of the apparatus, the length of the energy application device is between approximately 2 centimeters and approximately 10 centimeters.

In another variation of the apparatus, the energy application device is a resistive heating device. Such an energy application device can optionally be a wound nichrome wire.

In another variation of the apparatus, the energy application device comprises a Resistance Temperature Detector (RTD) configured to sense the temperature of the energy application device by a measurement of the impedance of the energy application device.

In another variation of the apparatus, the energy application device comprises one or more radio frequency (RF) electrodes.

In another variation of the apparatus, the markers are spaced apart at a fraction of the length of the energy application device.

In another variation of the apparatus, at least a portion of the apparatus is sterile. A method can comprise sterilizing the apparatus.

Another variation of the apparatus further comprises at least one temperature sensor.

In another variation of the apparatus, the energy application device has an adjustable active length.

In another variation of the apparatus, the energy application device has an active region which is adjustable in size. Such an energy application device can optionally comprise a heater element with a plurality of separately operable heater sections which are arranged longitudinally.

Another embodiment comprises a method for treating a hollow anatomical structure. The method comprises inserting a catheter having a heating element coupled thereto, into a hollow anatomical structure; energizing the heating element at a first treatment position within the hollow anatomical structure; moving the catheter an indexed distance in a proximal direction to an additional treatment position within the hollow anatomical structure; and energizing the heating element at the additional treatment position.

In one variation of the method, the method further comprises repeating (a) moving the catheter an indexed distance to an additional treatment position, and (b) energizing the heating element at the additional treatment position, until a desired length of the hollow anatomical structure is treated.

In another variation of the method, the hollow anatomical structure comprises a human vein.

Another variation of the method further comprises determining the indexed distance with a plurality of markings along a shaft of the catheter.

In another variation of the method, moving the catheter the indexed distance comprises securing a proximal end of an indexing device to a shaft of the catheter; and extending the proximal end of the indexing device the indexed distance from a distal end of the indexing device, thereby moving the catheter shaft by the indexed distance from the distal end of the indexing device.

In another variation of the method, at least one of the additional treatment locations slightly overlaps the preceding treatment location.

In another variation of the method, energizing the heating element at the first treatment position comprises energizing the heating element at two distinct times.

In another variation of the method, energizing the heating element at the first treatment position comprises energizing the heating element for a longer duration than at any one of the additional treatment positions. In this variation, the hollow anatomical structure can optionally have a larger cross-sectional profile, as viewed along a longitudinal axis of the hollow anatomical structure, in the first treatment position than in any of the additional treatment positions. In this variation, the hollow anatomical structure can further optionally comprise the great saphenous vein, and the first treatment position can be closer to the sapheno-femoral junction than is any of the additional treatment positions.

Another embodiment comprises a catheter for treating a hollow anatomical structure. The catheter comprises an elongate shaft; means for applying energy to a hollow anatomical structure. The means for applying energy is secured to the shaft and has a first length. The catheter further comprises a plurality of means for indexing located along the shaft and proximal of the means for applying energy. Each of the plurality of means for indexing is spaced apart by a second length.

In one variation of the catheter, the second length is approximately equal to or slightly less than the first length.

In another variation of the catheter, the means for applying energy comprises a resistive heating device.

Another embodiment comprises a catheter for use in treating a hollow anatomical structure. The catheter comprises an elongated shaft having a distal end and a proximal end; and an energy application device coupled to the shaft. The energy application device has a first length. The catheter further comprises a plurality of index markers located along the shaft and proximal of the energy application device such that consecutive index markers are spaced apart by a second length.

The second length is equal to the first length less a decrement. The decrement is between 1% and 15% of the first length.

In one variation of the catheter, the first length is between 2 and 10 centimeters, and the decrement is between 0.1 and 1.5 centimeters.

In another variation of the catheter, the first length is approximately 7 centimeters and the second length is approximately 6.5 centimeters.

In another variation of the catheter, the shaft further comprises a stop-treatment marker located distal of the plurality of index markers, and the stop-treatment marker is distinct from the index markers.

In another variation of the catheter, the energy application device comprises an electrically driven heater element.

In another variation of the catheter, the energy application device has an energy coupling surface which extends along the first length. In such a variation, the first length can be at least ten times a width of the energy application device.

In another variation of the catheter, the energy application device is configured to generate heat internally and transfer heat radially outwardly away from a central longitudinal axis of the energy application device.

Another embodiment comprises an introducer sheath. The introducer sheath comprises a sheath lumen having a distal end which is insertable into a hollow anatomical structure. The sheath lumen extends generally along a luminal axis in a distal-to-proximal direction. The introducer sheath further comprises an adjustable reference marker connected to the sheath. The longitudinal position, as measured along the luminal axis, of the reference marker is adjustable.

In one variation of the introducer sheath, the adjustable reference marker includes a flexible elongate member of variable length that is attached to the proximal end of the sheath.

In another variation of the introducer sheath, the adjustable reference marker is removably connected to the sheath.

Another embodiment comprises a hollow anatomical structure treatment system, which comprises the introducer sheath, and a catheter shaft disposed in the sheath lumen. The catheter shaft extends proximally past the reference marker, and has a plurality of indexing marks. The reference marker is longitudinally adjustable relative to the catheter shaft to permit alignment of the reference marker with one of the indexing marks without need for movement of the shaft relative to the sheath.

Another embodiment comprises a method of facilitating the treatment of a hollow anatomical structure. The method comprises initiating power delivery to an energy application device of a hollow anatomical structure treatment device; and measuring an operating parameter of the treatment device. The operating parameter is relevant to energy coupling between the energy application device and its surroundings. The method further comprises determining whether the operating parameter satisfies a first energy coupling condition within a first time interval following the initiating; and, if the operating parameter does not satisfy the first energy coupling condition within the first time interval, providing a warning.

In one variation of the method, the operating parameter is a measure of the temperature of at least a portion of the treatment device. In such a variation, the operating parameter can optionally be a measure of the temperature of at least a portion of the energy application device.

In another variation of the method, the operating parameter is a measure of the power delivered to the energy application device.

In another variation of the method, the power delivery is provided via an electric current in the energy application device. In such a variation, the operating parameter can optionally be one of the following: a measure of the electrical power delivered to the energy application device; a measure of the electric current; and/or a measure of the electrical impedance of the energy application device. In such a variation, the energy application device can optionally comprise a conducting coil.

In another variation of the method, the operating parameter is a measure of the temperature of at least a portion of the energy application device, and the first energy coupling condition comprises meeting or exceeding a first target temperature value for the temperature of at least a portion of the energy application device. In such a variation, the first energy coupling condition can optionally comprise meeting or exceeding the first target temperature value within a prescribed period of time after initiating power delivery.

In another variation of the method, the operating parameter is a measure of the temperature of at least a portion of the energy application device, and the first energy coupling condition comprises absence of sudden changes to the temperature of at least a portion of the energy application device.

In another variation of the method, the operating parameter is a measure of the power delivered to the energy application device, and the first energy coupling condition comprises a delivered power magnitude which is substantially similar to a reference waveform of expected power magnitude.

In another variation of the method, the operating parameter is a measure of the power delivered to the energy application device, and the first energy coupling condition comprises a rate of change of the magnitude of power delivered to the energy application device which is substantially similar to a reference waveform of expected power delivered after achievement of a target temperature value.

In another variation of the method, the power delivery is provided via an electric current in the energy application device, the operating parameter is a measure of the electric current, and the first energy coupling condition comprises a delivered electric current magnitude which is substantially similar to a reference waveform of expected electric current magnitude.

In another variation of the method, the power delivery is provided via an electric current in the energy application device, the operating parameter is a measure of the electric current, and the first energy coupling condition comprises a rate of change of the magnitude of electric current delivered to the energy application device which is substantially similar to a reference waveform of expected electric current delivered after achievement of a target temperature value.

In another variation of the method, the power delivery is provided via an electric current in the energy application device, the operating parameter is a measure of the electrical impedance of the energy application device, and the first energy coupling condition comprises a measured electrical impedance magnitude which is substantially similar to a reference waveform of expected electrical impedance of the energy application device.

In another variation of the method, the power delivery is provided via an electric current in the energy application device, the operating parameter is a measure of the electrical impedance of the energy application device, and the first energy coupling condition comprises a measured rate of change of the magnitude of the electrical impedance of the energy application device which is substantially similar to a reference waveform of expected electrical impedance of the energy application device.

Another variation of the method further comprises terminating or reducing power delivery to the energy application device if the operating parameter does not satisfy the first energy coupling condition within the first time interval.

In another variation of the method, the warning comprises a message to adjust the environment of the hollow anatomical structure treatment device within a patient. In such a variation, the message instructs a user to adjust or improve compression of the portion of the hollow anatomical structure containing the treatment device.

Another variation of the method further comprises determining whether the operating parameter satisfies a second energy coupling condition within a second time interval following the first time interval; and, if the operating parameter does not satisfy the second energy coupling condition within the second time interval, providing a warning. In such a variation, the method can optionally further comprise terminating or reducing power delivery to the energy application device if the operating parameter does not satisfy the second energy coupling condition within the second time interval.

Another embodiment comprises a method of facilitating the treatment of a hollow anatomical structure. The method comprises initiating power delivery to an energy application device of a hollow anatomical structure treatment device; measuring two operating parameters of the treatment device, the operating parameters being relevant to energy coupling between the energy application device and its surroundings; determining whether the operating parameters satisfy a first energy coupling condition within a first time interval following the initiating; and, if the operating parameters do not satisfy the first energy coupling condition within the first time interval, providing a warning.

In some variations of the method, the operating parameters are the temperature of at least a portion of the energy application device and the electrical impedance of the energy application device. In such a variation, the energy application device can optionally comprise a resistance temperature device; and the method can further optionally comprise computing a temperature of the energy application device based on the electrical impedance of the energy application device, and the first energy coupling condition can further optionally comprise correlation of the measured temperature of the energy application device to the computed temperature of the energy application device.

Another embodiment comprises an apparatus for use in treating a hollow anatomical structure. The apparatus comprises an energy application device adapted to receive power from a power source, and a measuring device that measures an operating parameter of the energy application device. The operating parameter is relevant to energy coupling between the energy application device and its surroundings. The apparatus further comprises a module in communication with the measuring device. The module is configured to determine whether the operating parameter satisfies a first energy coupling condition within a first time interval following the initiation of power delivery to the energy application device. The apparatus further comprises a warning device in communication with the module. The module is further configured to cause the warning device to provide a warning if the operating parameter does not satisfy the first energy coupling condition within the first time interval.

In one variation of the apparatus, the operating parameter is a measure of the temperature of at least a portion of the energy application device.

In another variation of the apparatus, the operating parameter is a measure of the power delivered to the energy application device.

In another variation of the apparatus, the energy application device is adapted to receive power via an electric current.

In such a variation, the operating parameter can optionally be any of the following: a measure of the electrical power delivered to the energy application device; a measure of the electric current; and/or a measure of the electrical impedance of the energy application device.

In another variation of the apparatus, the energy application device comprises a conducting coil.

In another variation of the apparatus, the operating parameter is a measure of the temperature of at least a portion of the energy application device, and the first energy coupling condition comprises meeting or exceeding a first target temperature value for the temperature of at least a portion of the energy application device. In such a variation, the first energy coupling condition can optionally comprise meeting or exceeding the first target temperature value within a prescribed period of time after initiating power delivery.

In another variation of the apparatus, the operating parameter is a measure of the temperature of at least a portion of the energy application device, and the first energy coupling condition comprises absence of sudden changes to the temperature of at least a portion of the energy application device.

In another variation of the apparatus, the energy application device is adapted to receive power via an electric current, and the first energy coupling condition comprises a delivered power magnitude which is substantially similar to a reference waveform of expected power magnitude.

In another variation of the apparatus, the energy application device is adapted to receive power via an electric current, and the first energy coupling condition comprises a rate of change of the magnitude of power delivered to the energy application device which is substantially similar to a reference waveform of expected power delivered after achievement of a target temperature value.

In another variation of the apparatus, the energy application device is adapted to receive power via an electric current, the operating parameter is a measure of the electric current, and the first energy coupling condition comprises a delivered electric current magnitude which is substantially similar to a reference waveform of expected electric current magnitude.

In another variation of the apparatus, the energy application device is adapted to receive power via an electric current, the operating parameter is a measure of the electric current, and the first energy coupling condition comprises a rate of change of the magnitude of electric current delivered to the energy application device which is substantially similar to a reference waveform of expected electric current delivered after achievement of a target temperature value.

In another variation of the apparatus, the energy application device is adapted to receive power via an electric current, the operating parameter is a measure of the electrical impedance of said energy application device, and the first energy coupling condition comprises a measured electrical impedance magnitude which is substantially similar to a reference waveform of expected electrical impedance of the energy application device.

In another variation of the apparatus, the energy application device is adapted to receive power via an electric current, the operating parameter is a measure of the electrical impedance of said energy application device, and the first energy coupling condition comprises a measured rate of change of the magnitude of the electrical impedance of the energy application device which is substantially similar to a reference waveform of expected electrical impedance of the energy application device.

In another variation of the apparatus, the module is further configured to terminate or reduce power delivery to the energy application device if the operating parameter does not satisfy the first energy coupling condition within the first time interval.

In another variation of the apparatus, the module is further configured to cause the warning device to provide a message to a user of the apparatus to adjust the environment of the hollow anatomical structure treatment device within a patient. In such a variation, the message can optionally instruct a user to adjust or improve compression of the portion of the hollow anatomical structure containing the treatment device.

In another variation of the apparatus, the module is further configured to determine whether the operating parameter satisfies a second energy coupling condition within a second time interval following the first time interval, and to provide a warning if the operating parameter does not satisfy the second energy coupling condition within the second time interval. In such a variation, the module can optionally be further configured to terminate or reduce power delivery to the energy application device if the operating parameter does not satisfy the second energy coupling condition within the second time interval.

Another embodiment comprises a method of avoiding interference with heat treatment of a hollow anatomical structure within a patient. The method comprises initiating power delivery to an energy application device of a hollow anatomical structure treatment device. The energy application device is disposed within a hollow anatomical structure. The method further comprises measuring an operating parameter of the treatment device. The operating parameter is relevant to energy coupling between the energy application device and its surroundings. The method further comprises determining whether the operating parameter satisfies a first energy coupling condition within a first time interval following the initiating. The method further comprises taking corrective measures to improve the energy coupling between the energy application device and its surroundings, if the operating parameter does not satisfy the first energy coupling condition within the first time interval.

In some variations of this method, the operating parameter can be any one or more of the following: a measure of the temperature of at least a portion of the energy application device; a measure of the power delivered to the energy application device; and/or a measure of electrical impedance within a current path associated with the delivery of power to the energy application device.

In some variations of this method, the corrective measures can comprise any one or more of the following: applying compression in the vicinity of the hollow anatomical structure containing the energy application device; adjusting the location or force of existing compression in the vicinity of the hollow anatomical structure containing the energy application device; and/or verifying effective occlusion of flow within the hollow anatomical structure in the vicinity of the energy application device.

Another embodiment comprises a method. The method comprises sensing a temperature on or near at least a portion of a heat application device of a hollow anatomical structure treatment device; determining whether the temperature satisfies a required initial temperature condition; receiving a request to initiate power delivery to the heat application device of the hollow anatomical structure treatment device; and performing a safety procedure to interrupt a normal power-up process for the heat application device, if the temperature does not satisfy the required initial temperature condition.

In one variation of the method, the method further comprises allowing a normal power-up process for the heat application device to proceed if the temperature satisfies the required initial temperature condition.

In another variation of the method, determining whether the temperature satisfies a required initial temperature condition, comprises determining whether the temperature has satisfied the required initial temperature condition at any time during a temperature sensing period. In such a variation, the temperature sensing period can optionally begin after connection of the treatment device to a power source. In such a variation, the temperature sensing period can further optionally end before delivery of therapeutic energy from the power source to the treatment device.

In another variation of the method, the safety procedure comprises preventing the initiation of power delivery to the heat application device.

In another variation of the method, the safety procedure comprises ceasing the delivery of power to the heat application device.

In another variation of the method, the required initial temperature condition comprises that the temperature meet or exceed a minimum temperature. In such a variation, the minimum temperature can optionally be any one or more of the following: significantly above an expected ambient room temperature; substantially at an expected internal temperature of the hollow anatomical structure to be treated with the treatment device; and/or 5 to 10 degrees Celsius lower than the normal physiologic internal temperature of a hollow anatomical structure of the type normally treated with the treatment device.

In another variation of the method, the required initial temperature condition comprises that the temperature fall within an acceptable temperature range. In such a variation, the acceptable temperature range can optionally be any one or more of the following: significantly above an expected ambient room temperature; bracketing an expected internal temperature of the hollow anatomical structure to be treated with the treatment device; and/or bracketing a temperature which is 5 to 10 degrees Celsius lower than the normal physiologic internal temperature of a hollow anatomical structure of the type normally treated with the treatment device.

Another variation of the method further comprises providing a warning if the temperature does not satisfy the required initial temperature condition.

Another variation of the method further comprises (a) verifying that the heat application device is properly disposed within a hollow anatomical structure of a patient; and (b) manually overriding the safety procedure and initiating a power-up process for the heat application device, if the temperature does not satisfy the required initial temperature condition.

Another embodiment comprises an apparatus for use in treating a hollow anatomical structure. The apparatus comprises a heat application device adapted to receive power from a power source; a user interface adapted to receive a request from a user to initiate power delivery to the heat application device; a temperature measuring device for measuring a temperature within or near the heat application device; and a module in communication with the temperature measuring device and the user interface. The module is configured to determine whether a temperature measured by the temperature measuring device satisfies a required initial temperature condition. The module is further configured to follow a safety procedure to interrupt a normal power-up process for the heat application device if the temperature measured by the temperature measuring device does not satisfy the required initial temperature condition.

In one variation of the apparatus, the module is further configured to follow a normal power-up process for the heat application device if the temperature measured by the temperature measuring device satisfies the required initial temperature condition.

In another variation of the apparatus, the module is further configured to determine whether the temperature has satisfied the required initial temperature condition at any time during a temperature sensing period.

In another variation of the apparatus, the safety procedure comprises preventing the initiation of power delivery to the heat application device.

In another variation of the apparatus, the safety procedure comprises ceasing the delivery of power to the heat application device.

In another variation of the apparatus, the required initial temperature condition comprises that the temperature meet or exceed a minimum temperature.

In another variation of the apparatus, the minimum temperature is above an expected ambient room temperature In another variation of the apparatus, the minimum temperature is substantially at an expected internal temperature of the hollow anatomical structure to be treated with the treatment device.

In another variation of the apparatus, the minimum temperature is 5 to 10 degrees Celsius lower than the normal physiologic internal temperature of a hollow anatomical structure of the type normally treated with the treatment device.

In another variation of the apparatus, the required initial temperature condition comprises that the temperature fall within an acceptable temperature range. In such a variation, the acceptable temperature range can optionally be any one or more of the following: significantly above an expected ambient room temperature; bracketing an expected internal temperature of the hollow anatomical structure to be treated with the treatment device; and/or bracketing a temperature which is 5 to 10 degrees Celsius lower than the normal physiologic internal temperature of a hollow anatomical structure of the type normally treated with the treatment device.

Another variation of the apparatus further comprises a warning device in communication with the module, wherein the module is further configured to cause the warning device to provide a warning if the temperature does not satisfy the required initial temperature condition.

In another variation of the apparatus, the user interface is further adapted to receive a request from a user to manually override the safety procedure; and the module is further configured to initiate a power-up process for the heat application device upon receiving a user request to manually override the safety procedure.

In certain embodiments, a hollow anatomical structure therapy system is disclosed which comprises: an energy application device suitable for insertion into a hollow anatomical structure; a power source in communication with the energy application device, the power source comprising a processor and program instructions executable by the processor such that the power source is operable to: (a) deliver power to the energy application device during a first power delivery phase; (b) measure time elapsing during power delivery; (c) assess performance of the therapy system during the first power delivery phase; and (d) if the performance of the therapy system during the first power delivery phase is satisfactory, deliver power to the energy application device during a second power delivery phase.

In a further variation, the energy application device is selected from the group consisting of an electrically driven heating element, an electrode, and a laser.

In further variations, the energy application device comprises an electrically driven heating element with an energy coupling surface, the surface having a distal-to-proximal length which is at least fifteen times a width of the heating element.

In further variations, the system further comprises a catheter having a shaft to which the energy application device is coupled.

In other variations, the system further comprises a temperature sensor configured to sense at least one of (i) a temperature of at least a portion of the energy application device, and (ii) a temperature of tissue in thermal communication with the energy application device.

In a further variation of the system, the program instructions are executable by the processor such that the power source is further operable to: deliver power to the energy application device to reach a first treatment temperature; and deliver power to the energy application device to reach a subsequent second treatment temperature which is lower than the first treatment temperature.

In a further variation of the system, the program instructions are executable by the processor such that the power source is further operable to determine expiration of the first power delivery phase based on temperature measurement results obtained by the temperature sensor.

In a further variation of the system, the first power delivery phase is 10 seconds or less in duration.

In a further variation of the system, satisfactory performance of the therapy system comprises reaching or exceeding a target temperature within a time limit. In a further variation of the system, the program instructions are executable by the processor such that the power source proceeds to the second power delivery phase only when the temperature sensor senses the target temperature within the time limit. In a further variation of the system, the program instructions are executable by the processor such that the power source is further operable to determine expiration of the first power delivery phase when the temperature sensor senses a target temperature within a time limit. In a further variation of the system, the time limit is six seconds or less.

In a further variation of the system, the target temperature is approximately 120 degrees Celsius.

In a further variation of the system, the combined duration of the first power delivery phase and the second power delivery phase is 60 seconds or less.

In certain embodiments, a hollow anatomical structure therapy system is disclosed which comprises: a heat delivery device suitable for insertion into a hollow anatomical structure; a power source in communication with the heat delivery device, the power source being programmed to: (a) deliver power to the heat delivery device during a temperature ramp-up phase; (b) measure time elapsing during power delivery; (c) monitor operation of the heat delivery device; and (d) if the operation of the heat delivery device either during or shortly after the temperature ramp-up phase is acceptable, deliver power to the heat delivery device after the temperature ramp-up phase.

In a further variation of the system, the heat delivery device is selected from the group consisting of an electrically driven heating element, an electrode, and a laser. In a further variation of the system, the heat delivery device comprises an electrically driven heating element with an energy coupling surface, the surface having a distal-to-proximal length which is at least fifteen times a width of the heating element.

Another variation of the system further comprises a catheter having a shaft to which the heat delivery device is coupled.

Another variation of the system further comprises a temperature sensor configured to sense at least one of (i) a temperature of a portion of the heat delivery device, and (ii) a temperature of tissue in thermal communication with the heat delivery device.

In a further variation of the system, acceptable operation of the heat delivery device during or shortly after the temperature ramp-up phase comprises reaching or exceeding a target temperature within a time limit. In a further variation of the system, acceptable operation of the heat delivery device during or shortly after the temperature ramp-up phase comprises falling below a target temperature within a time limit. In a further variation of the system, the combined duration of the temperature ramp-up phase and a subsequent power delivery phase is 60 seconds or less.

In a further variation of the system, the power source is further programmed to: deliver power to the heat delivery device to reach a first treatment temperature; and deliver power to the heat delivery device to reach a subsequent second treatment temperature which is lower than the first treatment temperature.

In certain embodiments, a method of treating a hollow anatomical structure is disclosed, the method comprising: inserting a heat delivery device into a hollow anatomical structure; delivering power to the heat delivery device during a temperature ramp-up phase; measuring time elapsing during power delivery; monitoring operation of the heat delivery device; and if the operation of the heat delivery device during or shortly after the temperature ramp-up phase is acceptable, delivering power to the heat delivery device after the temperature ramp-up phase.

In a further variation, the method additionally comprises: delivering power to the heat delivery device to reach a first treatment temperature; and delivering power to the heat delivery device to reach a subsequent second treatment temperature which is lower than the first treatment temperature.

In a further variation of the method, the heat delivery device is selected from the group consisting of an electrically driven heating element, an electrode, and a laser. In a further variation of the method, the heat delivery device comprises an electrically driven heating element with an energy coupling surface, the surface having a distal-to-proximal length which is at least fifteen times a width of the heating element.

In a further variation, the method additionally comprises measuring a temperature of at least one of (i) at least a portion of the heat delivery device, and (ii) a portion of the hollow anatomical structure being treated.

In a further variation of the method, monitoring operation of the heat delivery device comprises determining whether the measured temperature reaches or exceeds a target temperature within a time limit. In a further variation of the method, operation of the heat delivery device comprises determining whether the measured temperature falls below a target temperature within a time limit. In a further variation, the method additionally comprises proceeding to deliver power to the heat delivery device after the temperature ramp-up phase only when the target temperature is reached or exceeded within the time limit. In a further variation, the method additionally comprises proceeding to deliver power to the heat delivery device after the temperature ramp-up phase only when the target temperature falls below a target temperature within a time limit.

In a further variation of the method, monitoring operation of the heat delivery device comprises comparing a measurement of electrical impedance with a reference waveform.

In a further variation, the method additionally comprises displaying an instruction to adjust treatment of the hollow anatomical structure if the operation of the heat delivery device during the temperature ramp-up phase is not acceptable.

In a further variation of the method, displaying an instruction to adjust treatment of the hollow anatomical structure comprises displaying an instruction to adjust compression of the hollow anatomical structure.

In a further variation of the method, the hollow anatomical structure comprises a vein.

In certain embodiments, a method is disclosed for treatment of hollow anatomical structures that comprises: inserting an electrically driven heating element into the hollow anatomical structure, the heating element extending distally along a longitudinal axis of the element, the heating element having a length and a width measured orthogonal to the longitudinal axis, the length being greater than the width; powering the heating element and thereby causing the heating element to reach or exceed a minimal treatment temperature; moving the heating element within the hollow anatomical structure along a lengthwise direction of the hollow anatomical structure, and maintaining the heating element at or above the minimal treatment temperature while moving the heating element along the lengthwise direction. In a further variation, the movement of the heating element may be initiated after an initial delay after the minimal treatment temperature is reached.

In further variations of the method, the moving comprises moving the heating element without stopping along a treatment length of the hollow anatomical structure, and the treatment length is greater than the heating element length. In other variations of the method, the movement of the heating element may be temporarily stopped or slowed when the temperature of the heating element deviates from a target treatment temperature by more than 3 degrees Celsius.

In further variations of the method, the minimal treatment temperature may be an internal temperature of the heating element, or may be a temperature measured at or adjacent to the heating element. In further variations of the method, the minimal treatment temperature is sufficient to cause durable reduction of the diameter of the hollow anatomical structure. In further variations of the method, the minimal treatment temperature is sufficient to cause absence of patency of the hollow anatomical structure. In further variations of the method, the minimal treatment temperature may be within a range of 80-140 degrees Celsius, and may be approximately 120 degrees Celsius or approximately 95 degrees Celsius.

In another variation of the method, the heating element is coupled to a shaft of a catheter. In a further variation of the method, heated fluid is delivered from a tip of the catheter while moving the heating element. In other variations of the method, the fluid may be passed through a lumen of the catheter, heating the fluid with the heating element as the fluid passes through the lumen before exiting the catheter tip.

In a variation of the method, the length of the heating element is at least equal to fifteen times its width. In a further variation of the method, the heating element extends to the distal end of the catheter. In a further variation of the method, the heating element may be a coil having a variable pitch.

In a further variation of the method, laser light is applied to the hollow anatomical structure with the catheter.

In another embodiment, a method is disclosed for treatment of hollow anatomical structures that comprises: inserting an electrically driven heating element into the hollow anatomical structure, the heating element extending distally along a longitudinal axis of the element, the heating element having a length and a width measured orthogonal to the longitudinal axis, the length being greater than the width; moving the heating element within the hollow anatomical structure along a lengthwise direction of the hollow anatomical structure while applying electrical power to the heating element within a treatment power level range, and applying power to the heating element within the treatment power level range while moving the heating element along the lengthwise direction.

In a variation of the method, the moving comprises moving the heating element without stopping along a treatment length of the hollow anatomical structure, the treatment length being greater than the heating element length.

In a variation of the method, the treatment power level range is 20-40 W.

In a variation of the method, the heating element is coupled to a shaft of a catheter.

A variation of the method further comprises delivering heated fluid from a tip of the catheter while moving the heating element. Another variation of the method further comprises passing the fluid through a lumen of the catheter and heating the fluid with the heating element as the fluid passes through the lumen before the fluid exits the catheter tip.

In a variation of the method, the length of the heating element is at least equal to fifteen times the width thereof. In another variation of the method, the heating element is a coil having a variable pitch. In another variation of the method, the heating element extends to a distal end of the catheter.

A variation of the method further comprises applying laser light to the hollow anatomical structure with the catheter.

In another embodiment, methods are disclosed for treatment of hollow anatomical structures comprising: inserting an electrically driven heating element into the hollow anatomical structure, the heating element extending distally along a longitudinal axis of the element, the heating element having a fixed profile in a plane orthogonal to a longitudinal axis thereof; powering the heating element and thereby causing the heating element to reach or exceed a minimal treatment temperature; moving the heating element within the hollow anatomical structure along a lengthwise direction of the hollow anatomical structure, and maintaining the heating element at or above the minimal treatment temperature while moving the heating element along the lengthwise direction.

In a variation of the method, the moving comprises moving the heating element without stopping along a treatment length of the hollow anatomical structure, the treatment length being greater than a length of the heating element.

In a variation of the method, the minimal treatment temperature is sufficient to cause durable reduction of the diameter of the hollow anatomical structure. In another variation of the method, the minimal treatment temperature is sufficient to cause absence of patency of the hollow anatomical structure.

In a variation of the method, the heating element is coupled to a shaft of a catheter.

A variation of the method further comprises delivering heated fluid from a tip of the catheter while moving the heating element. Another variation of the method further comprises passing the fluid through a lumen of the catheter and heating the fluid with the heating element as the fluid passes through the lumen before the fluid exits the catheter tip.

A variation of the method further comprises applying laser light to the hollow anatomical structure with the catheter.

In one embodiment, an apparatus for treating a hollow anatomical structure is disclosed that comprises: an elongate shaft; a therapeutic energy application device coupled to the shaft, the energy application device being sized for insertion into a hollow anatomical structure; and at least one visibility-enhancing element near the energy application device.

In a variation of the apparatus, the therapeutic energy application device is coupled to the shaft near a distal end of the shaft.

In another variation of the apparatus, the visibility-enhancing element is a light emitter. In a further variation, the light emitter is a visible light emitter. In a further variation, the light emitter is configured to direct light radially outward, away from a longitudinal axis of the shaft. In a further variation, a plurality of the light emitters are spaced radially apart around the longitudinal axis. In a further variation, the light emitter comprises an optical fiber connected to a light generator.

In another variation of the apparatus, the visibility-enhancing element is an ultrasound emitter. In a further variation, the visibility-enhancing element is a portion of the apparatus that is relatively highly reflective of ultrasound. In a further variation, the visibility-enhancing element comprises at least one gas bubble delivery port. In a further variation, the visibility-enhancing element is a portion of an outer surface of the shaft, which portion is configured to trap one or more gas bubbles.

In another variation of the apparatus, the visibility-enhancing element is a portion of the apparatus that is relatively highly radiopaque.

In another variation of the apparatus, the energy application device has a length greater than the width thereof.

In another variation of the apparatus, the energy application device is an electrically driven heater element. In a further variation, the electrically driven heater element is a closed circuit heating element.

In another variation of the apparatus, the visibility-enhancing element is configured to facilitate viewing a position of the energy application device within the hollow anatomical structure.

In another variation of the apparatus, at least one visibility-enhancing element comprises one visibility-enhancing element next to a proximal end of the energy application device, and another visibility-enhancing element next to a distal end thereof.

In another variation of the apparatus, the elongate shaft includes a plurality of longitudinally spaced index markings. In a further variation, the index markings are spaced apart by approximately a length of the energy application device.

In another embodiment, an apparatus for treating a hollow anatomical structure is disclosed that comprises: an elongate electrically driven heater that extends from a distal end thereof to a proximal end thereof; and a visibility-enhancing element adjacent to one of the proximal and distal ends.

In a variation of the apparatus, the visibility-enhancing element is configured to facilitate viewing a position of the electrically driven heater within the hollow anatomical structure. In a further variation, the visibility-enhancing element is a light emitter.

In another variation of the apparatus, the visibility-enhancing element is a portion of the apparatus that is relatively highly reflective of ultrasound. In a further variation, the visibility-enhancing element comprises a gas bubble delivery port adjacent to one of the proximal and distal ends.

In another variation of the apparatus, the heater is coupled to an elongate shaft having an outer surface, and the visibility-enhancing element is a portion of an outer surface of the shaft, which portion is configured to trap one or more gas bubbles.

In another variation of the apparatus, the visibility-enhancing element is a portion of the apparatus that is relatively highly radiopaque.

In another variation of the apparatus, the electrically driven heater has a length greater than the width thereof. In a further version, the electrically driven heater is a closed circuit heater.

In another embodiment, an apparatus for treating a hollow anatomical structure is disclosed that comprises: an elongate therapeutic energy source; a first visibility-enhancing element adjacent to a proximal end of the elongate therapeutic energy source; and a second visibility-enhancing element adjacent to a distal end of the elongate therapeutic energy source.

In a variation of the apparatus, the first and second visibility-enhancing elements are configured to facilitate viewing a position of the therapeutic energy source within the hollow anatomical structure. In a further variation, the first and second visibility-enhancing elements are light emitters. In a further variation, the first and second visibility-enhancing elements are ultrasound emitters. In a further variation, the first and second visibility-enhancing elements are portions of the apparatus that are relatively highly radiopaque.

In another variation of the apparatus, the therapeutic energy source has a length greater than the width thereof. In a further variation, the therapeutic energy source has a fixed profile in a plane orthogonal to a longitudinal axis of the therapeutic energy source.

In certain embodiments, systems and methods are disclosed for endovascular vein treatment using a catheter with an integrated heating element.

In one embodiment, a catheter comprises an elongate shaft and a resistive heating element located near the distal end of the elongate shaft. A temperature-sensing element is located in proximity to the resistive heating element and may be centered along the length of the heating element or may be offset from center. The resistive heating element may comprise a coil, and the coil may be of a constant pitch wind or of a varying pitch.

In one embodiment, a catheter comprises an elongate shaft and a resistive heating element located near the distal end of the elongate shaft. A sheath is slidably disposed on the shaft. The sheath and catheter are relatively movable between a first configuration, in which the sheath substantially covers the entire resistive heating element, and a second configuration in which the sheath covers less than the entire resistive heating element. The resistive heating element may comprise a coil, and the coil may be of a constant pitch or of a varying pitch. In certain embodiments, the sheath may have thermally-conductive and/or insulative properties in order to maintain a particular heat output along the heating element while the length of heat input to the HAS is reduced.

In one embodiment, a catheter system comprises an elongate shaft and an energy-emission element located near the distal end of the elongate shaft. The energy-emission element optionally includes a plurality of emission segments, and each of the segments is independently operable to emit energy into the surroundings of the energy-emission element. Optionally, the catheter system further comprises a power source drivingly connected to the emission segments. The power source is operable pursuant to a multiplexing algorithm to deliver power to, and operate, the emission segments in a multiplexed fashion. In one embodiment, the energy-emission element comprises a resistive element such as a resistive coil. In another embodiment, the energy-emission element comprises a radio frequency (RF) emitter.

In another embodiment, a catheter system comprises an elongate shaft and an energy-emission element located distal of the elongate shaft. The energy-emission element has an effective axial length along which the energy-emission element emits energy. In certain embodiments, the effective axial length of the energy-emission element is adjustable.

In another embodiment, a catheter comprises an elongate shaft and an expandable shaft located on a distal portion of the elongate shaft. A number of heater elements are expandable by a balloon. The heater elements may have a wavy, sinusoidal and/or serpentine configuration.

For purposes of summarizing the invention(s) disclosed herein, certain aspects, advantages and novel features of the invention(s) have been described herein. It is to be understood that not necessarily all such advantages may be achieved in accordance with any particular embodiment of the invention (s). Thus, the invention(s) may be embodied or carried out in a manner that achieves or optimizes one advantage or group of advantages as taught herein without necessarily achieving other advantages as may be taught or suggested herein.

BRIEF DESCRIPTION OF THE DRAWINGS

FIG. 7C illustrates two views of an embodiment of a catheter incorporating external fluid grooves and an external coil electrode.

FIG. 10A illustrates an embodiment of a working portion of a catheter body with individually expandable loops usable to treat a hollow anatomical structure.

FIGS. 10B-10D illustrate other embodiments of a working portion of a catheter body usable to treat a hollow anatomical structure.

FIG. 12A illustrates an embodiment of the working portion of a catheter having a conformable helical electrode axially coiled on a shaft.

FIG. 12B illustrates the electrode of the device of FIG. 12A being radially expanded by rotation of a distal catheter portion.

FIG. 12C illustrates the electrode of the device of FIG. 12B expanded and compressed distally to remove inter coil gaps.

FIG. 14 illustrates an exemplary embodiment of an indexing treatment system for hollow anatomical structures.

FIG. 15A illustrates an exemplary embodiment of a catheter having markings usable with an embodiment of an indexing treatment system for hollow anatomical structures.

FIG. 15B illustrates an exemplary embodiment of a catheter having markings and illumination holes usable with an indexing treatment system for hollow anatomical structures.

FIG. 16E illustrates another exemplary embodiment of a catheter usable with an embodiment of an indexing treatment system for hollow anatomical structures.

FIG. 16F illustrates a magnified view of an indexing portion of the catheter of FIG. 16E.

FIG. 16G illustrates another exemplary embodiment of a catheter usable with an embodiment of an indexing treatment system for hollow anatomical structures.

FIG. 16H illustrates exemplary embodiments of introducers usable with embodiments of an indexing treatment system for hollow anatomical structures.

FIGS. 21A-21D illustrates another exemplary embodiment of an indexing device usable for treatment of a hollow anatomical structure.

FIG. 23 illustrates an exemplary embodiment of an indexing system having a temperature sensor.

FIG. 24 illustrates an exemplary embodiment of an indexing system having multiple temperature sensors.

DETAILED DESCRIPTION OF THE PREFERRED EMBODIMENTS

The features of the systems and methods will now be described with reference to the drawings summarized above. The drawings, associated descriptions, and specific implementation are provided to illustrate embodiments of the invention(s) disclosed herein, and not to limit the scope of the disclosure.

In addition, methods and functions of treatment systems or devices described herein are not limited to any particular sequence, and the acts or blocks relating thereto can be performed in other sequences that are appropriate. For example, described acts or blocks may be performed in an order other than that specifically disclosed, or multiple acts or blocks may be combined in a single act or block.

Figure 1:
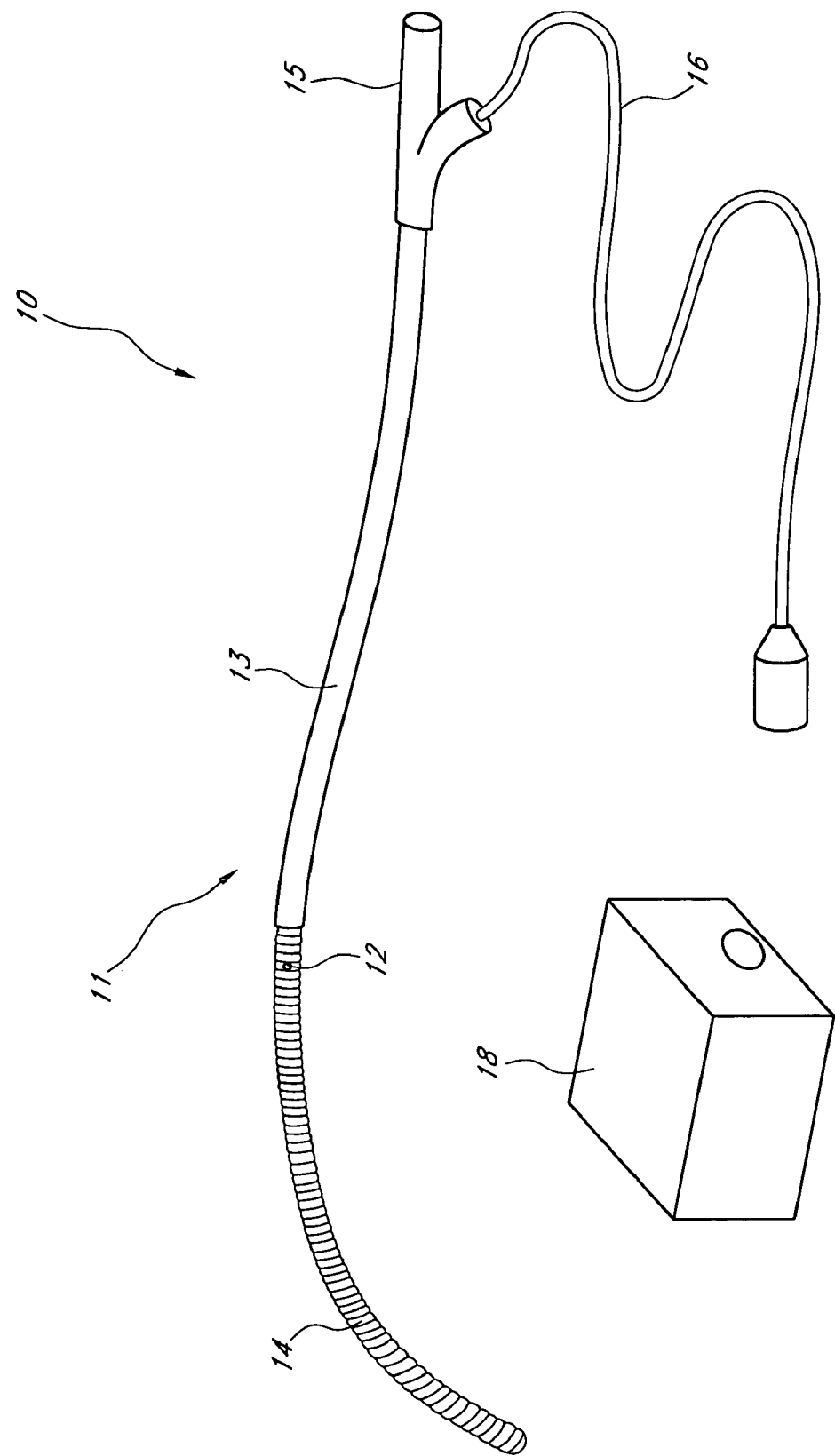
FIG. 1 illustrates an overall view of a resistive element system usable to treat a hollow anatomical structure.

FIG. 1 illustrates an embodiment of a resistive element system 10 for applying energy to a hollow anatomical structure (HAS) (e.g., the wall of the HAS). For example, a HAS may include, but is not limited to, a vein, such as a greater saphenous vein, a short saphenous vein, a tributary vein, a perforator vein, a varicose vein, or the like. As illustrated, the resistive element system 10 comprises a catheter 11. The catheter 11 includes a catheter shaft 13, which may be used to maneuver a distal portion 14 of the catheter 11 into a desired placement within the HAS. In certain embodiments, the catheter shaft 13 comprises a biocompatible material having a low coefficient of friction. For example, the shaft 13 may comprise PEEK, Polyethylene or TEFLON®. In other embodiments, the shaft 13 may comprise Polyimide, HYTREL®, PEBAX®, nylon or any other such suitable material.

In certain embodiments, the catheter shaft 13 is sized to fit within a vascular structure that may be between approximately one millimeter and approximately twenty-five millimeters in diameter and, preferably, between approximately two millimeters and approximately 18 millimeters. For instance, the catheter shaft 13 may have a maximum outer diameter of between approximately four French and approximately eight French and, more preferably, between approximately six French and approximately seven French. In yet other embodiments, other sizes of catheters may be used. In certain embodiments, the distal portion 14 transfers energy (e.g., heat) directly to an inner wall of a HAS. The proximal end of the catheter has a handle 15. In certain embodiments, the handle 15 may include a connection 16 for interfacing with an energy source 18 and a port for fluid or guidewire passage (e.g., a 0.014", 0.018", 0.035" or preferably a 0.025" guidewire).

In certain embodiments, the energy source 18 comprises an alternating current (AC) source, such as an RF generator. In other embodiments, the energy source 18 comprises a direct current (DC) power supply, such as, for example, a battery, a capacitor, or other energy source such as would be used for microwave heating. The energy source 18 may also incorporate a controller that, through the use of a processor, applies power based at least upon readings from a temperature sensor 12 or sensors (e.g., a thermocouple, a thermistor, a resistance temperature device, an optical or infrared sensor, combinations of the same or the like) located in the working portion (e.g., therapeutic portion) of the catheter 11. For example, the controller may heat the tissue of a HAS or the therapeutic region of the catheter to a set temperature. In an alternative embodiment, the user selects a constant power output of the energy source 18. For example, the user may manually adjust the power output relative to the temperature display from the temperature sensor 12 in the working portion of the catheter 11.

FIG. 1 thus illustrates one embodiment of a hollow anatomical structure therapy system. The system comprises an energy application device suitable for insertion into a hollow anatomical structure; a power source in communication with the energy application device, the power source comprising a processor and program instructions executable by the processor such that the power source is operable to: (a) deliver power to the energy application device during a first power delivery phase; (b) measure time elapsing during power delivery; (c) assess performance of the therapy system during the first power delivery phase; and (d) if the performance of the therapy system during the first power delivery phase is satisfactory, deliver power to the energy application device during a second power delivery phase.

In variations of this system, the energy application device may be an electrically driven heating element, an electrode, or a laser. The electrically driven heating element may comprise a coil or any other heating element structure known in the art, and is provided with an energy coupling surface for applying energy to the hollow anatomical structure being treated. In a further variation, the distal-to-proximal length of the heating element along the energy coupling surface is at least fifteen times the width of the heating element. The electrode may be any electrode known in the art suitable for applying energy to a hollow anatomical structure. Furthermore, the laser employed may be any laser known in the art to be suitable for applying energy to a hollow anatomical structure.

In further variations of the system, the energy application device may be coupled to the shaft of a catheter suitable for insertion into a hollow anatomical structure such as a vein to facilitate the placement of the energy application device within the hollow anatomical structure. Conventional catheters sized to access small vasculature that are known in the art may be employed for this purpose.

In other variations of the therapy system, the system may also comprise a temperature sensor configured to sense either or both of (i) a temperature of at least a portion of the energy application device, and (ii) a temperature of tissue in thermal communication with said energy application device. The temperature sensor may comprise a thermocouple, a thermistor, a resistive temperature device (RTD) or a set of contacts that measures resistance. FIG. 1 shows an example of this in which the temperature sensor 12 is placed at the distal portion 14 of the catheter 11.

In other variations of the system, the program instructions are executable by the processor such that the power source is further operable to: deliver power to the energy application device to reach a first treatment temperature; and deliver power to the energy application device to reach a subsequent second treatment temperature which is lower than the first treatment temperature. The program instructions may also be executable by said processor such that the power source is further operable to determine expiration of the first power delivery phase based on temperature measurement results obtained by the temperature sensor. In one variation, the first power delivery phase is 10 seconds or less in duration. In a further variation, the program instructions are executable by the processor such that the power source is further operable to determine expiration of the first power delivery phase when the temperature sensor senses a target temperature within a time limit.

In further variations of the system, satisfactory performance of the therapy system comprises reaching or exceeding a target temperature within a time limit. In further variations, the program instructions are executable by the processor such that the power source proceeds to the second power delivery phase only when the temperature sensor senses the target temperature within the time limit. In one variation, the time limit is six seconds or less. In a further variation, the target temperature is approximately 120 degrees Celsius.

In other variations, the combined duration of the first power delivery phase and the second power delivery phase is 60 seconds or less.

In other embodiments, the hollow anatomical structure therapy system comprises: a heat delivery device suitable for insertion into a hollow anatomical structure; a power source in communication with said heat delivery device, the power source being programmed to: (a) deliver power to the heat delivery device during a temperature ramp-up phase; (b) measure time elapsing during power delivery; (c) monitor operation of the heat delivery device; and (d) if the operation of the heat delivery device either during or shortly after the temperature ramp-up phase is acceptable, deliver power to the heat delivery device after the temperature ramp-up phase.

In further variations, the heat delivery device is selected from the group consisting of an electrically driven heating element, an electrode, and a laser. When the heat delivery device comprises an electrically driven heating element, the heating element may be provided with an energy coupling surface having a distal-to-proximal length which is at least fifteen times the width of the heating element.

In further variations, the system is provided with a catheter having a shaft to which the heat delivery device is coupled.

In further variations, the system is provided with a temperature sensor configured to sense at least one of (i) the temperature of a portion of the heat delivery device, and (ii) the temperature of tissue in thermal communication with the heat delivery device.

In further variations of the system, acceptable operation of the heat delivery device during or shortly after said temperature ramp-up phase comprises reaching or exceeding a target temperature within a time limit. In other variations, acceptable operation of said heat delivery device during or shortly after the temperature ramp-up phase comprises falling below a target temperature within a time limit. In another variation, the combined duration of the temperature ramp-up phase and a subsequent power delivery phase is 60 seconds or less.

In another variation, the power source is further programmed to: deliver power to the heat delivery device to reach a first treatment temperature; and deliver power to the heat delivery device to reach a subsequent second treatment temperature which is lower than the first treatment temperature.

For example, in certain preferred embodiments, the energy source 18 may comprise an RFGPluS™ RF generator supplied by VNUS Medical Technologies, Inc. (San Jose, Calif.). In other embodiments, the energy source 18 may comprise other types of RF or energy-delivering generators usable to power the working portion of the catheter 11. For example, details of RF generators that may be used with the embodiments of the catheters disclosed herein are further disclosed in the following patents, the entirety of each of which is hereby incorporated herein by reference to be considered part of this specification: U.S. Pat. No. 6,071,277, issued Jun. 6, 2000; U.S. Pat. No. 6,152,899, issued Nov. 28, 2000; U.S. Pat. No. 6,165,172, issued Dec. 26, 2000; U.S. Pat. No. 6,179,832, issued Jan. 30, 2001; U.S. Pat. No. 6,200,312, issued Mar. 13, 2001; U.S. Pat. No. 6,237,606, issued May 29, 2001; U.S. Pat. No. 6,258,084, issued Jul. 10, 2001; U.S. Pat. No. 6,322,559, issued Nov. 27, 2001; U.S. Pat. No. 6,401,719, issued Jun. 11, 2002; U.S. Pat. No. 6,638,273, issued Oct. 28, 2003; U.S. Pat. No. 6,752,803, issued Jun. 22, 2004; and U.S. Pat. No. 6,769,433, issued Aug. 3, 2004.

Figure 2:
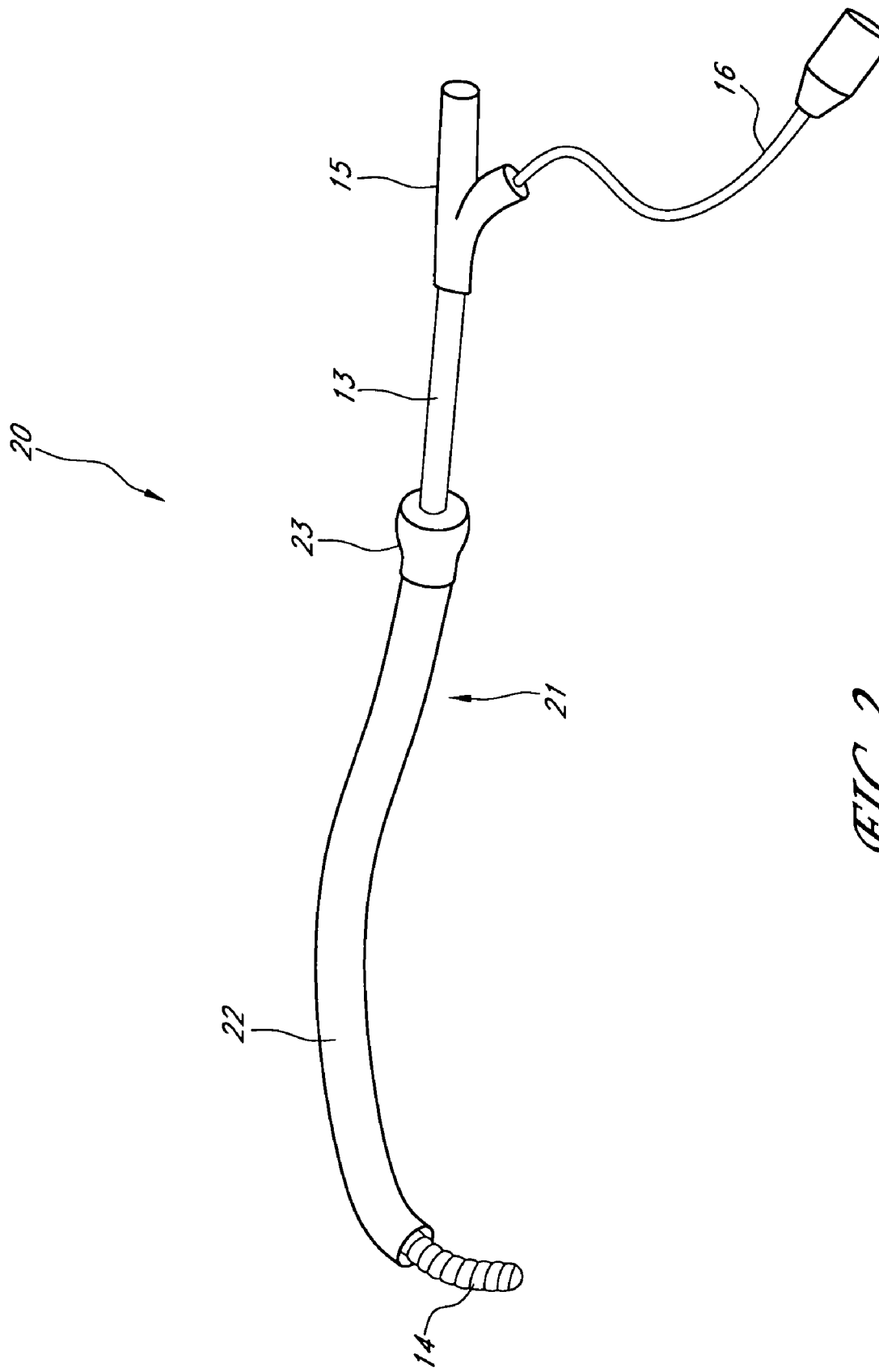
FIG. 2 illustrates one embodiment of a catheter sheath in a partially retracted position usable with the resistive element system of FIG. 1.

FIG. 2 illustrates another embodiment of a resistive element system 20. As shown, a catheter 21 includes an outer retractable sheath 22. The sheath 22 is advantageously used to protect the device during placement, facilitate introduction of the device, and/or adjust the exposed axial length of the resistive element 14 (i.e., therapeutic element) for a user-selected and/or variable treatment length. For example, the sheath 22 may be used (e.g., pulled back (proximally) or pushed forward (distally)) to adjust the length of the heated region of the resistive element 14 that is exposed to a wall of the HAS. In certain embodiments, the sheath may comprise a material or materials that insulates the inner wall of the HAS from receiving thermal energy above a therapeutic temperature and/or that conducts thermal energy away from the resistive element to reduce build-up of heat surrounding the portion of the resistive element that is covered by the sheath.

FIG. 2 further shows an optional sensor 23 coupled to the sheath 22 and the shaft 13. In other embodiments, multiple sensors are placed along the axial resistive element length. For example, an energy source may advantageously monitor the individual sensors and use data received therefrom for temperature feedback. In another embodiment, a controller may monitor for high temperature or low temperature signals. For example, an algorithmic process may be used to control the current applied to the various wire coils, thus maintaining a substantially axially-uniform temperature and/or heat output.

Figure 3:
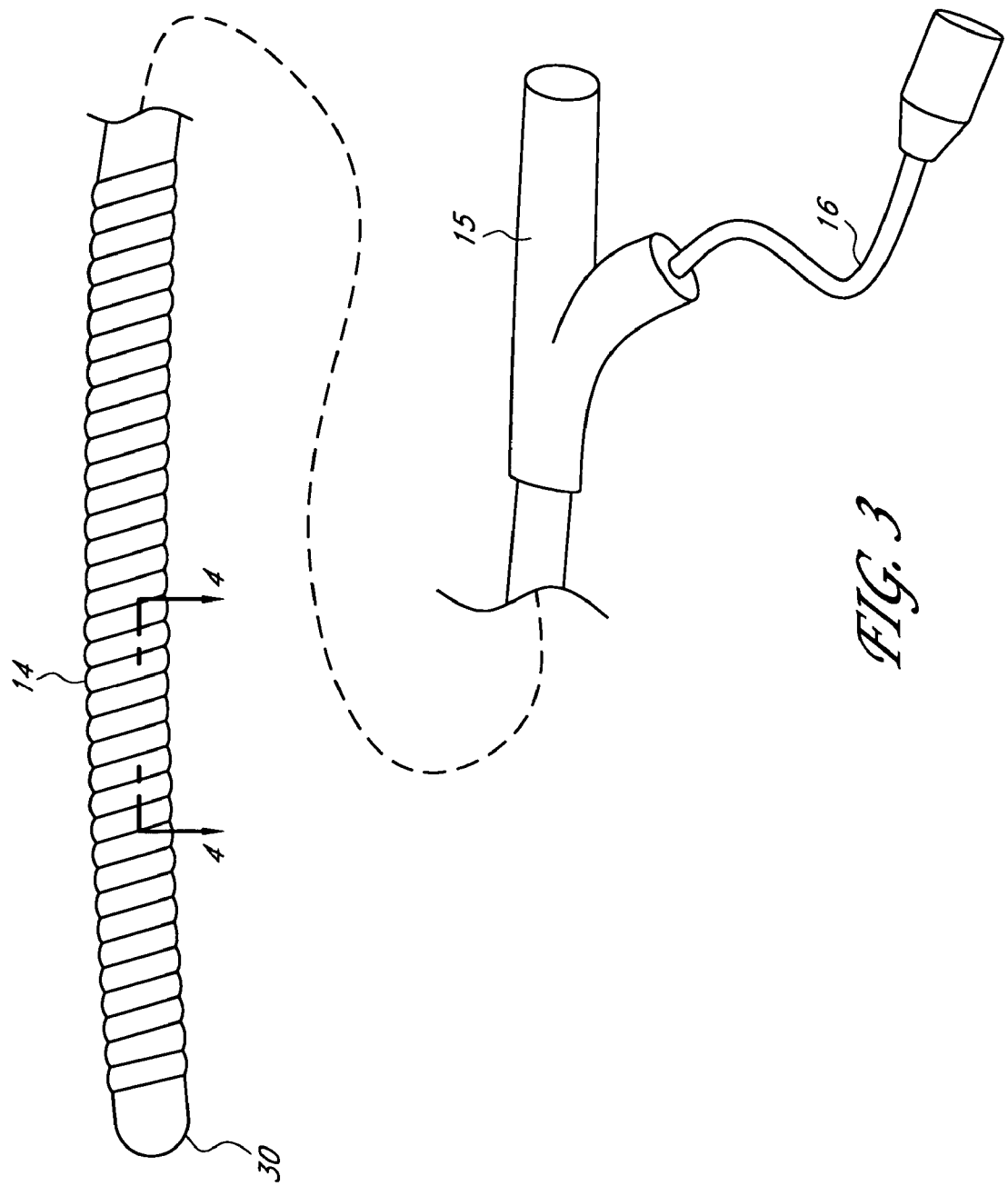
FIG. 3 illustrates a magnified view of an exemplary embodiment of a therapeutic element of a catheter usable with the resistive element system of FIG. 1.
Figure 4:
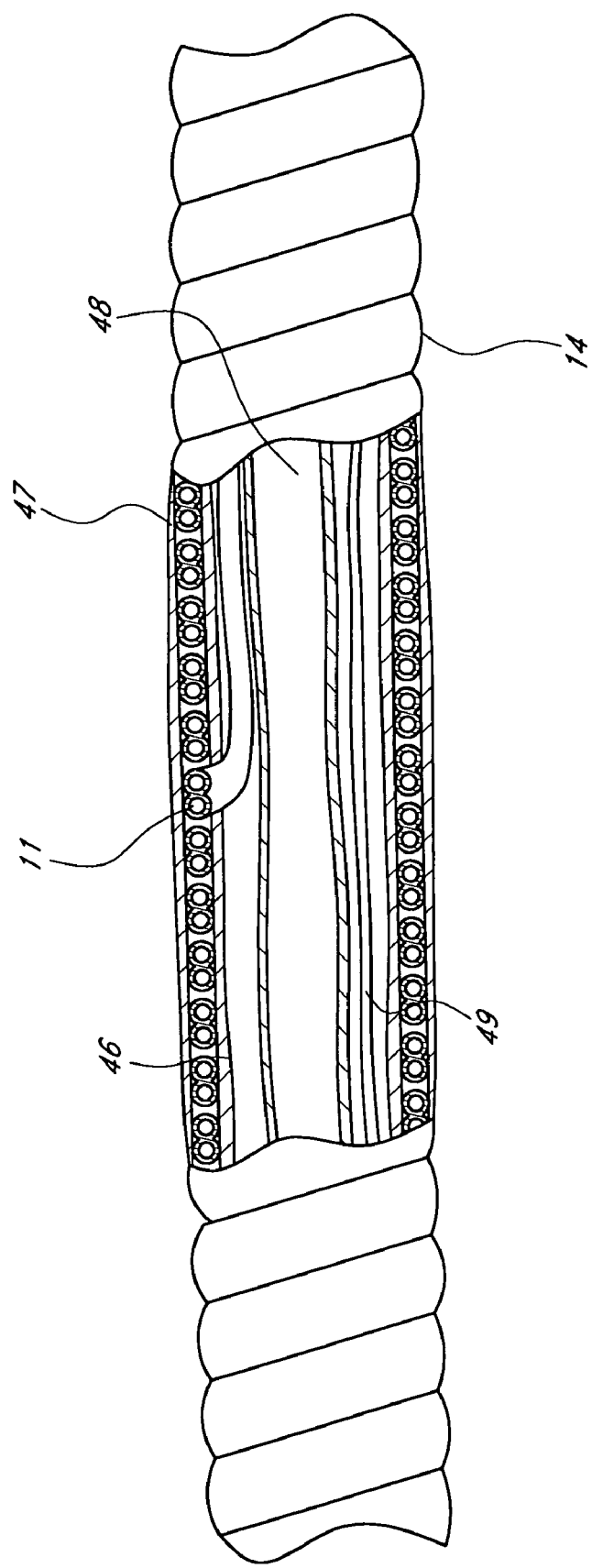
FIG. 4 illustrates a cross-sectional side view of the therapeutic element (i.e., working end) of the catheter of FIG. 3.

FIG. 3 illustrates a catheter with a cross-section 4-4 of the resistive element 14, which is further depicted in FIG. 4. In one embodiment, a thermally-conductive tip 30 or extension near the tip is used to extend heating toward the distal tip of the catheter. In certain embodiments, optional features at or near the distal tip and/or the proximal end of the heating coil may assist in ultrasound visibility (e.g., a rough surface such as caused by grit-blasting, or slots, holes or fins). FIG. 4 illustrates a detailed cross-sectional portion of the resistive element 14 and internal components of the catheter. As will be appreciated, the distance between the illustrated adjacent coils of the resistive element 14 may be of consistent or varied spacing.

The distal section of the catheter in FIG. 4 shows the resistive element 14 covered by a sleeve 47. In one embodiment, the sleeve 47 is a thin-walled tube from approximately 0.002 inch to approximately 0.010 inch thick. In other embodiments, the sleeve 47 may have a wall thickness of less than 0.00025 inch or of more than 0.003 inch. In one embodiment, the sleeve 47 comprises a non-stick material such as TEFLON® (FEP, PTFE) and/or a non-stick coating such as silicone or a hydrogel. In other embodiments, the sleeve 47 may comprise PET (polyethylene terephthalate), polyimide or other thin-walled sleeve material that remains substantially stable and resists damage at temperatures well above the desired temperature range. The sleeve material may also be preferably chosen to provide uniformity of heating along the full length of the heating coil, with a defined temperature offset (e.g., a predictable gradient between the heating coil within the sleeve and the outer diameter which is in contact with the HAS). The material selection process of sleeve 47 may be determined by using polymers with nonconductive or electrically insulative properties. In certain embodiments, it may be desirable to maintain a property of the catheter surface that gives the user tactile feedback of HAS shrinkage after treatment (such as, for example, a detectable slight friction).

FIG. 4 also shows an internal lumen 48 of the catheter, which communicates through an open lumen, such as from a distal tip to a proximal handle. In one embodiment, the lumen 48 is used for delivery of fluids, such as for example, saline, a venoconstrictor, sclerosant, high-impedance fluid, physiologic tissue adhesive, hydrogel, combinations of the same or the like. In addition, upon completion of treatment, a sclerosant and/or a hydrogel may be exuded from the distal catheter end, allowing for substantially complete vessel occlusion. For example, the hydrogel may be biocompatible or bioresorbable. In other embodiments, the hydrogel may be displaced by the constriction of the HAS resulting from the thermal injury response, which results in substantially complete occlusion. In those sections of the HAS in which the fluid material has not completely compressed the HAS wall, the fluid material may be naturally resorbed by the body.

In yet other embodiments, the lumen 48 may also accommodate a guide wire for catheter placement. In certain embodiments, the lumen 48 may accommodate an optical fiber for additional laser energy delivery and/or to provide guiding illumination to indicate the location of the distal end of the catheter as transmitted and visualized through tissue. In yet other embodiments, the lumen 48 may be of the Rapid Exchange variety to allow a guidewire to pass through a distal portion of the catheter shaft.

In certain embodiments, the resistive element 14 of the catheter is made of resistive wire that generates heat when an energy source (e.g., energy source 18 of FIG. 1) is connected and applied thereto. As shown in FIG. 4, the resistive element 14 comprises a wire having a round cross-section, wound on top of an inner shaft layer or layers 46. In particular, the resistive element 14 may comprise a round bifilar wire having an insulative layer that holds wires together. In certain embodiments, the insulative layer preferably comprises a polyimide or like material. In certain preferred embodiments, a spacing of approximately one-half the wire diameter exists between the insulative layers of adjacent bifilar wires. As shown in FIG. 4, a temperature sensor 11, such as a thermocouple, is incorporated into the resistive element by being located within a suitable gap between coil windings.

In other embodiments, the cross-section of the resistive element 14 may alternatively be oval, rectangular, or another geometrical cross-section. Preferably, the relative resistance or impedance of the resistive element 14 is designed to correlate to, or match, the energy source. For example, the resistance of resistive element 14 may be determined by a wire gage that relates to the catheter diameter, the energy required during treatment, and/or the energy source specifications. The resistive element 14 may comprise a wide variety of conductive materials, such as, for example, nickel chromium (NICHROME®), Alloy 52, copper, stainless steel, titanium, zirconium, NITINOL®, ALUMEL®, KANTHANAL®, CHROMEL®, KOVAR®, combinations or alloys of the same and the like. The material for the resistive coil or resistive element 14 can be chosen to provide Resistance Temperature Detector (RTD) functionality, wherein temperature is indirectly measured as a function of impedance. Alloy 52 is considered to be one material suitable for providing RTD functionality to the resistive element 14.

The resistive element 14 illustrated in FIG. 4 is nearly a close-pitch (or closed-wind) coil (i.e., with very little inter-coil spacing). In one embodiment, an electrical connection, such as soldering at the proximal end and/or the distal end of the coil, couples the resistive element 14 to signal wires 49. As shown in FIG. 4, the signal wires 49 are coupled at the distal end of the resistance coil. For example, the signal wire 49 may connect at the distal end of the resistive element 14 and run internally the length of the catheter to a connector cable. In one embodiment, the signal wires 49 extend from the proximal end of the coil. In such an embodiment, the signal wire 49 is preferably a larger gage copper wire (e.g., 28 to 34 gage) to reduce possible heating within the main body of the catheter.

The radially outwardly disposed portions of the resistive element 14 function as an energy coupling surface which extends generally along the length of the resistive element. When the resistive element 14 comprises a coil, the energy coupling surface typically comprises the (roughly) cylindrical outer surface of the coil, and extends from the proximal edge of the coil to the distal edge thereof. In this example, the cylinder comprises an energy-coupling surface in that substantially the entire cylinder becomes heated and transfers heat to the surrounding portions of the HAS in a typical treatment. Where additional, highly thermally conductive portions are positioned longitudinally adjacent to the coil, these outer surfaces of these portions can be considered part of the energy coupling surface, if the adjacent portions reach a treatment temperature during normal operation of the coil. Thus, for coil-type resistive elements, the energy coupling surface extends along the entire active portion of the coil, and along any thermally active portions adjacent to the coil. Where the catheter includes a coating (such as a lubricious coating) over the coil, the outer surface of the coating can be considered an energy coupling surface, as heat transfer to the HAS will take place where portions of the HAS contact (or are otherwise in thermal communication with) the outer surface of the coating.

When in the form of a resistive heating coil, the resistive element 14 generates heat internally, within the winds of the coil, and transfers heat radially outwardly to the HAS from the central longitudinal axis of the coil/catheter. The heat is transferred via the energy coupling surface (whether the outer coil surface itself or a coating forms the energy coupling surface) to the inner wall of the HAS, either through direct contact and conduction, or through intervening media, such as fluids, etc.

In one embodiment, the resistive element 14 comprises a constant, closed-pitch coil. Alternatively, the resistive element 14 may have a varying pitch and/or a varying inter-coil spacing. For example, a varying coil pitch and/or spacing may be advantageously used to vary the heat output over the axial length of the resistive element 14. An axially (and/or radially) varying heat output from the resistive element 14 may be useful in providing a substantially uniform tissue and/or device temperature during treatment.

For example, such a variation in coil pitch may be advantageous in situations involving fluid flow within the HAS. In such embodiments, wherein fluid runs from the direction of the proximal end of the catheter towards the distal end of the catheter, fluid tends to absorb heat output from the proximal portion of the resistive element 14 to a greater degree than heat output from the distal portion. Such may result in a reduction of the heat actually applied to the wall of the HAS adjacent to the proximal portion of the resistive element 14 relative to the central and distal sections. As the fluid flows past the proximal section of the resistive element 14, the fluid itself is heated. The heated fluid then flows across the middle and distal sections of the resistive element 14, thereby increasing the temperature of treatment for these sections. Furthermore, a tighter wind pitch at the ends of the resistance element 14 may balance any edge-effect heating losses that may otherwise cause a drop in heat intensity at the ends of the resistance element 14.

Certain embodiments, intended to counteract this uneven heat distribution, comprise a close-pitch wind of the resistive element 14 in the proximal portion (providing a higher heat output in the proximal portion), while the middle and distal sections have a comparatively more open-pitch wind (i.e., the inter-coil spacing increases in the distal direction). This configuration advantageously decreases the heat output along portions of the coil in order to compensate for the added heat from the proximal adjacent sections. That is, the variable coil pitch may be used to correct for higher temperatures of the middle sections of the resistive element 14 in comparison with lower temperatures of the end sections of the resistive element 14. A thermally-insulating material (such as natural rubber, silicone, or an elastomer) may also be used to shield the internal lumen 48 from heating and/or to selectively reduce external heat transfer from the resistive element 14.

In another embodiment, portions of the resistive element 14 having a close-pitch wind are used to heat larger portions of a HAS (e.g., portions having a larger diameter) while portions of the resistive element 14 having an increased coil spacing are used to heat smaller portions of the HAS (e.g., portions having a smaller diameter).

Figure 5:
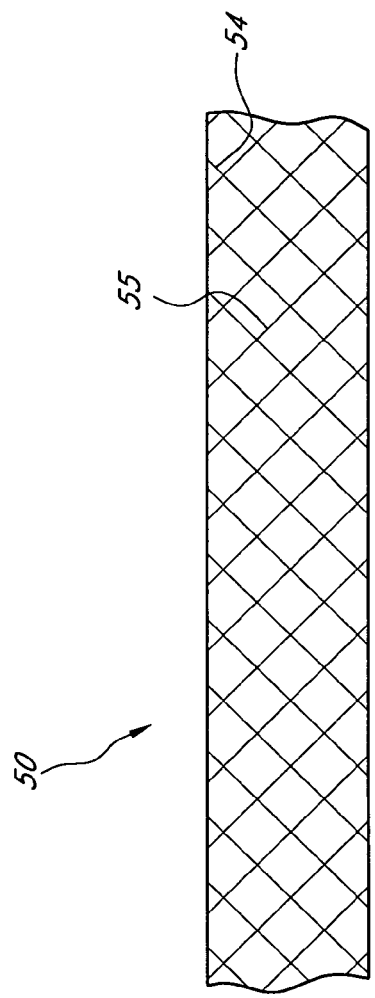
FIG. 5 illustrates a side view of another embodiment of a working end of the catheter of FIG. 3.

In other embodiments, the coil wind comprises more than one radially displaced layer. For example, as shown in FIG. 5, a resistive element 50 advantageously comprises two layers 54 and 55 of winds that are counter-wound to overlap. These layers 54 and 55 may also have a variable pitch over the axial length of the catheter shaft. Such a configuration may be used to provide a greater heating density and/or to provide more uniform heating if the coil winds are spaced to increase the length of the heating segment while using a limited length of coil wire.

Figure 6:
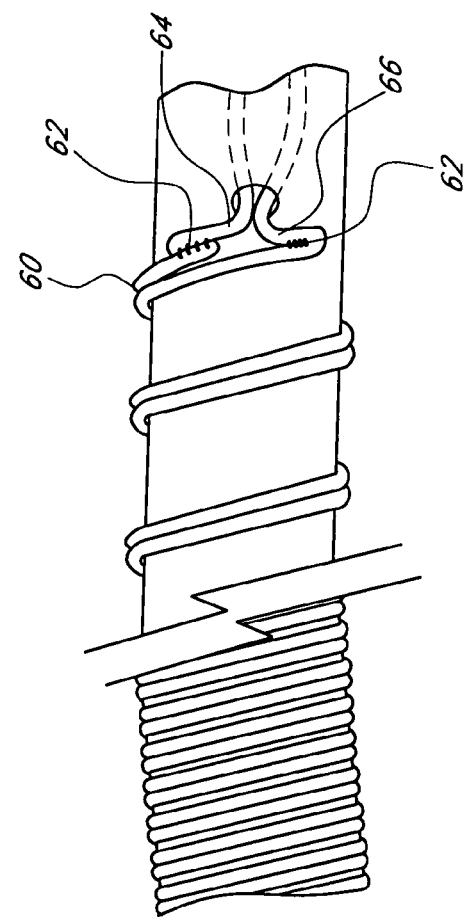
FIG. 6 illustrates a side view of yet another embodiment of a working end of the catheter of FIG. 3.

In the embodiment shown in FIG. 6, the resistive element comprises a bifilar wire coil, which is advantageous in processing since it can be wound as a single filament. A bifilar wire also maintains a substantially constant distance between the two embedded wires, which can help to maintain accurate overall spacing in order to provide uniform heat distribution. In some embodiments, the wind of the bifilar wire coil may comprise a variable pitch, as discussed previously. In certain embodiments, the bifilar wire coil may also combine wire connections (i.e., connections between the multiple wires in the wire coil) at one end of the catheter, such as the proximal end. In certain embodiments, for example, the distal end may also comprise an electrical connection between the two wire ends in order to create a continuous loop. In alternative embodiments, the bifilar wire may comprise more than two wires.

FIG. 6 shows a bifilar wire 60 coupled through solder joints 62 to signal wires 64 and 66. In certain embodiments, the joints 62 are spot welded or bonded with a conductive epoxy. In addition, the signal wires 64 and 66 may extend internally through the catheter shaft to a connector located at the proximal end (e.g., connector 16 of FIG. 1). FIG. 6 further shows one example of a variable wind configuration, as discussed previously.

In other embodiments, energy is applied separately to each wire of the bifilar wire coil. For example, applying energy separately to each wire may be used to vary and control the power and heat transferred from the device to the HAS. In one embodiment, a single coil is used for a relatively smaller HAS, while a plurality of coils are used with a relatively larger HAS.

Figure 7A:
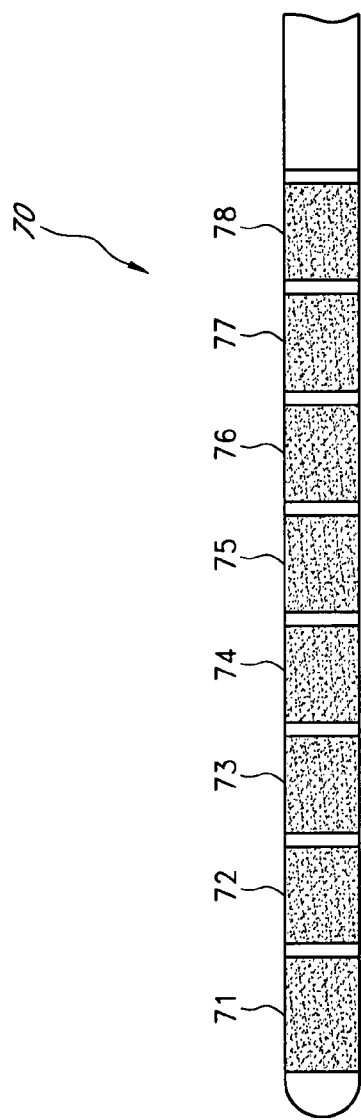
FIG. 7A illustrates a side view of yet another embodiment of a working end of the catheter of FIG. 3, wherein the working end comprises multiple treatment segments.

In another embodiment, as shown in FIG. 7A, a resistive element 70 comprises multiple coils or electrodes, which are sequentially placed axially on the catheter shaft. For example, FIG. 7A illustrates the resistive element 70 including eight such coils, which are identified as elements 71-78. In certain embodiments, each resistive element 71-78 may be individually temperature controlled and/or may comprise a temperature sensor. Alternatively, the resistive elements 71-78 may be used in a power control mode that relies on manual energy control.

Alternatively, in embodiments having multiple resistive elements, a temperature sensor is located on the most distal resistive element (e.g., element 71) or other resistive element. For example, the most distal resistive element may be used for the initial treatment, and the successive coil electrodes may use the same and/or a predetermined energy-time profile.

In certain embodiments, a method of use of the resistive element 70 includes multiplexing through each of the resistive elements 71-78 shown in FIG. 7A. The term "multiplex" as used herein is a broad term and is used in its ordinary sense and includes, without limitation, the energizing or heating of at least one resistive element for a specific dwell time and cascading, or moving, to another resistive element until a final resistive element is reached or until a cycle is completed. In certain embodiments, the cycle may then be repeated until the complete treatment time is reached.

Figure 7B:
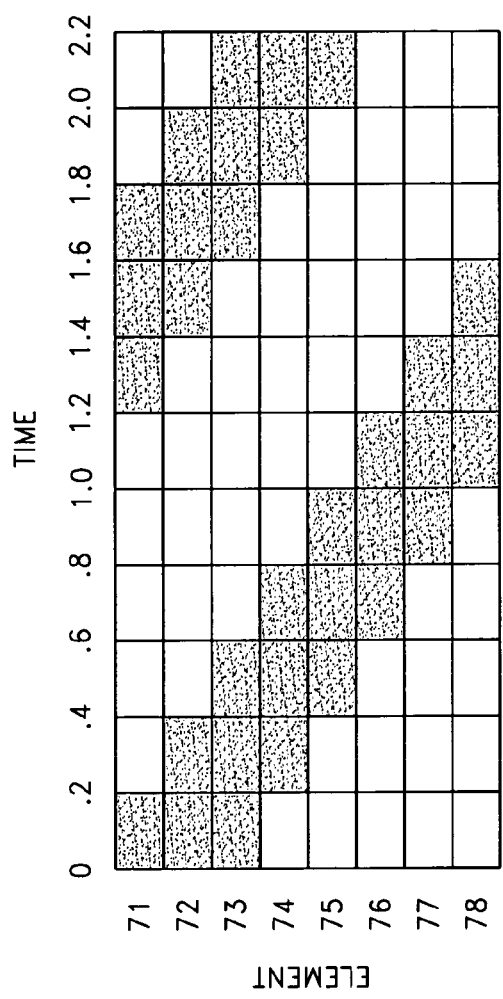
FIG. 7B is a table depicting an exemplary treatment cycle usable with multiplexing the treatment segments of the catheter of FIG. 7A.

FIG. 7B depicts a table illustrating the use of the resistive element configuration 70 shown in FIG. 7A. In one embodiment, the resistive elements 71 through 78 are sequentially energized for a dwell time of approximately 0.2 second. In the example shown, three resistive elements are powered at one time. In particular, the table has shaded blocks of time that represent the time that energy is delivered to the specified resistive elements. Since three resistive elements are powered at one time, and the dwell time is 0.2 second, each resistive element is on for a total of approximately 0.6 second during one cycle. As illustrated by the table, for time 0 to time 0.2 second, resistive elements 71, 72 and 73 are energized. For time 0.2 second to 0.4 second, resistive elements 72, 73 and 74 are energized. This process repeats by stepping through the resistive element set. For the eight resistive elements shown, one complete cycle takes approximately 1.6 seconds.

In one embodiment, to avoid overcooling a particular resistive element, the cycle time is of a shorter duration and/or the total number of resistive elements is limited. That is, in certain embodiments, a resistive element may be re-energized before substantial cooling takes place. In addition, in one embodiment, to increase the treatment zone the catheter may comprise multiple treatment zones, such as for example, groups of eight resistive elements. Each group of eight resistive elements may treat the wall of the HAS before energy is applied to the next group of resistive elements. Alternative modes of multiplexing may also be employed. For example, the number of adjacent resistive elements simultaneously energized may vary. Also, the entire cycle may re-start at the first energized resistive element or the most recent energized resistive element. Another mode of multiplexing may be accomplished while sensing the tissue impedance. Once a certain impedance level is achieved, the next set of resistive elements is then energized.

Alternatively, at least one of the eight resistive elements 71-78 is energized to treat the HAS until treatment is complete. Then, the next resistive element(s) apply heat for a similar treatment time, and so on, moving along the treatment zone. For the eight resistive elements 71-78 illustrated in FIG. 7A, the treatment may be for one cycle. For example, resistive element 71 may treat the HAS for approximately 20 seconds. Once resistive element 71 has completed treatment, resistive element 72 repeats the treatment for the same treatment time and energy settings. Such a process may continue for resistive elements 73 through 78.

In other embodiments, other treatment cycles may be used. For example, resistive elements 71 and 72 may concurrently treat the HAS for approximately 20 seconds. Then resistive elements 73 and 74 may apply a similar treatment, and so forth, through resistive elements 77 and 78 to complete the cycle.

FIG. 7C illustrates an embodiment of an electrically resistive heating element 80 having an open pitch wind, but omitting the depiction of an outer sleeve. In particular, FIG. 7C shows a coil spacing greatly exaggerated in order to see details of a catheter tube 82. In one embodiment, the inter-coil spacing is selected to create a path for fluids. For example, an inner lumen 84 (which is shown as a single lumen, but may include multiple lumens) of the catheter may deliver fluid to a HAS by pathways 86, which are external surface features and radial holes (intermittently spaced along the grooves) in the tube 82 wall. The fluid may be a saline, a venoconstrictor or the like. In one method for using the device 80 of FIG. 7C, the device 80 is placed in the HAS. The HAS is then treated with a venoconstrictor via the catheter lumen 84 and the pathways 86. The HAS is then treated by heating the constricted wall of the HAS.

Figure 7D:
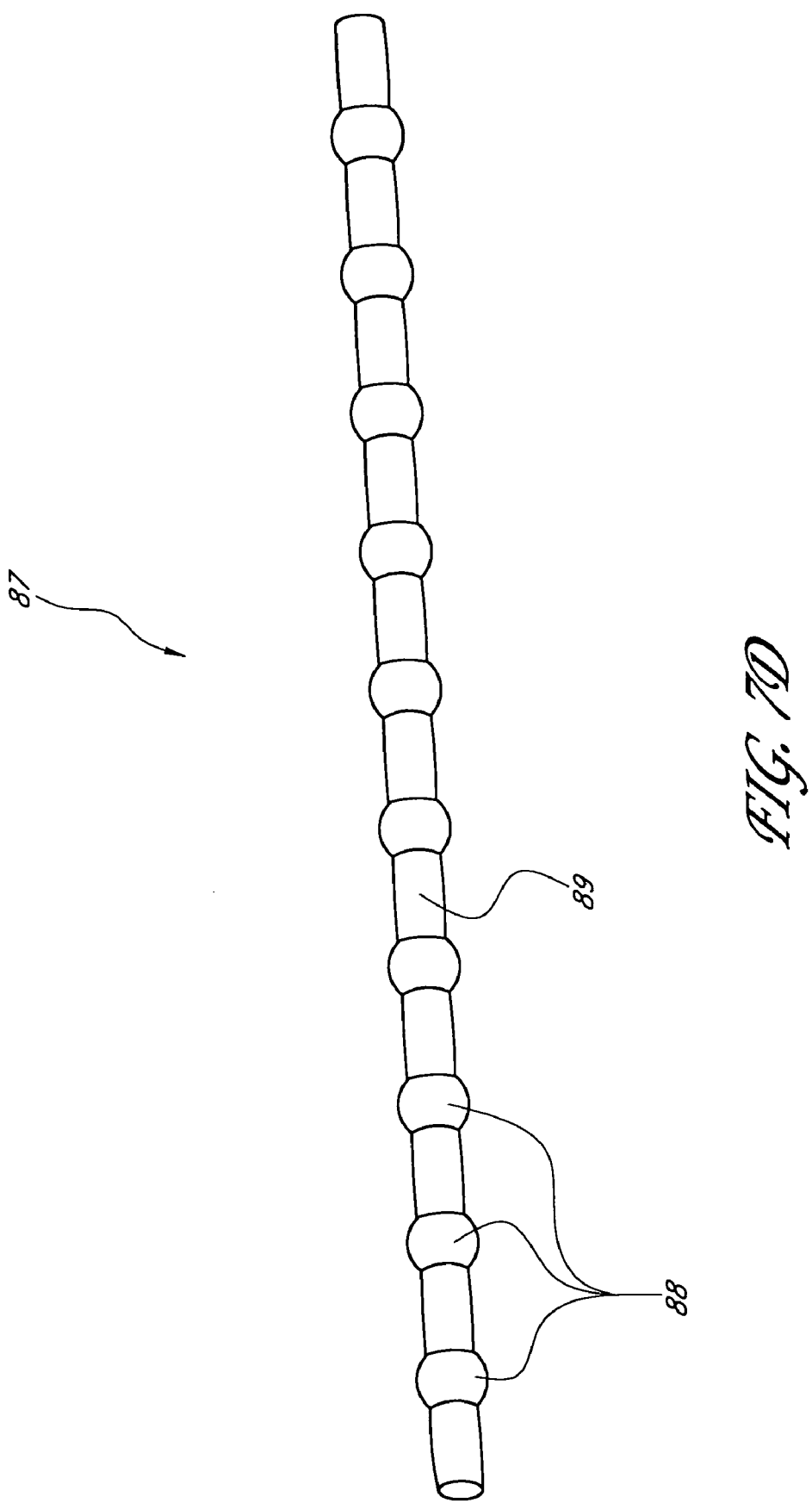
FIG. 7D illustrates an embodiment of a resistive element system having multiple protruding resistive elements.

FIG. 7D illustrates an embodiment of a resistive heating element 87 having separate and distinct protruding resistive elements 88 made of resistive materials, such as, for example, KANTHANAL®, NICHROME®, CHROMEL®, ALUMEL®, KOVAR®, Alloy 52, titanium, zirconium, combinations or alloys of the same or the like. In certain embodiments, a series of resistive elements 88 is spaced axially along a catheter shaft 89, wherein each of the resistive elements 88 comprises a doubly-truncated-spherical body. In one embodiment, each resistive element 88 may be further attached to a signal wire by solder, spot weld or other like method. For example, the signal wire may run internal to the catheter shaft 89 and attach to a cable and/or a connector.

Figure 7E:
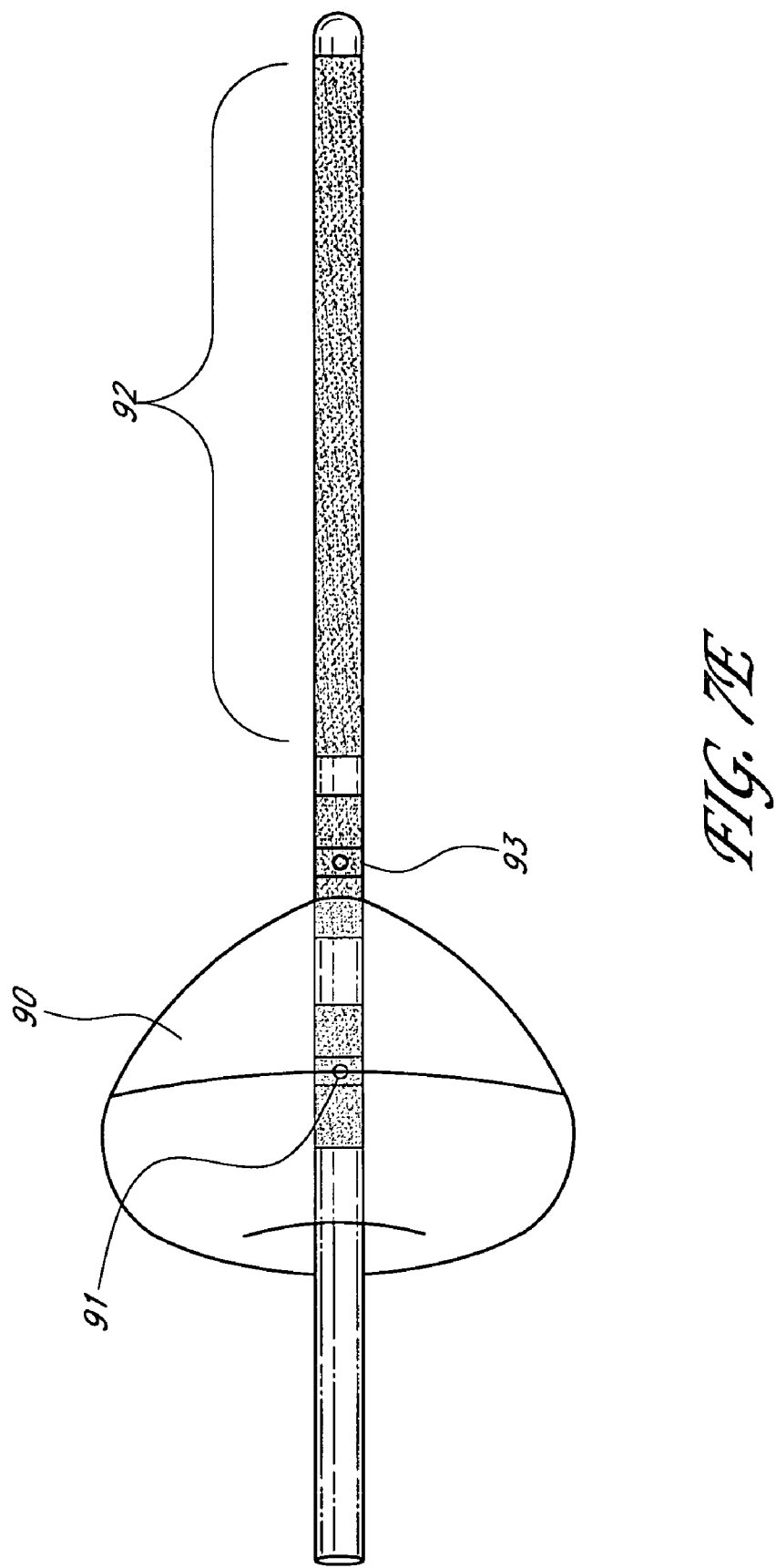
FIG. 7E illustrates a side view of a resistive element system including an expandable balloon and a set of fluid ports.

FIG. 7E illustrates another example of a working portion of a catheter according to certain embodiments. The device shown has the addition of a balloon 90 expanded by at least one port 91. As shown, the balloon 90 is located proximate to a resistive element 92. The balloon 90 may be used in conjunction with the resistive element 92 to occlude or substantially occlude a HAS. At least one additional fluid port 93 proximal to the resistive element 92 may also be used for fluid placement within the HAS.

In one embodiment, the catheter is placed in the HAS, and then the balloon 90 is inflated through the at least one port 91. Once the balloon 90 is inflated, the at least one fluid port 93 clears the HAS of native fluid, such as blood, distal to the balloon 90 by injecting a displacing fluid, such as, for example, saline. In one embodiment, the displacing fluid is followed by another injection of a venoconstrictor, which reduces the lumen size of the HAS prior to treatment. By a temporary reduction of the size of the HAS, the treatment time used for the resistive element 92 is advantageously reduced, thereby resulting in a more effective and safe treatment.

Expandable Resistive Element Devices

Serpentine

Figure 8:
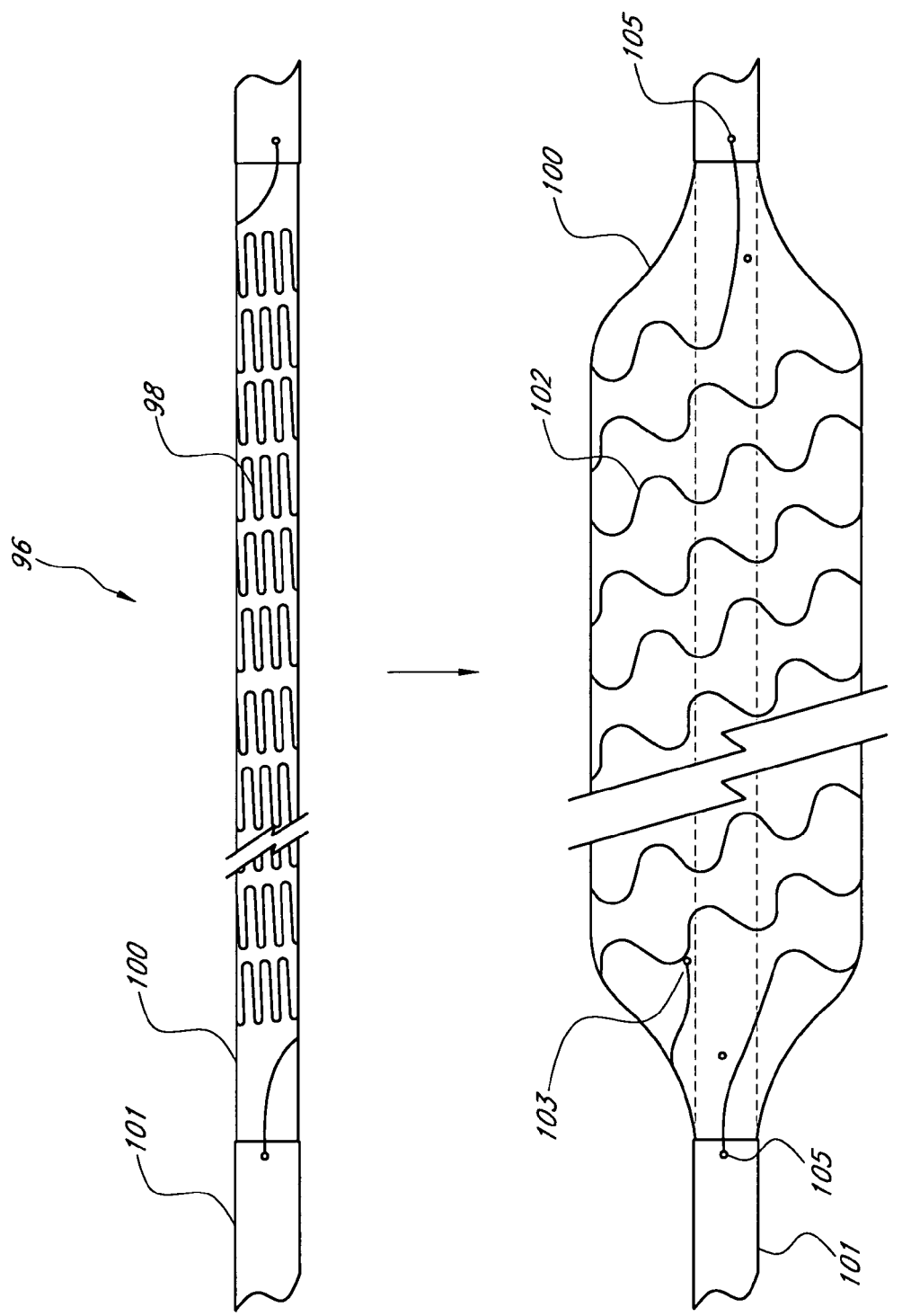
FIG. 8 illustrates another embodiment of a resistive element device having an expandable electrode.

Another embodiment of a resistive element device 96 is shown in FIG. 8, which incorporates an expandable resistive element 98 on a balloon 100. In one embodiment, the balloon 100 is made of a biocompatible material such as, but not limited to, silicone, PET, urethane, latex, C-FLEX®, combinations of the same or the like. The balloon 100 is attached at one end to a catheter shaft 101 at the working end of the catheter. In certain embodiments, both ends of the balloon 100 are sealed on the shaft 101 and are substantially fluid tight. The catheter shaft section within the balloon 100 may also contain fluid ports (not shown). The ports may be connected to lumen(s) which run internally to the shaft 101 to the proximal end. The lumen(s) at the proximal end (e.g., at a handle) may be further connected to luer components for external fluid connections. These components may be used to expand and collapse the balloon 100.

The illustrated resistive element 102 is advantageously a serpentine component, which is placed circumferentially around the exterior of the balloon 100 and catheter shaft 101. In one embodiment, the resistive element 102 expands circumferentially as the balloon 100 expands. In certain embodiments, the resistive element 102 is made of NITINOL®. For example, the shape memory aspect of NITINOL® may be advantageously utilized to help the resistive element 102 remember its expanded or collapsed position. In other embodiments, other nickel-based spring alloys, other spring alloys, 17-7 stainless steel, Carpenter 455 type stainless steel, beryllium copper, or other similar materials may be used.

In an alternative embodiment, the resistive element 102 is located within the wall of the balloon material or between two layers of the silicone balloon material. This embodiment results in the serpentine resistive element 102 being more integral to the catheter device 96.

As shown, a temperature sensor 103 is also advantageously attached to the resistive element 102 for temperature control during application of energy to the HAS. In FIG. 8, the sensor 103 is shown attached near a proximal end of the resistive element 102 but may be attached at any point axially. In one embodiment, the attachment of the sensor 103 is accomplished by soldering, bonding or tying the sensor 103 onto the section of the resistive element 102. Ends 105 of the resistive element 102 are attached to signal wires, which may run through an open lumen internal to the catheter shaft 101 and may be connected to a connector cable. These signal wires may be attached by solder (or previously discussed methods) to the resistive element 102.

The embodiment of FIG. 8 shows the resistive element 102 being capable of being placed in apposition to the wall of a HAS prior to treatment by use of the expanding balloon 100. Thus, one device may be advantageously adjusted to fit multiple sizes of hollow anatomical structures. In certain embodiments, the balloon 100 and resistive element 102 may also collapse during the last portion of the treatment or as the treatment is completed. One intent of collapsing the device 96 during the last portion of treatment is to maintain apposition with the walls of the HAS while allowing the tissue to shrink and/or constrict so as to occlude or substantially occlude the structure.

For improved viewing of the balloon 100 during expansion, a contrast medium may be used for fluoroscopy or for an ultrasonic contrast. For example, micro bubbles may be employed as part of the balloon fluid for expansion. Such a configuration may be applicable to any expandable resistive element using a fluid filled balloon.

In certain embodiments, the balloon 100 is capable of displacing a substance, such as blood, from a treatment area. In another embodiment, the balloon 100 is further capable of directing heat toward the wall of a HAS by bringing at least a portion of the resistive element 102 in proximity with, or in contact with, the wall. In yet other embodiments, the balloon 100 is configured to collapse in response to the collapsing or narrowing of the HAS and/or is configured to collapse manually.

In one embodiment, an indicator in the handle of the resistive element device 96 shows the state of inflation of the balloon 100. For example, the indicator may comprise a substance or display that moves axially to show deflation of the balloon 100. For instance, the indicator may be coupled to the expandable member (e.g., the balloon 100), such that expansion of the expandable member causes corresponding changes (e.g., movement) of the indicator. In other embodiments, the out-flowing saline is employed in a pressure or level-gauge like configuration (e.g., a thermometer-like configuration) to indicate the state of inflation of the balloon 100.

Expandable Braid

Figure 9:
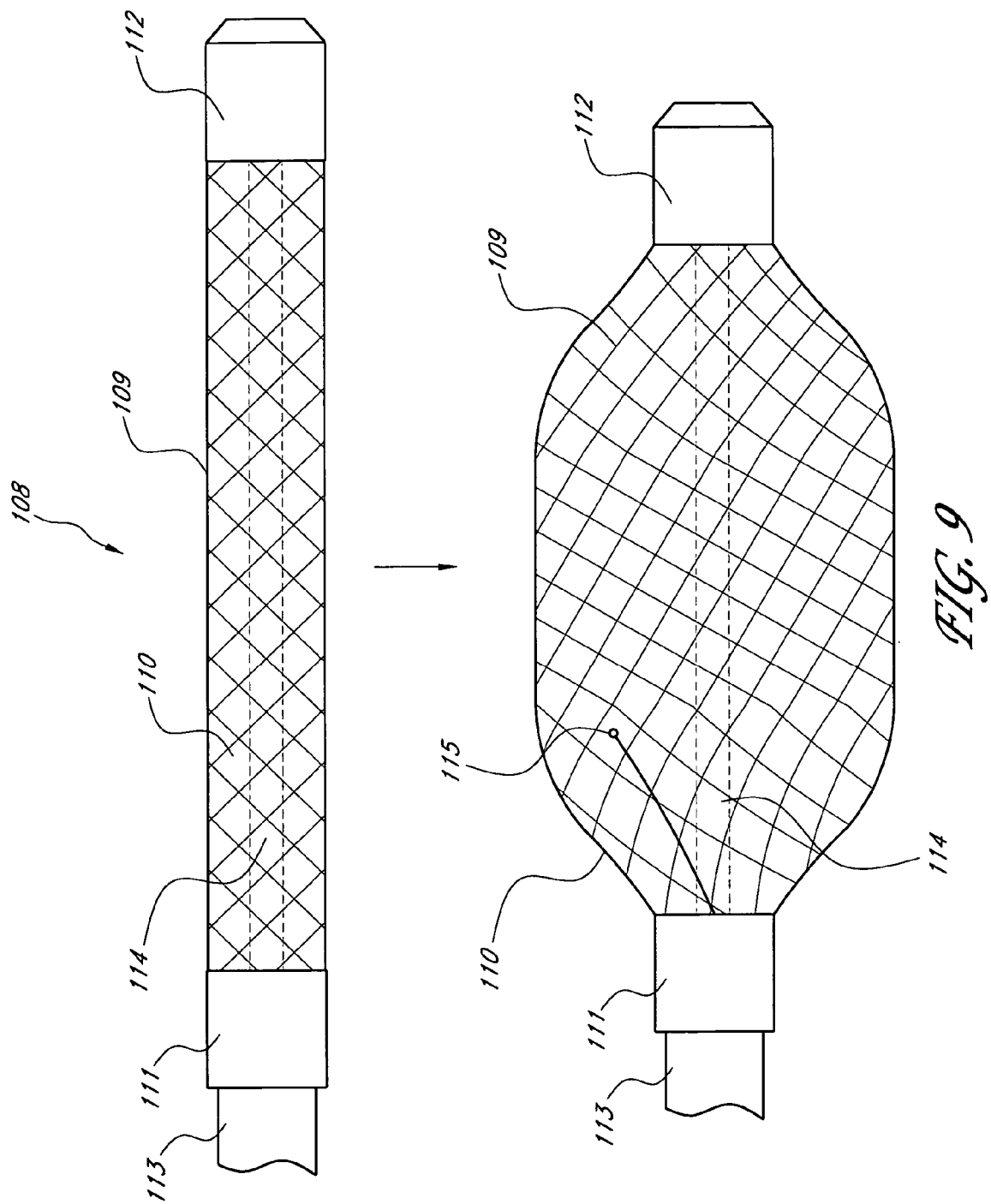
FIG. 9 illustrates yet another embodiment of a resistive element device having an expandable braid electrode.

FIG. 9 illustrates another embodiment of an expandable resistive heating element device 108. The illustrated heating element device 108 utilizes a metal braid wire 109 as the working resistive element. In certain embodiments, the wire 109 is round and/or made of NITINOL®. However, in other embodiments, the braid wire 109 may be a flat wire and/or comprise another spring-type or shape memory material as discussed above. The elastic characteristics of NITINOL®, in certain embodiments, are beneficial to the method of expanding and collapsing the device 108. In one embodiment, the braid wire 109 is heat set in the nearly fully expanded position. In other embodiments, a balloon 110 is used to expand the braid wire 109.

In one embodiment, the braid wire 109 is sleeved in polyimide to isolate the multiple wires from each other where they overlap. In other embodiments, other materials may be used, such as, for example, TEFLON®, urethane, and the like. In certain embodiments, the braid component 109 may be created using standard braiding technology. Alternatively, a single wire may be woven into the braid component 109. The particular design of the braid 109 may be selected for the overall resistance or impedance of the device 108 in view of the corresponding energy source being used.

The proximal and distal ends of the braid component 109 are captured in a two-part crimp sleeve, 111 and 112, to anchor the ends to a catheter tube 113 and a catheter tube stylet 114. The braid wire 109 in this embodiment is expanded by the use of the catheter tube stylet 114, which runs the internal axial length of the catheter from the distal tip 112 to a proximal handle. In certain embodiments, the proximal end of the stylet 114 passes through a Touhy Borst type fitting on the catheter handle and provides, in turn, a handle for stylet manipulation. In such an embodiment, pushing the stylet 114 distally collapses the braid wire 109 (illustrated in the upper portion of FIG. 9), while pulling the stylet 114 expands the braid wire 109 (illustrated in the lower portion of FIG. 9).

In the embodiment illustrated in FIG. 9, the balloon 110 is placed internal to the braid wire 109 such that the ends of the balloon 110 are distal to the crimp section 111 and proximal to the crimp 112. As previously discussed, the balloon 110 may comprise silicone, but the balloon 110 can be of other materials previously identified. The balloon 110 then uses an internal lumen and side port (not shown) of the catheter stylet 114 for inflation and/or deflation.

It should be noted that, in certain embodiments, the silicone balloon 110 may expand axially and radially when inflated. This may cause the balloon 110 to become "S" shaped for a set axial length of tubing, thus causing the braid wire 109 to have non-uniform tissue apposition with the HAS. In such embodiments, to compensate for this configuration, the balloon 110 may be pre-stretched axially just prior to anchoring on the catheter tubing to the stylet component 114. The stretched balloon 110 may then expand radially with little to no axial expansion, depending on the amount of pre-stretch performed. The balloon 110 may also be used to occlude the HAS to impair blood flow and to remove blood from the braid portion of the catheter. This creates a static fluid volume and advantageously provides for a more efficient heat treatment. Also, the balloon 110 may promote braid apposition with the HAS. In other embodiments, the balloon 110 is at least partially expanded and contracted through expansion and compression of the ends 111 and 112.

In certain embodiments, a temperature sensor 115 is attached to the braid wire 109 along its axial length. For example, the sensor 115 may be used for temperature control during the application of energy. Although the sensor 115 is shown attached near the proximal end of the braid wire 109, the sensor 115 may be located along other portions of the braid wire 109. In other embodiments, more than one sensor 115 may be used.

In another embodiment, the balloon 110 is separate from the braid device 109. For example, the balloon 110 may fit within the lumen of the braid device 109, and the tips of both the braid device 109 and the balloon 110 may connect and anchor to each other. For example, the anchor mechanism may include a set of male and female threads appropriately sized. Alternatively, the tips may be anchored together by use of axially aligned holes in both tips, through which a wire is placed and tied off. Alternatively, the tips may be designed with a spring ball detent to anchor the tips together. Alternatively, magnetic or electromagnetic materials of opposite polarity may be used to align the tips and hold them together.

Expandable Loop

Another embodiment of a resistive element system 118, which is shown in FIG. 10A, utilizes at least one expandable loop 119 that emanates from a side of the main catheter shaft 120. In particular, one end of the loop 119 is anchored to the catheter shaft 120. The other end of the loop 119 passes through an opening 122 in a sidewall of the catheter shaft 120 and runs through the catheter lumen to a handle at the proximal end of the catheter shaft 120. In certain embodiments, this second end of the loop 119 functions as a stylet in order to manipulate the shape and/or size of the loop 119.

In one embodiment, the loop 119 comprises a wire 123 that coils around the main catheter body 120 with spaced attachment points (such as, for example, by entering into and exiting from segments of a lumen within the main catheter body 120). In such an embodiment, by advancing the wire 123 the coils extend beyond the main catheter body 120 as circular coils extending substantially perpendicular to the axis of the main catheter body 120. In certain embodiments, the wire 123 is generally circular in cross-section. In one embodiment, the loop 119 is pre-shaped in order to extend outward toward and/or to contact the walls of a HAS. Alternatively, the wire 123 that forms the actual exposed loop 119 may be flat, rectangular, ovular, or have other geometrical cross sections. In one embodiment, rotating a stylet handle end of the loop 119 manipulates, or twists, the loop 119 toward or away from the catheter shaft 120.

In certain embodiments, the loop 109 may comprise a resistive element similar to the element 14 of FIG. 1. For example the loop 109 may comprise a resistive element coil. In addition, each loop 109 may have a temperature sensor on the resistive element for use in temperature controlled energy delivery. In other embodiments, each resistive element may be covered with a sleeve. For example, the sleeve material may comprise PET, TEFLON®, polyimide or other like material.

Wavy Expandable Length

Another embodiment of a resistive element system 126 is shown in FIG. 10B and utilizes at least one expandable formed set of bends. A main spline 127, as shown in more detail in FIG. 10D, forms a backbone and is, in certain embodiments, made of NITINOL®. In other embodiments, the spline 127 is made of other nickel-based spring alloys, 17-7 stainless-steel, Carpenter 455 type stainless-steel, or beryllium copper or similar materials. As shown in FIG. 10D, the illustrated spline 127 is wound with a resistive wire 130, an example of which is discussed in more detail with respect to FIG. 4. In certain embodiments, the device 126 illustrated in FIG. 10A may also include a temperature sensor. Because the illustrated spline 127 slides into a tube 131, the spline 127 may comprise an outer sleeve 132 made of TEFLON®, or other like material, for reduced frictional force.

In one embodiment, the spline 127 is straightened by withdrawing it proximally into the tube 131. For example, the tube 131 may comprise an inner liner 134, which extends out of the tube end and is formed into an outer lip 133, which is shown in more detail in FIG. 10C. In addition, FIGS. 10A-10C show the wind of the spline 127 as two-dimensional. However, a skilled artisan will recognize from the disclosure herein that the spline 127 may also comprise various three-dimensional shapes, such as for example, a helical wind. The particular shape may be used to improve contact of the heating element to the wall of a HAS during treatment.

Expandable Floating Ribbon

Figure 11:
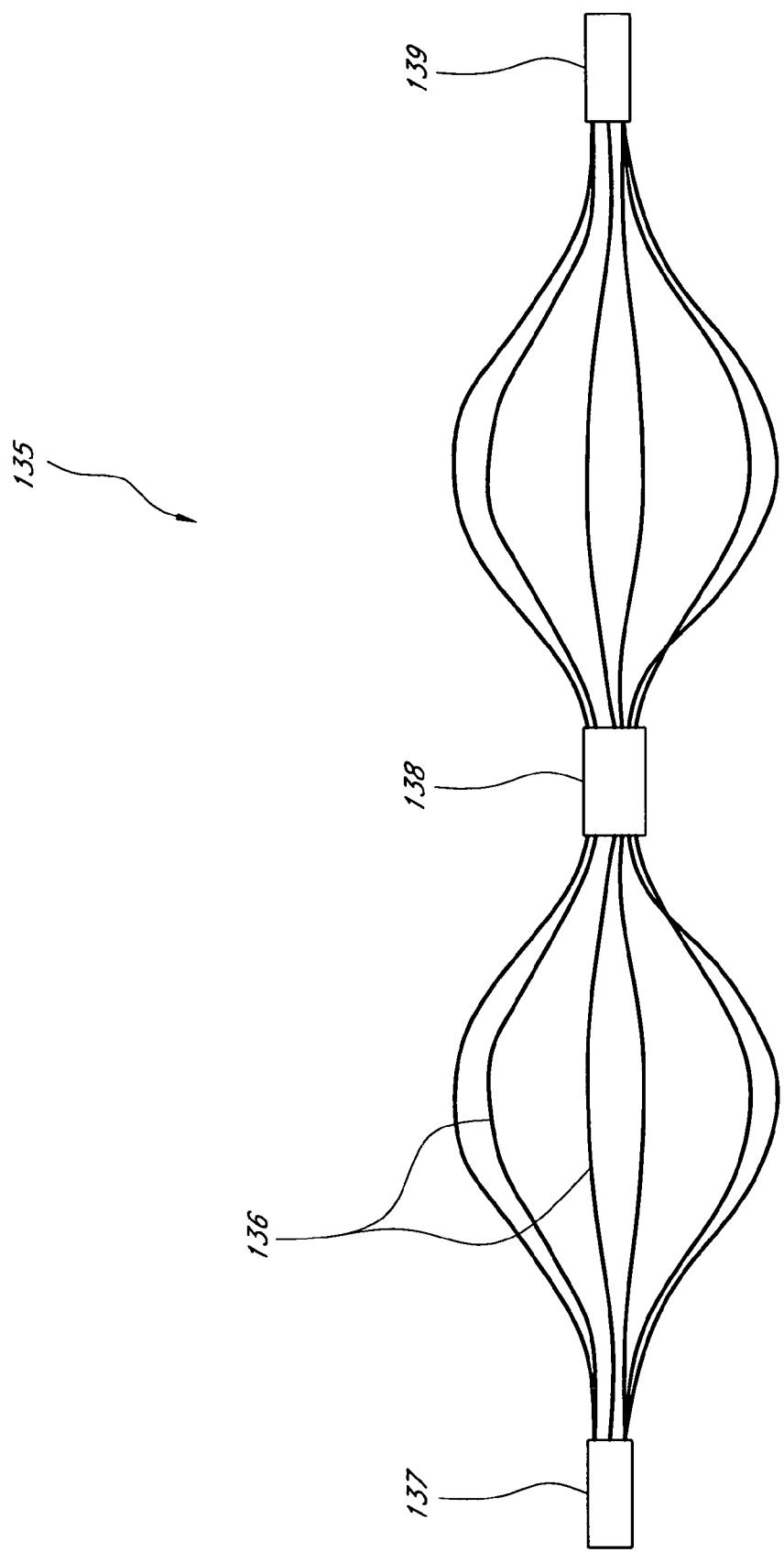
FIG. 11 illustrates an exemplary embodiment of an expandable set of spline electrodes capable of conforming and contacting a vein wall.

FIG. 11 illustrates another embodiment of a resistive element device 135 using at least one expandable resistive element. In the illustrated embodiment, pre-shaped splines 136 act as individual resistive heating elements. The set of splines 136 is attached radially about a catheter shaft 137; In certain embodiments, the spline set 136 has at least one expandable resistive element section. In FIG. 11, the illustrated device 135 has two expandable sections. As shown, the spline set 136 is anchored at a midpoint 138, which preferably does not substantially expand. A tip 139 and proximal end attached to the shaft 137 also preferably do not substantially expand.

In certain embodiments, the device 135 is designed to collapse by use of an outer sheath (not shown), which in FIG. 11 would be in a retracted position. For example, the sheath may be used to help place the device 135 in the HAS and to help remove the device 135 after treatment. One intent of the self-adjusting splines 136 is to allow for expansion such that the splines 136 are in apposition to tissue and adjust to any axial bends or curves in the subject HAS. As the HAS is heated during treatment, the lumen of the structure constricts and/or shrinks, and the spline set 136 adjusts and collapses concurrently with the lumen. This same characteristic also gives the device 135 of FIG. 11 versatility, as it is able to accommodate varying sizes of hollow anatomical structures.

Alternatively, the device 135 comprises a stylet wire similar to the braid device of FIG. 9 in order to collapse and expand the pre-shaped splines. In such an embodiment, the splines may be manually collapsed during treatment in order to follow the occlusion of the HAS.

In certain embodiments, each spline 136 is made of a resistive material as previously discussed. Alternately, at least one spline 136 may have a resistive coil wire wrapped around it, as is previously described. In certain embodiments, a temperature sensor may also be attached to at least one spline 136 for temperature controlled energy delivery.

In certain embodiments, one long expandable section makes up the spline set 136. To support the length during treatment, a balloon may be placed inside the spline set 136. For example, this balloon may use an internal lumen of the catheter (not shown) for inflation and deflation. Alternatively, as described for the braid device, the balloon may be a separate device inserted into the long expandable spline set 136.

As discussed previously with respect to the fixed diameter resistive element, the spline resistive elements 136, when individually wired for power, may also be used advantageously in conjunction with a multiplexing process. Such an embodiment allows for the sequential or "cascading" heating of specific resistive element subsets of the spline set 136. Such multiplexing may involve energizing at least one spline 136 for a specific dwell time and then cascading or moving to the next adjacent spline(s) 136 until the end spline is reached. The cycle is then repeated until the complete treatment time is reached.

Super Elastic Expanding Ribbon

FIGS. 12A-12C illustrate an embodiment of a treatment catheter with a helical coil resistive element 140. For example, the coil resistive element 140 may be manipulated from a collapsed or small-diameter coil tightly wrapped around the circumference of a catheter shaft (see FIG. 12A) into an expanded, large diameter coil (see FIG. 12C). In one embodiment, the coil 140 comprises a resistive material as discussed earlier. The expanded coil 140 may also be in apposition with the wall of a HAS. In one embodiment, the catheter shaft is made of two concentric tubes or shafts, 142 and 143. In such embodiments, the proximal tube 142 may be slightly larger in diameter to fit over the distal tube 143. The distal tube 143 is capable of rotating about the catheter tube axis relative to the proximal tube 142. In the illustrated embodiment, clockwise rotation of the distal tube 143 expands the resistive element coil 140 (as shown in FIG. 12C), and counter-clockwise rotation of the distal tube 143 collapses the resistive element coil 140 (as shown in FIG. 12A).

FIG. 12A shows the initial collapsed position of the device when, for example, the catheter is initially placed in the HAS. FIG. 12B shows a mid-range of the radial expanding resistive element coil 140, and FIG. 12C shows a final state of the device completely expanded. In certain embodiments, the coil 140 is adjusted to eliminate the inter coil spacing by being pushed distally. The steps described may also be reversed to collapse the device for new placement or for removal.

In one embodiment, for the distal tube 143 to rotate and move axially, the distal tube 143 is connected to a torquable stylet wire (not shown). This stylet may run internal to the proximal tube 142 and/or the distal tube 143 and may be accessible at a catheter handle. In one embodiment, the handle also locks the stylet in position in order to maintain the resistive element in a collapsed and/or expanded state.

In certain embodiments, the resistive element 140 is made of NITINOL® having a shape memory property that returns the resistive element 140 to its pre-shaped expanded coil form upon heating. In such an embodiment, one end of the coil 140 may be tethered to the catheter, such as for example, the proximal end. The expanded coil 140 may also "auto collapse" as the HAS shrinks and/or constricts during the treatment. In another embodiment, a sheath is used to retrieve the coil 140 after treatment.

Figure 13B:
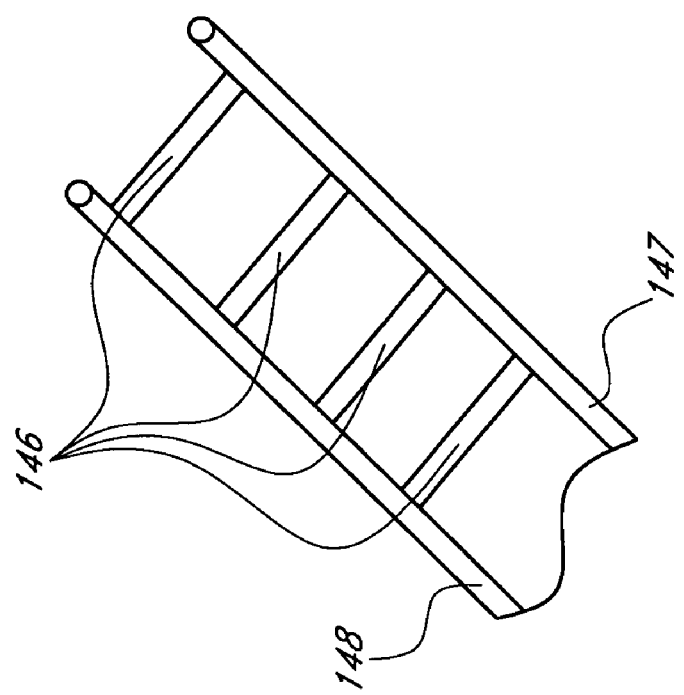
FIG. 13B illustrates an exemplary embodiment of the device of FIG. 13A uncoiled to flatten out the multiple strip electrodes.
Figure 13A:
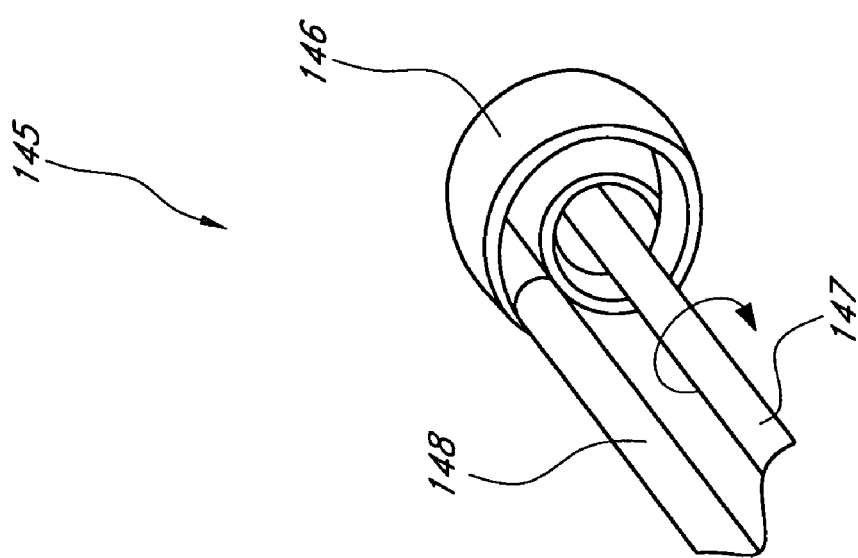
FIG. 13A illustrates an exemplary embodiment of a strip electrode coiled substantially normal to a catheter shaft axis.

FIGS. 13A and 13B show an embodiment of an expandable flat strip resistive element device 145 that includes radially expanding coiled strips 146. As shown, the device 145 has at least one strip resistive element 146. FIG. 13A shows the resistive element 146 collapsed (i.e., coiled tightly). By rotating a first stylet component 147 in a clockwise direction, the illustrated resistive element 146 winds up into a collapsed coil. Likewise, by rotating the stylet wire 147 in a counter-clockwise direction, the illustrated coil 146 expands and adjusts to be in apposition with a wall of a HAS. A secondary stylet 148 is shown as a stationary component (e.g., not rotatable). In other embodiments, the stylet 148 may also comprise a catheter tubing or component that attaches to the end of the resistive element 146 and/or that is rotatable.

FIG. 13B is an example of a 4-resistive element strip version of the device 145 of FIG. 13A and is illustrated in a flat, expanded position. In such an embodiment, the resistive element strips 146 comprise resistive material as previously discussed. Stylets 147 and 148 connect to the resistive element strips 146, and the strips 146 heat up when energized. Alternatively, the strips 146 may have resistive wire wrapped around them to form coil-type resistive elements.

In certain embodiments, one or more temperature sensors, as previously described, may also be attached to at least one strip 146 for temperature-controlled energy delivery. In addition, strip resistive elements 146 may be used in conjunction with the multiplexing process to heat specific subsets of the group of resistive elements 146.

In an alternative embodiment, a resistive heating device can be configured such that the resistive heating element also acts as a resistance temperature device (RTD). Certain metals exhibit predictably varying electrical resistance properties at varying temperatures. If this relationship is known for a given resistive heating element, a temperature of the element can be determined by measuring an electrical resistance across it. Such a system may advantageously eliminate the need for additional thermocouples or other temperature sensing devices and/or may provide an independent sensing of temperature for high-temperature situations.

Indexing

In some embodiments, it is desirable to provide a heating element configured to treat a relatively short lengths of a HAS at successive intervals. Such an embodiment can be progressively moved through the HAS in a series of discrete steps from a first position to a final position in order to treat a desired length of the HAS. The process of moving a heating element through a HAS in a series of discrete steps during treatment is referred to herein as "indexing."

A general indexing process may proceed by providing an elongate catheter with a relatively short-length heating element at a distal portion thereof. The heating element and/or catheter may be inserted through an introducer sheath into a HAS, such as, for example, a vein. The heating element is advanced to a distal-most position, and power is then applied thereto. The temperature of the subject heating element is allowed to ramp up or increase to a desired temperature and remains in place for a desired dwell time. Once the desired dwell time is reached (e.g., the treatment for the section is completed), the heating element can be powered down, and the element can be indexed proximally to a second position, at which point at least one of the ramp up, dwell, power down, and indexing procedures may be repeated.

FIGS. 14 through 30B illustrate embodiments of short-length heating elements and indexing systems. It should also be noted that the devices and structures discussed previously herein may also be used in an indexing system. For exemplary purposes, several of the following embodiments are described with reference to a coil-type resistive element.

For example, FIG. 14 illustrates one embodiment of an indexing HAS treatment system 200 comprising an elongate catheter 202 extending through an introducer sheath 204, which includes a hub 206, and a heating element 208 located at the distal end of the catheter shaft 205.

In certain embodiments, the heating element 208 is an electrically resistive heating element, including but not limited to any of those described elsewhere herein, such as any of the embodiments of the resistive element 14 described herein. For example, the heating element 208 may comprise a single, bifilar or other electrically resistive wire. The heating element 208 can also comprise multiple, separately operable heater sections (as in the resistive element 70), to provide a heating element 208 which has an adjustable active length, or an active region which is adjustable in size. FIG. 14 further illustrates an embodiment of the heating element 208 comprising a wire having tightly-wrapped coils around a hollow, elongate structure. Thus, the embodiment of FIG. 14 can include a heating element 208 in the form of a coil similar to that shown in partial section in FIG. 4 above. In other embodiments, the heating element 208 may comprise a loose, tight, or variable-pitch coil wound around a solid or hollow elongate structure. In other embodiments, the heating element 208 is composed of an electrically-resistive tube that can reach and maintain high temperatures (e.g., a solid-state heater).

In certain embodiments, the heating element 208 has a substantially short axial length. For example, in certain embodiments, the heating element 208 has a length of between approximately one centimeter and approximately ten centimeters. Such a length is believed to be particularly advantageous for embodiments utilizing manual, external compression to treat a HAS. In certain preferred embodiments, the length of the heating element 208 is between approximately three centimeters and approximately seven centimeters.

In certain embodiments, the heating energy delivered by the heating element 208 of the system 200 is less than 100 watts. In a more preferred embodiment usable in an indexing process, the heating energy delivered by the heating element 208 is between approximately ten watts and forty watts.

In certain embodiments, in order to accurately index the heating element 208, it is desirable to provide a means for repeatedly moving (or facilitating accurate, repeated repositioning of) the heating element 208 proximally within an HAS undergoing treatment by a desired distance. In certain embodiments, this desired distance is less than the overall length of the heating element 208 so as to effectively re-treat regions that may receive less heat energy as a result of an uneven heating profile along the axial length of the heating element 208. It may also be desirable to treat more than once a portion of an initial and/or final treatment region of the HAS in order to arrange for start- and endpoints of the indexing distances to correspond with catheter shaft markings or to arrange that, after the full series of indexed treatments, the final HAS treatment region is in substantial alignment with the end of the introducer sheath 204. It may also be desirable to treat more than once a complete treatment region or regions of the HAS (e.g., for the case of saphenous vein ablation, double-treating the segment nearest the saphenofemoral junction, in the region nearest a large tributary vessel, or at an aneurismal vein segment). In addition, in certain embodiments, the system 200 includes means for preventing the heating element 208 from being powered up while it is within the introducer sheath 204.

In certain embodiments, as illustrated for example in FIG. 15A, the catheter shaft 205 may comprise a plurality of markings 211 along the axial length thereof in order to assist in visual verification of indexing positions. Such markings 211 advantageously assist a user in positioning and indexing the heating element of the catheter 202 during treatment. For example, the user may determine from the markings 211 how far the heating element should be retracted during a treatment interval.

In certain embodiments, the physician uses the markings 211 to manually and selectively move the catheter 202 within a HAS of a patient. For example, the catheter 202 may have an associated therapeutic or heating element at the end thereof that extends approximately seven centimeters in length. In such an embodiment, the markings 211 may be spaced apart at approximately 6.5 centimeter intervals. When treating the patient, the physician may use the markings 211 to manually withdraw along the HAS the catheter 211 at 6.5 centimeter intervals between successive treatments of the HAS. Such a 6.5 cm movement can be performed by proceeding from a first state in which a first shaft marking 211 is aligned with a fixed reference point (e.g., the proximal edge of the introducer sheath hub 206 or other datum as discussed in further detail below), then moving the catheter shaft 205 proximally (or distally) to reach a second state in which a proximally (or distally) adjacent second shaft marking 211 is aligned with the fixed reference point. In other embodiments, and as discussed in more detail below, a device may be used to automatically withdraw the catheter at the predetermined intervals indicated by the markings 211.

In certain embodiments, the location of a therapeutic energy application device, such as a heating element, within the HAS may be indicated by a visibility-enhancing element. The visibility-enhancing elements may be located at one or both ends of the therapeutic energy application device, or may be located along some or all of the length of the therapeutic energy application device.

In some embodiments, the visibility-enhancing element may facilitate the unmediated visualization of the location of the therapeutic energy application device using the naked eye, as for example in the case of through-tissue illumination. For example, FIG. 15B illustrates an embodiment of a catheter that may incorporate one or more light emitters such as optical fibers such that an illuminating spot appears at one or both ends of the therapeutic energy application device through illumination holes 212. Alternatively, the light emitters may be configured to direct light radially outward away from the longitudinal axis of the elongate catheter shaft. In certain embodiments, such light emitters may be spaced radially apart around the longitudinal axis of the elongate catheter shaft. The illumination may be powered by a light emitting diode (LED) and battery within the handle of the catheter, by an external light source that may be separate or included as part of the power generator for therapeutic heating, or by any other device known in the art for generating light, whether electrically, chemically, or by any other known principle.

In some embodiments, the visibility-enhancing element may facilitate the visualization of the location of the therapeutic energy application device mediated by a viewing system, as for example in the case of the use of ultrasound or radiation-based viewing systems. Visibility-enhancing elements for use with an ultrasound viewing system include, for example, a portion of the apparatus that is rendered highly reflective of ultrasound. This can be accomplished by, for example, applying a surface treatment to a portion of the apparatus, such as at or near the therapeutic energy application device, such that the surface more readily traps gas microbubbles, which reflect ultrasound. Alternatively, the portion can be produced using a specialized coating, comprising a smooth biocompatible polymer coating containing effervescent agents, that has a microbubble-generating effect. An example of such a coating is Phyz™ coating. In a further embodiment, one or more gas bubble delivery ports may be provided at or near the therapeutic energy application device, to provide greater contrast when viewing with ultrasound. Alternatively, the visibility-enhancing element may comprise one or more ultrasound emitters, which may employ any structure known in the art. Furthermore, visibility-enhancing elements for use with a radiation-based viewing system include, for example, portions of the apparatus that are relatively highly radiopaque. In one embodiment, for example, a radiopaque element may be applied at or near the therapeutic energy application device. The radiopaque element may comprise a single, elongate element, such as a wire, wrapped around the therapeutic energy application device substantially continuously along the entire length of the therapeutic energy application device. Alternatively, the radiopaque element may comprise a coating, plating or film adhered to the coil along its length. The radiopaque materials used for this radiopaque element may comprise, for example, platinum, gold, tantalum, or any other radiopaque material known in the art.

Furthermore, in one embodiment, the therapeutic energy application device has a length greater than the width thereof. In another embodiment, the therapeutic energy application device is a closed circuit therapeutic energy application device. In another embodiment, the therapeutic energy application device has a fixed profile in a plane orthogonal to the longitudinal axis of the therapeutic energy application device.

FIGS. 16A-16D depict one embodiment of the HAS treatment system 200 and a method of its use to treat a vein, such as the great saphenous vein (GSV) as depicted, near its junction with the femoral vein (FV), at the sapheno-femoral junction (SFJ). In other embodiments the system 200 can be used to treat other HASs, such as other veins.

Figure 16A:
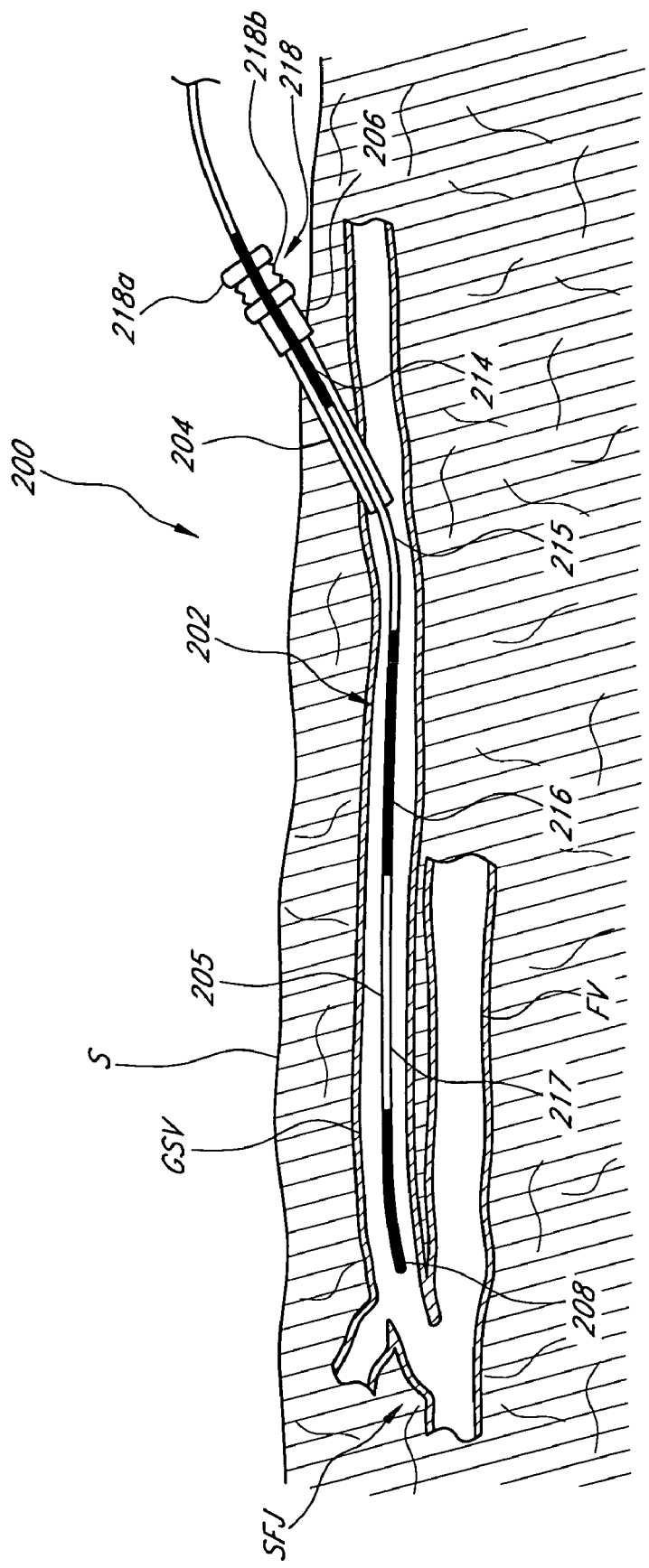
FIGS. 16A-16D illustrate another exemplary embodiment of a catheter usable with an embodiment of an indexing treatment system for hollow anatomical structures.

In certain embodiments, and as depicted in FIG. 16A, the introducer sheath 204 is first inserted through the patient's skin S and manipulated until the distal end of the sheath 204 is within the lumen of the GSV, and the hub 206 remains outside the skin surface. Once the sheath 204 is in place, the catheter 202 is passed distally through the lumen of the sheath 204, and into the GSV until the distal tip of the heating element 208 is positioned at or near the SFJ, as shown in FIG. 16A. To facilitate insertion of the catheter 202, in certain preferred embodiments, the introducer sheath may have a minimum inner diameter of approximately 2.33 millimeters (approximately seven French). The position of the heating element 208 can be monitored or confirmed using appropriate corporeal vision techniques, such as, for example, ultrasonic imaging.

In the embodiment of FIGS. 16A-16D, the catheter shaft 205 is marked with first, second, third and fourth marking sections 214, 215, 216, 217, which are marked on the shaft 205 in any of the arrangements set forth herein (e.g., alternate colored and/or cross-hatched sections, or a series of tick marks spaced apart from each other by the desired indexing distance, and/or geometrically coded markers of alternating or varying shape) so as to make the distal and proximal edges of each section 214, 215, 216, 217 easily visible by the user. Thus, the user can observe the marking section(s) to determine the relative position of the heating element 208 within a HAS and/or with respect to the introducer sheath 204. Preferably, the axial length of each section 214, 215, 216, 217 is approximately equal to the length of the heating element 208, less any intended overlap distance between treatments. In one preferred embodiment, the heating element 208 is seven centimeters in length and each section 214, 215, 216, 217 is 6.5 cm in length. The shaft 205 can be varied in length so as to include more or fewer sections than the four depicted in FIGS. 16A-16D.

Generally, the heating element 208 (or an energy coupling surface thereof) can have a suitable axial length and the length of each section 214, 215, 216, 217 can be the heating element length (or energy coupling surface length) less a decrement which can be between 1% and 15% of the heating element length. This decrement corresponds to a treatment overlap length as explained above. In some embodiments, the heating element 208 can be between 2 and 10 centimeters in length, and the decrement can be between 0.1 and 1.5 centimeters. In still other embodiments, the length of each section 214, 215, 216, 217 can be slightly greater than the length of the heating element 208.

In addition, in certain embodiments the length of the heating element 208 is greater than the width thereof. (The width of the heating element is the greatest dimension (e.g. the diameter) of a cross-section of the heating element 208 taken orthogonal to the longitudinal axis.) The length of the heating element can be, in various embodiments, at least ten times the width thereof, or at least fifteen times the width thereof.

The sheath 204 depicted in FIGS. 16A-16D includes a longitudinally adjustable datum device or reference point indicator 218, which can be employed to provide a fixed reference for the position of the shaft 205 and heating element 208 as discussed in further detail below. Preferably connected to the proximal end of the hub 206, the reference point indicator 218 comprises a reference point 218*a* which is longitudinally moveable relative to the hub 206 via an adjustable section 218*b*, which in the depicted embodiment comprises an accordion section. Alternatively, the adjustable section 218*b* can comprise a threaded cylinder or other threaded member (not shown) which engages threads on the hub 206 to facilitate longitudinal movement of the reference point 218*a* via rotation of the adjustable section 218*b* relative to the hub 206. However implemented, the adjustable section 218*b* is preferably transparent, or includes a transparent window or an opening to permit the user to see the portion of the catheter shaft 205 that passes through the adjustable section 218*b* proximal of the hub 206.

Figure 16B:
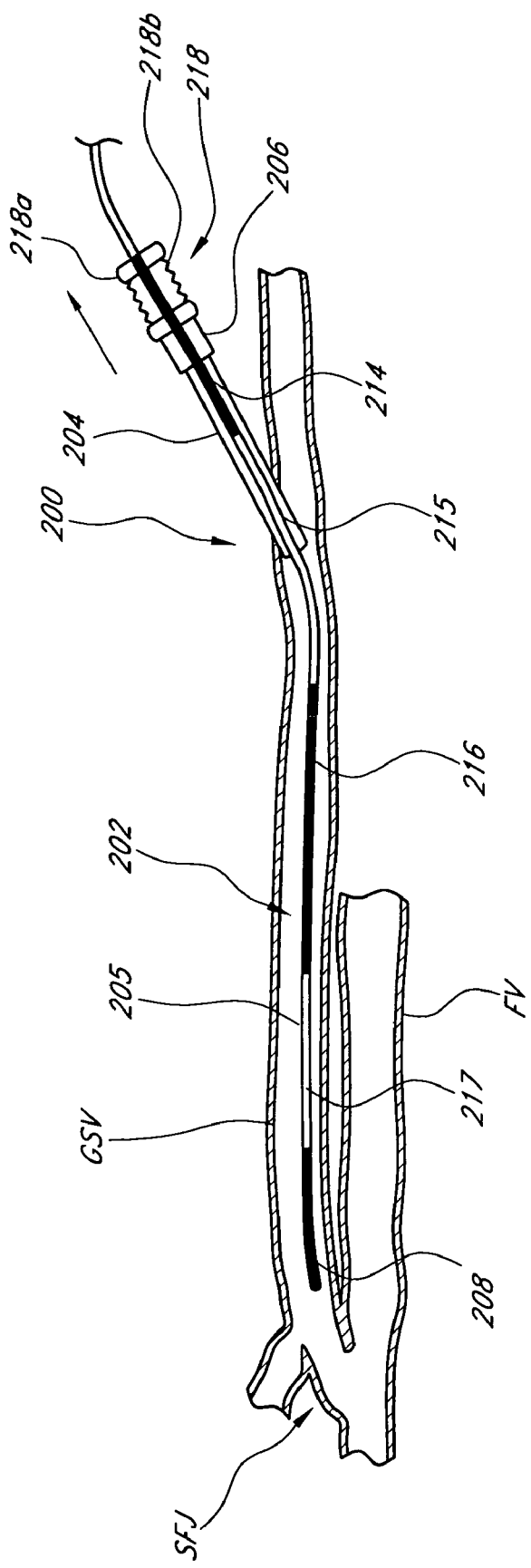

With resumed reference to the method depicted in FIGS. 16A-16D, once the catheter 202 is in place in the GSV with the heating element 208 near the SFJ (FIG. 16A), the user adjusts the reference point indicator 218 by aligning the reference point 218*a* with the proximal edge of the first marking section 214. In FIG. 16B, this is depicted as a proximal movement of the reference point 218*a* relative to the catheter shaft 205, accomplished by longitudinally stretching or extending the accordion section and then fixing the reference point 218*a* in the correct position by any suitable means. Where the adjustable section 218*b* comprises a threaded cylinder or the like, the cylinder is rotated until the reference point 218*a* reaches the correct position, where it is fixed in position. Alternatively, the user may partially withdraw the introducer sheath 204 proximally from the GSV until the sheath hub 206 or reference point indicator 218 is aligned with an indexing marking (e.g. an indexing marking 219a), shaft tick mark, marking segment, etc.

Preferably, after alignment of the reference point indicator 218 or the proximal end of the sheath 204 with an indexing marking, etc. as discussed above, the user secures the sheath 204 with respect to the GSV, so that the sheath end or reference point indicator 218 can serve as a fixed reference point for indexing of the catheter 202. This can be accomplished by, for example, securing the sheath 204 to the patient, which can comprise suturing or taping the sheath to the skin of the patient near the insertion site of the sheath.

Figure 16C:
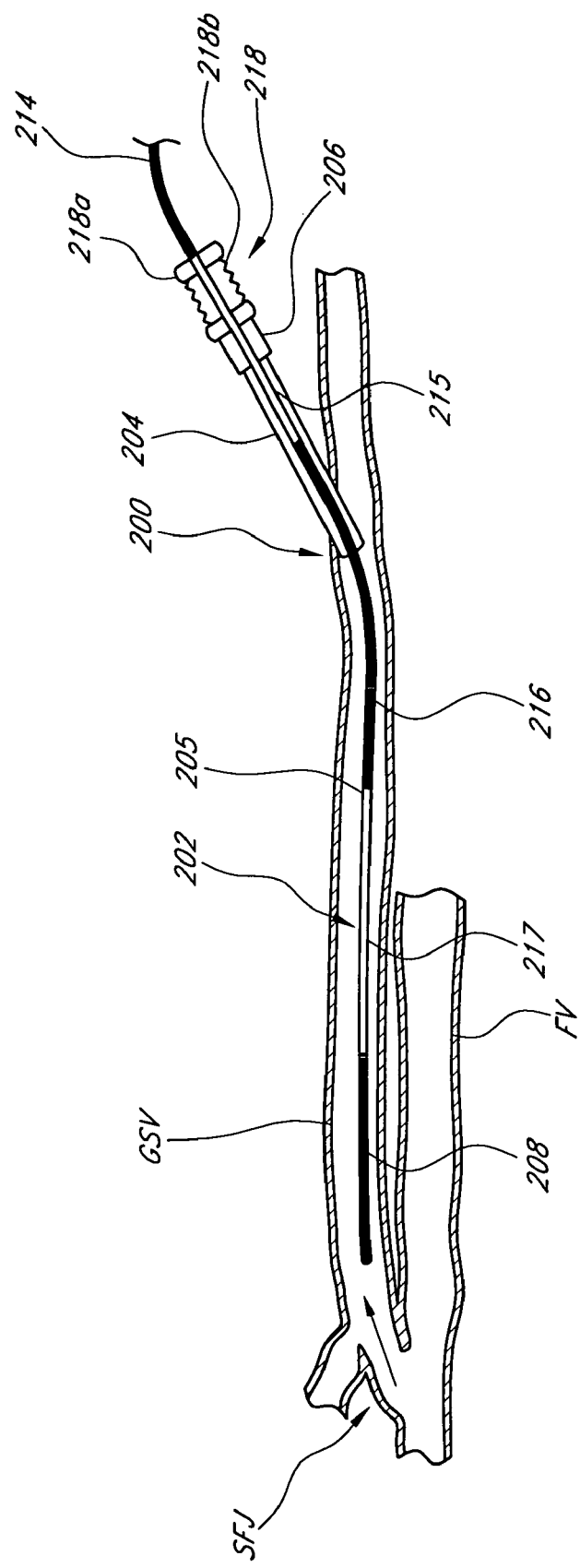
Figure 16D:
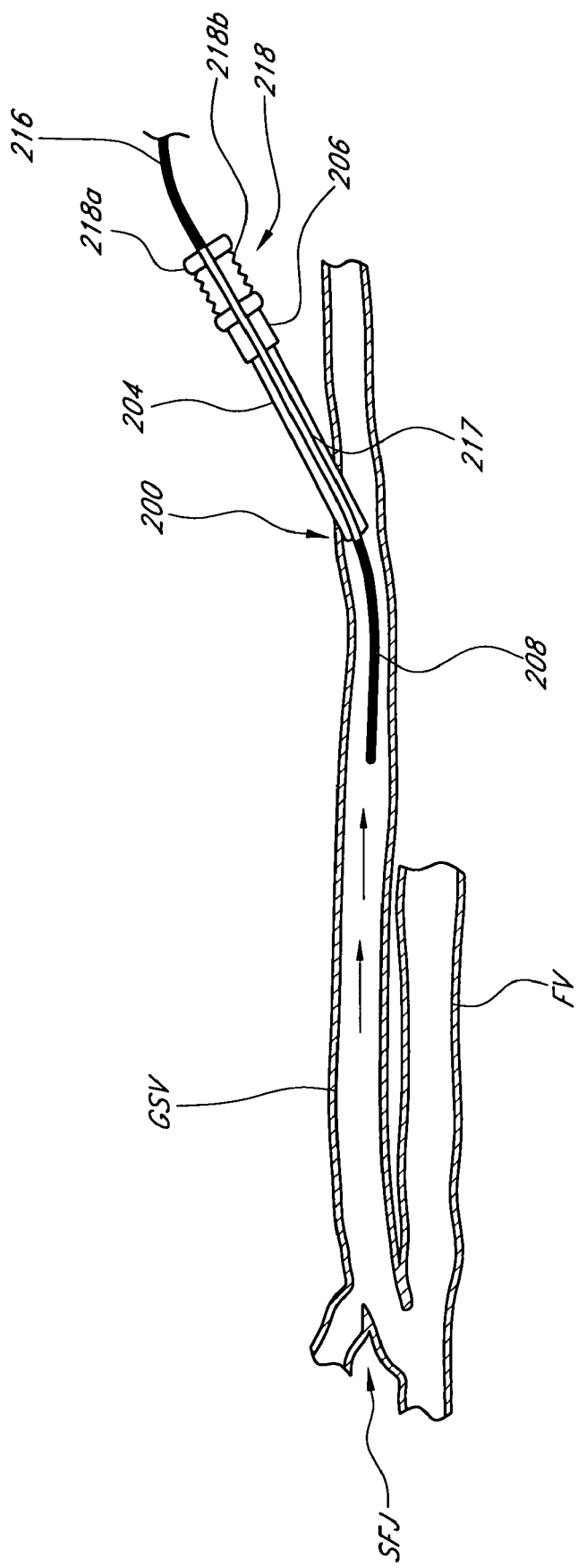

The system 200 is now ready for use in treating the GSV as follows. FIG. 16B shows the heating element 208 in an initial treatment position near the SFJ. At this point, the user activates the heating element 208 by cycling through the steps of powering up the heating element 208, dwelling at a power or temperature state (or series of states), and then powering down the heating element 208. Having completed the treatment cycle for an initial, distal (e.g., limb-proximal) section of the GSV, the user may perform a second treatment closest to the SFJ. The user then moves the catheter shaft 205 and heating element 208 proximally by the desired indexing distance (e.g., 6.5 cm), by moving the shaft proximally until the proximal edge of the second marking section (e.g., to the next tick mark) 215 is aligned with the reference point 218a (FIG. 16C). The user then repeats the treatment cycle with the heating element 208. Following the treatment cycle, the user again moves the shaft 205 and heating element 208 proximally by the indexing distance, pulling the shaft proximally until the proximal edge of the third marking section 216 (e.g., to the next tick mark) is aligned with the reference point 218a.

This sequence of treatment cycle-index-treatment cycle is repeated until the desired length of the GSV (or other vein or HAS) has been treated, at which point the catheter 202 and introducer sheath 204 are removed from the treatment area.

In certain embodiments, the fourth or distal-most marking section 217 indicates a "stop treatment zone" or a "last treatment zone," which can be employed to prevent the heating element 208 from being withdrawn too far (e.g., into the introducer sheath 204). For example, the fourth marking section 217 may comprise a band of a solid or patterned color such as red, yellow or other color or pattern that contrasts with the base color or pattern of the catheter shaft 205.

Furthermore, when implemented as a stop-treatment marker, the fourth or distal-most marking section 217 preferably has a length that is substantially equal to the length of the introducer sheath 204 (rather than having a length equal to the desired indexing distance as discussed above), which generally includes, but is not limited to, the following lengths: five, seven and eleven centimeters. In certain embodiments, a plurality of distinct stop-treatment markers may be used on a single shaft 205, the plurality of stop-treatment markers corresponding to the various lengths of introducer sheaths usable with the catheter 202. When employed, the stop-treatment marker is preferably distinct from the indexing markers. For example, the stop-treatment marker can be of a type, shape, length, color, pattern and/or configuration that differs from that employed for the indexing markers.

Thus, when used as a stop-treatment marker, if the proximal edge of the fourth or distal-most marking section 217 is pulled out of the proximal end of the introducer sheath 204 (see FIG. 16D), the user will know that the heating element 208 is positioned within the introducer sheath 204. The user can then push the catheter 202 distally until the stop-treatment marker is positioned within the hub of the introducer sheath 204, thus avoiding damage to the sheath 204 and/or heating element 208.

Where the catheter 202 employs a heating element 208 with an adjustable active length or adjustable active region as discussed above, the heating element can be operated with a shortened or reduced active length or region to facilitate treating a "partial" length of the HAS, which is shorter than the entire heating element length. This is useful for treating a relatively short portion of the HAS at the beginning and/or end of the treatment process.

In certain embodiments, the indexing process described with reference to FIGS. 16A-16D allows a user to treat selected segments of a HAS for successive periods of time. Furthermore, the markings 214-217 and the reference point indicator 218 of the introducer sheath 204 advantageously allow the user to determine the relative position of the heating element 208 within the HAS and/or with respect to the introducer sheath 204 through a means external to the body of the patient.

Although described with reference to particular embodiments, other types or forms of markings may be used with embodiments of the HAS indexing system described herein. For example, in certain embodiments, it may be desirable to provide a unique marker to indicate a final, proximal-most, indexed position so that the corresponding heating element remains spaced from the introducer sheath by a sufficient distance to prevent the sheath from melting.

As mentioned above, the introducer sheath 204 advantageously includes a longitudinally adjustable reference marker 218. The sheath 204 has a lumen which extends from the distal tip of the sheath (shown inserted within the GSV in FIG. 16A) to the proximal edge of the hub 206. The sheath lumen extends generally along a luminal axis in a distal-to-proximal direction, and a portion of the catheter shaft 205 is depicted as passing through the sheath lumen and along the luminal axis in FIGS. 16A-16D. As seen in FIGS. 16A-16B, the position of the reference marker 218a is longitudinally adjustable relative to the sheath 204 in the distal-to-proximal direction, along the luminal axis.

In one embodiment, the reference marker 218 is removably coupled to the proximal end of the sheath 204, so that it can be easily removed or attached for use as the surgical situation demands. In further embodiments, any of the various reference markers 218 described herein can be connected (either in a removable fashion, or substantially permanently such as by integral formation) to the proximal end of any of the sheaths 223a, 223b, 223c shown in FIG. 16H, or to the proximal end of any other suitable sheath type. Advantageously, the longitudinally adjustable nature of the reference marker 218 facilitates alignment of the reference marker with one of the indexing markings on the shaft 205 without need for movement of the shaft 205 relative to the sheath (or vice versa).

FIG. 16E illustrates another embodiment of a catheter 202' usable to treat a HAS, according to certain embodiments. As shown, the catheter 202' includes a set of markings to inform the user when a heating element, or other therapeutic element, of the catheter 202' is approaching an introducer sheath. In certain embodiments, such markings advantageously prevent a user from drawing the heating element into the introducer sheath, which may cause damage (e.g., melting) to the sheath.

As shown, the catheter 202' includes indexing markings 219a usable to successively treat predetermined lengths of a HAS, as is described in more detail with reference to FIGS. 16A-16D. For instance, the indexing markings 219a may correspond to the locations of the edges of the first, second, third and fourth marking sections 214, 215, 216, 217 of the catheter shaft 205 illustrated in FIGS. 16A-16D. In certain embodiments, the indexing markings 219a are of a width easily visible by a user, such as for example, approximately 0.2 centimeters.

In certain embodiments, the distance "a" between each of the indexing markings 219a is approximately 6.5 centimeters. In such embodiments, the length of the therapeutic element may extend further than 6.5 centimeters, such as approximately seven centimeters, such that there exists a slight overlap between successive treatment portions. In certain embodiments, the catheter 202' may include approximately sixteen indexing markings 219a. In yet other embodiments, other numbers of, or distances between, indexing markings 219a may be used as appropriate. For instance, a catheter with a shorter therapeutic section may utilize a shorter distance between indexing markings.

Generally, in the catheter 202' of FIG. 16E the therapeutic element or heating element (or an energy coupling surface thereof) can have a suitable axial length and the distance "a" between each of the indexing markings 219a can be the heating element length (or energy coupling surface length) less a decrement which can be between 1% and 15% of the heating element length. This decrement corresponds to the desired treatment overlap length as explained above. In some embodiments, the heating element can be between 2 and 10 centimeters in length, and the decrement can be between 0.1 and 1.5 centimeters. In still other embodiments, the distance "a" between each of the indexing markings 219a can be slightly greater than the length of the therapeutic element.

In addition, in certain embodiments the length of the therapeutic element or heating element of the catheter 202' is greater than the width thereof. (The width of the heating element is the greatest dimension (e.g. the diameter) of a cross-section of the heating element taken orthogonal to the longitudinal axis.) The length of the heating element can be, in various embodiments, at least ten times the width thereof, or at least fifteen times the width thereof.

The illustrated catheter 202' further includes a warning section 220 and at least one warning marking 219b that inform a user that the associated therapeutic element is approaching the introducer sheath through which the catheter 202' is inserted. For instance, the warning section 220 may identify the position of the catheter 202' relative to an introducer sheath during treatment of a final section of the HAS. In certain embodiments, this final section is the final full-length section (e.g., seven centimeters) treated with the therapeutic section of the catheter 202'.

In certain embodiments, the warning section 220 includes a distinct color and/or pattern that distinguishes the section 220 from other portions of the catheter 202'. For instance, the warning section 220 may include a red or yellow color. In certain embodiments, the warning section 220 may also be substantially the same length as the marking sections identified by the indexing markings 219a. For instance, a distance "b" may be approximately 6.5 centimeters.

The at least one warning marking 219b advantageously identifies the furthest point(s) to which the catheter 202' may be drawn without entering the introducer sheath. In particular, the illustrated catheter 202' includes three warning markings 219b that correspond to three different sized introducer sheaths (e.g., a seven-centimeter sheath, an eleven-centimeter sheath and a fifteen-centimeter sheath). These multiple markings allow for flexibility and/or adaptability in use of the catheter 202' because the user may appropriately manipulate and use the catheter 202' with different-length sheaths.

In use, the warning markings 219b, in combination with the warning section 220, inform a user when to stop drawing the catheter 202' through the introducer. For instance, the user may utilize the indexing markings 219a as he/she treats successive portions of a HAS. During this treatment process, the user incrementally draws the catheter 202' out of the associated introducer. When the warning section 220 becomes visible, such as when the warning section 220 as been fully drawn out of the introducer (e.g., such that a distal end of the warning section is substantially flush with an introducer hub), the user is informed that the therapeutic element of the catheter 202' is near the introducer sheath.

Subsequent warning markings 219b further alert the user as to the final position(s) of the catheter 202' before the therapeutic element enters the introducer sheath. As shown, each of the warning markings 219b includes an associated alphanumeric marking that corresponds to a certain-length introducer sheath. For instance, the three illustrated warning markings 219b include the numbers "7," "11" and "15," which correspond to, respectively, warning markings for a seven-centimeter introducer sheath, an eleven-centimeter introducer sheath and a fifteen-centimeter introducer sheath.

For example, as shown, the warning markings 219b include a first warning marking positioned a distance "d" from a distal end of the catheter 202' and includes the alphanumeric character "7." In certain embodiments, the distance "d" is preferably at least as long as the sum of the length of the therapeutic section and the length of the particular introducer sheath. For example, the catheter 202' includes a therapeutic element with its proximal end identified by an element marker 219c and having a length "c" of approximately eight centimeters, which may include a one-centimeter terminal portion at the distal end of the catheter 202' that is not used for therapeutic treatment. In such an embodiment, the distance "d" preferably would be at least fifteen centimeters in length. Furthermore, in certain embodiments, the diameter of the therapeutic element may be approximately 2.25 millimeters.

Moreover, the catheter 202' includes a second warning marking positioned a distance "e" from the end of the catheter 202' and including an alphanumeric character "11." The catheter 202' also includes a third warning marking positioned a distance "f" from the end of the catheter 202' including an alphanumeric character "15." In embodiments wherein the catheter 202' includes a therapeutic element with a length of approximately seven centimeters, plus a one-centimeter terminal portion, the distance "e" is at least nineteen centimeters, and the distance "f," is at least twenty-three centimeters.

In certain embodiments, the catheter 202' has an overall insertable length "g" of approximately 100 centimeters. In yet other, embodiments, the catheter 202' may be shorter or longer as appropriate. For example, the catheter 202' may have an overall insertable length of approximately 60 centimeters.

In certain embodiments, the catheter 202' comprises a flexible shaft and an inner lumen extending therethrough. For instance, the lumen may be utilized for flushing the catheter 202' prior to insertion of the catheter 202' into the patient and/or for optional use of a guidewire to aid in navigation of the catheter 202' through the patient's venous anatomy.

Although FIG. 16E depicts one embodiment of the catheter 202', other embodiments may include fewer than or more than three warning markings. For instance, another embodiment of the catheter may include only warning markings corresponding to two introducer sheath lengths, such as, for example, seven centimeters and, preferably, eleven centimeters.

FIG. 16F illustrates a magnified view of a portion of the catheter 202' depicted in FIG. 16E. In particular, FIG. 16F illustrates the portion of the catheter 202' having the element marker 219c, the three warning markers 219b and a portion of the warning section 220.

FIG. 16G illustrates another embodiment of a catheter 202" usable to treat a HAS, according to certain embodiments. Similar to the catheter 202' of FIG. 16E, the catheter 202" includes indexing markings 219a, the warning section 220, warning markings 219b and a therapeutic element 208. For example, in certain embodiments, the therapeutic element 208 may comprise a heating element, such as a resistive heating element.

FIG. 16H illustrates three different-sized introducers that are usable in embodiments for treating a HAS. As shown, a first introducer 223a includes an introducer sheath 231a coupled to a fluid conduit 233a through an introducer hub 235a. In certain embodiments, the introducer sheath 231a is inserted through the patient's skin. A treatment catheter is then inserted into the introducer hub 235a and through the introducer sheath 231a into a HAS of the patient, such as a vein. The fluid conduit 233a further allows for the insertion and/or removal of fluids, through the introducer sheath 231a, into and/or from the HAS. In certain embodiments, the introducer sheath 231a has a length of approximately fifteen centimeters.

As further illustrated in FIG. 16H, a second introducer 223b includes an introducer sheath 231b coupled to a fluid conduit 233b through an introducer hub 235b. In certain embodiments, the introducer sheath 231b has a length of approximately eleven centimeters. A third introducer 223c includes an introducer sheath 231c coupled to a fluid conduit 233c through an introducer hub 235c. In certain embodiments, the introducer sheath 231c has a length of approximately seven centimeters.

Figure 17A:
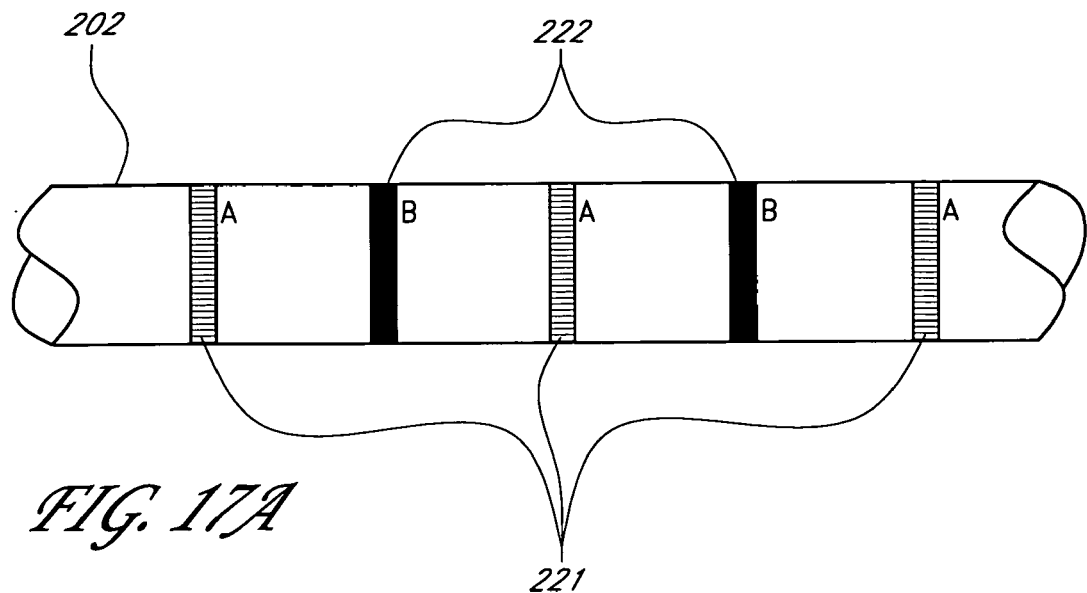
FIGS. 17A and 17B illustrate exemplary embodiments of markings usable for visual verification of indexing positions of a catheter.
Figure 17B:
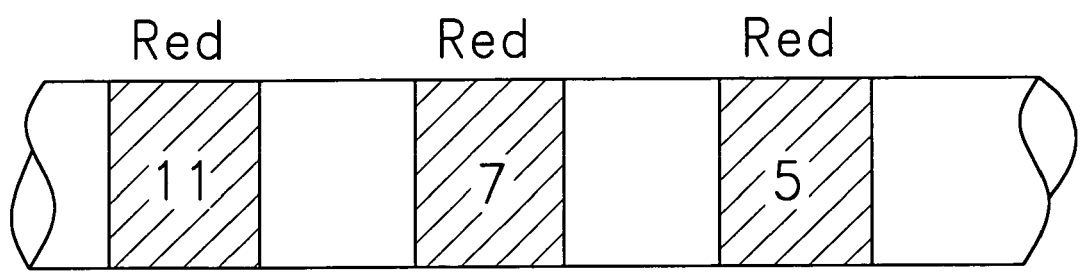

FIGS. 17A and 17B illustrate additional catheter shaft markings usable for performing an indexed treatment process, such as (but not limited to) the process depicted in FIGS. 16A-16D. FIG. 17A illustrates a catheter having regularly-spaced, alternating colored and/or alternating light/dark lines that correspond to desired indexing locations and/or distances. Such alternating markers advantageously simplify the indexing process by removing any need for counting individual centimeter-spaced markers on the shaft. Furthermore, the alternating characteristics (e.g., color, pattern) of the markings helps prevent repeated treatment of the same area.

As shown, the catheter has a first set of markings 221 that alternates with a second set of markings 222 along the length of the catheter shaft. As shown in FIG. 17B, the marks may alternate between red and white colors. The alternating markings may also include reference symbols, numbers, letters such as "A" and "B," as shown in FIG. 17A, or other marks in order to further distinguish any given indexing position from the adjacent indexing position(s).

As discussed above, the markings on the catheter shaft 202 of FIGS. 17A-17B may be arranged such that the index distances defined between consecutive index step marks are actually shorter than the length of the corresponding heating element. Again, this encourages intentional overlapping of indexed treatments. For example, for a heating element length of approximately seven centimeters, the shaft markers 221, 222 (e.g., the distance between consecutive A-A or B-B shaft marks) can be arranged to indicate a 6.5 centimeter index step, which may create a substantially consistent 0.5 centimeter treatment overlap. Such an embodiment may be particularly advantageous when the heating profile is not consistent across the heating element (e.g., a lower temperature at the outside edges of the heating element in comparison to the temperature of a middle portion of a heating element).

Similar to the embodiments discussed above, the catheters of FIGS. 17A-17B are used by being placed within a HAS at a desired position for an initial treatment. When the initial treatment is about to start, the physician or other user notes which catheter shaft marking (e.g., which letter or color segment) is adjacent to the proximal edge of the hub of the introducer sheath (or aligned with whichever reference point or datum device is employed). If the initial adjacent/aligned shaft marker segment is of a first type (e.g., the mark 221 having the letter "A" with reference to FIG. 17A) then the start of the index step for the second treatment is at the start of the next mark of the same type (e.g., the mark 221 having the letter "A" with reference to FIG. 17A) on the catheter. This arrangement enables the physician to retract the heating element of the catheter proximally by the desired indexing distance, by moving the catheter until the opposing type of mark is aligned with the hub edge or reference point. Alternatively, the treatment process is started with "B" and each successive treatment is indexed to the next "B" marker.

Where the proximal edge of the introducer sheath hub is employed as the reference point for positioning and moving the catheter, and if upon initial catheter placement in a HAS only a partial length of a segment marked on the shaft initially extends proximally out of the hub (similar to the situation in FIG. 16A, but without the reference point indicator 218), then the physician can simply perform a partial-length index step after the initial treatment. In other words, the physician performs a first treatment cycle with the heating element and catheter in its initial placement in the HAS, and then moves the catheter proximally by a partial index distance, until the proximal edge of the next adjacent marked shaft segment is aligned with the proximal edge of the introducer sheath. The usual treatment then proceeds, with one or more "full-segment" treatments.

Alternatively, to address such a situation, the intervals between the alternating shaft markers (e.g., markers 221 and 222, or the distance between consecutive A-B shaft marks) may have a length equal to approximately half of the desired index length in order to reduce the length of a double-treated section, thereby expediting the overall treatment process. With markers so arranged, the first catheter movement stops at the first shaft marker encountered, and subsequent catheter movements are a full index distance in length proceeding to the next shaft marker of the same type.

Still another way to address the "partial-segment" issue is the use of an adjustable datum device, as described in more detail above with respect to the reference point indicator 218 of FIGS. 16A-16D, and below with respect to FIGS. 19 and 20. These devices may be used to designate an initial datum point or reference point such that the second treatment is a full index distance from the initial treatment (in other words, such that the catheter and heating element move a full index distance between the initial treatment and the second treatment). Nonetheless, as mentioned above, a double treatment can be performed at the beginning and/or at the end of the treatment procedure (e.g., during the initial and/or final treatment interval) if it is determined that such a double-treatment would have a beneficial effect on the overall HAS treatment results.

Figure 18A:
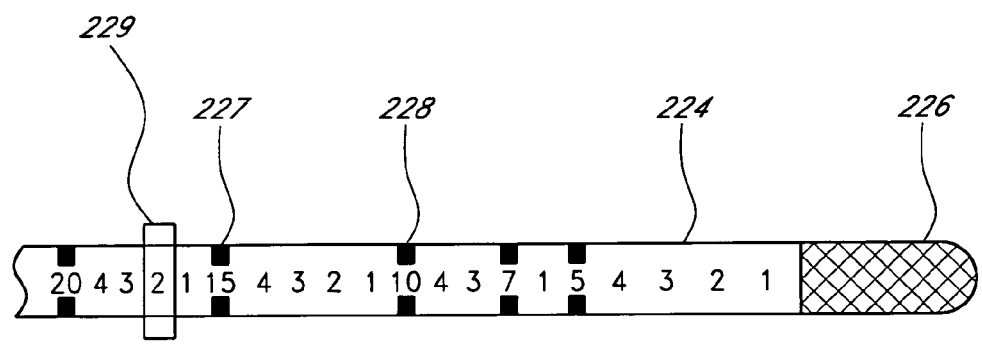
FIGS. 18A and 18B illustrate other exemplary embodiments of markings usable for visual verification of indexing positions of a catheter.

FIG. 18A illustrates another embodiment of an indexing system including a catheter 224 with regularly-spaced, numbered marks that, when the catheter 224 is in use, correspond to indexing locations and/or distances. The catheter 224 includes a heating element 226 at the distal end of the catheter 224 and a sleeve 229 usable to identify the current indexing position. The illustrated catheter 224 advantageously includes a shaft marked with numerical values for use during the indexing process. For example, the numerical values may correspond to the length of the catheter 224 portion extending within the HAS or may correspond to the distance of (the proximal end of) the heating element 226 from (the distal end of) the introducer sheath. In yet other embodiments, the numerical values may correspond to the total length of the treated portion of the HAS.

As further illustrated in FIG. 18A, the catheter 224 may comprise major (e.g., five-centimeter-increment) markings 227 and 228 that include numerical values that increase proximally along the catheter shaft 224. Between these major markings 227 and 228 there are additional shaft marks that comprise a repeated group of the numbers (e.g., 1, 2, 3 and 4), letters (e.g., A, B, C and D) and/or shapes (e.g., triangles, circles, diamonds and squares) to designate lengths in between (or otherwise smaller than the distance between) the major markings 227 and 228.

In some embodiments, different combinations or sets of numerical markings may be used depending on the particular treatment parameters (e.g., heat, time duration, length of HAS treatment portion, and the like). In yet other embodiments, the catheter 224 may comprise more than one movable position-indicating sleeve 229. For example, a first reference marker may be used to indicate the current position of the heating element 226, and a second reference marker may be used to indicate how far the catheter 224 should be re-inserted during a treatment process.

In certain embodiments, the position-indicating sleeve 229 is movable (e.g., slidable) along the shaft of the catheter 224. For example, during a treatment process, a user may slide the position-indicating sleeve 229 to the edge of a sheath in order to highlight the desired current numerical value.

In certain embodiments, the shaft markings of HAS indexing catheters as described herein are spaced at repeated intervals, such as for instance one centimeter. In such embodiments, the major increments (such as five centimeters) can have numbers that increase proximally along the shaft. In use, the initial two treatment locations within the HAS may overlap by as much as nearly the full length of the catheter's heating element. In certain embodiments, the increments marked on the catheter shaft may be in fractional dimensions. For example, in certain embodiments using a seven centimeter heating element, the increments marked on the catheter shaft may be approximately 6.5 centimeters in length.

Figure 18B:
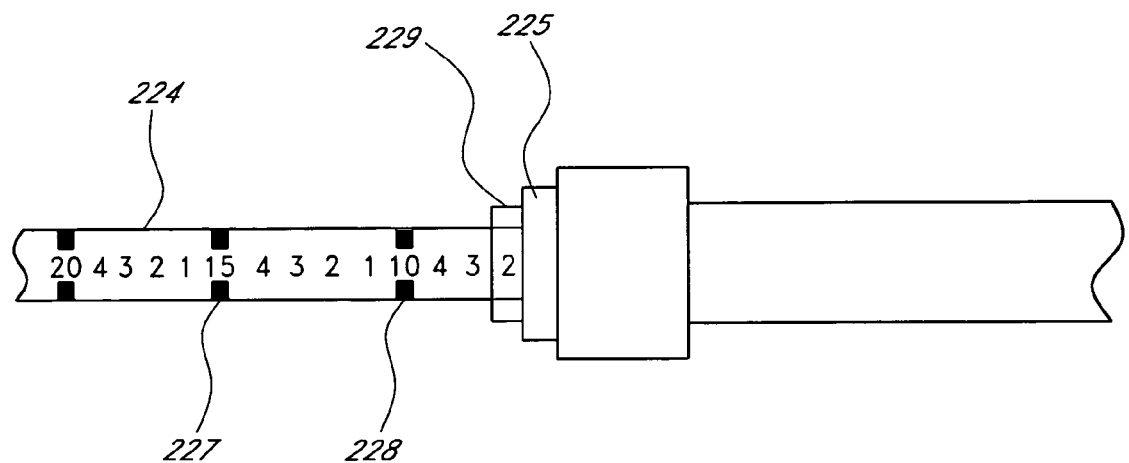

As shown in FIG. 18B, the distal-most position-indicating sleeve 229 may be placed against an introducer sheath hub 225 to highlight the current shaft marking-number for indexing. In such an embodiment, if the treatment process is interrupted, the position-indicating sleeve 229 records catheter position information such that the physician can resume the treatment process with the heating element in the correct position. In certain embodiments, the sleeve 229 also is capable of remaining in a selectively-fixed position (e.g., due to a friction fit) even when the catheter 224 is temporarily removed from the introducer sheath hub 225. In such embodiments, the physician is able to advantageously continue a treatment process when returning or replacing the catheter 224 into the introducer sheath hub 225. With reference to FIG. 18B, a return of the catheter 224 having the sleeve 229 highlighting the number "2" indicates that the next treatment step is the next identical proximal marker (i.e., the number "2" mark (obscured from view in the figure as it is covered by the sheath) between major markings 227 and 228).

Figure 19:
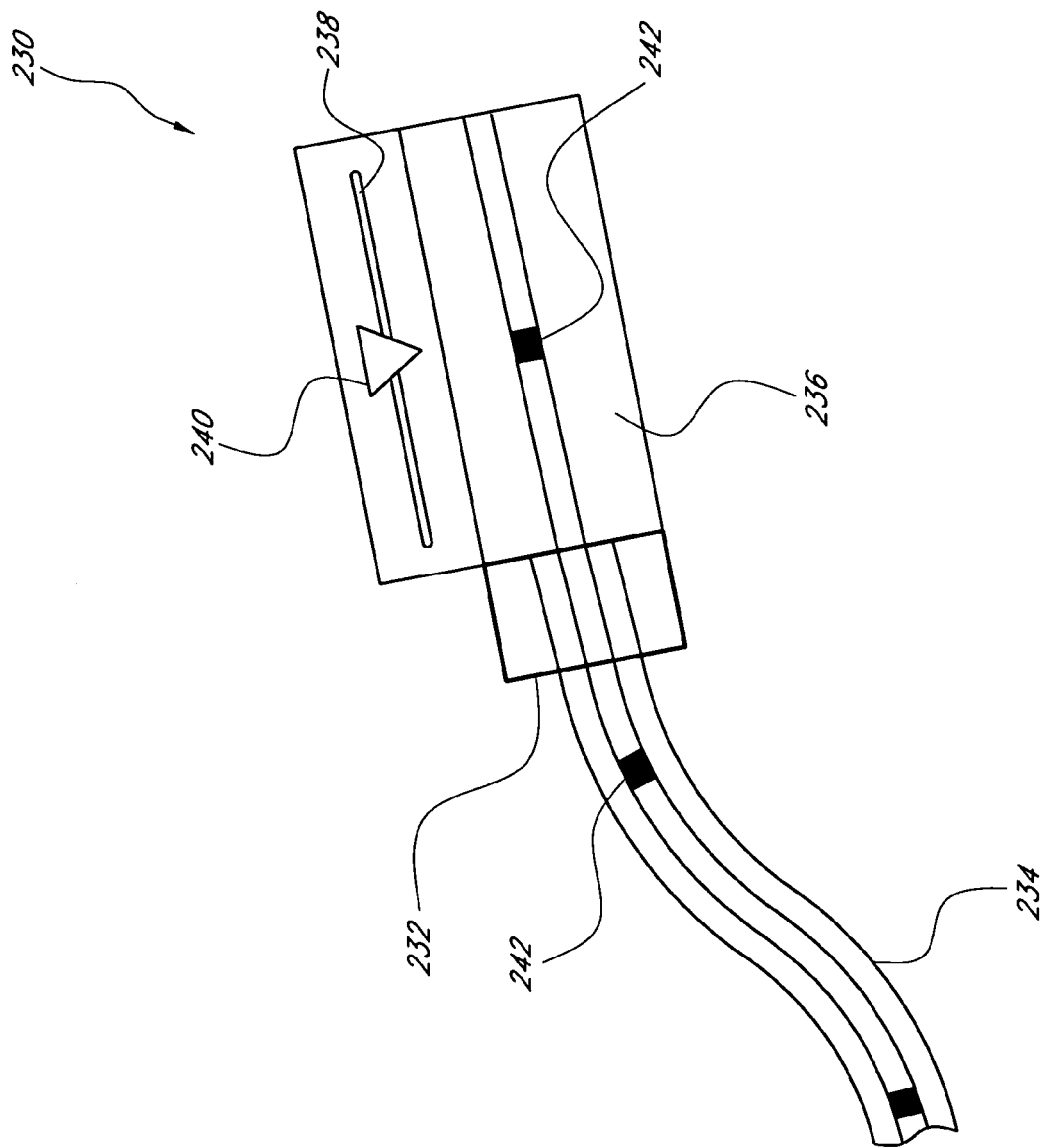
FIG. 19 illustrates an exemplary embodiment of a movable datum device usable with an indexing treatment system.
Figure 20:
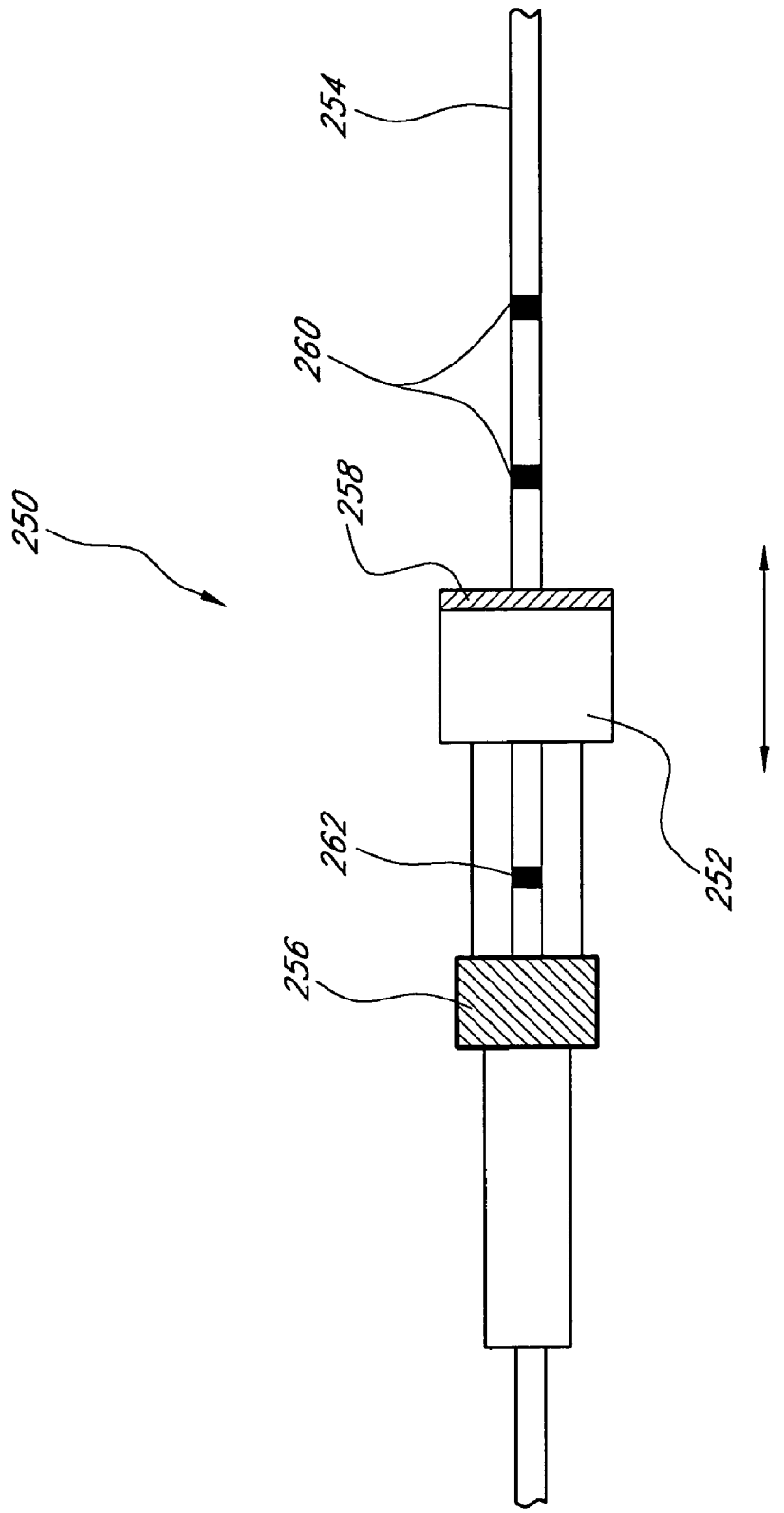
FIG. 20 illustrates another exemplary embodiment of a movable datum device usable with an indexing treatment system.

Each of the embodiments depicted in FIGS. 19 and 20 comprises a movable datum device or reference point indicator usable for establishing a starting position for a first treatment, or otherwise provide a fixed reference point for tracking the position and movement of the catheter and heating element. FIG. 19 illustrates one embodiment of a datum device 230 coupled to an introducer sheath hub 232 that serves as an attachment point to a catheter 234. As shown, the datum device 230 includes a sleeve, or body, 236 that includes a slot 238 running in an axial direction such that the ends of the slot 238 do not extend beyond the length of the sleeve 236. A pointer 240 is slidably positioned within the illustrated slot 238. In certain embodiments, the pointer 240 is advantageously mounted within the slot 238 such that there is substantial resistance to sliding, so that the pointer 240 can substantially maintain its position as a reference marker. In certain embodiments, the sleeve or body 238 may comprise a transparent or semi-transparent material, or may include portions removed therefrom, such that index markings 242 on the catheter 234 can be seen as they approach the pointer 240.

In certain embodiments, prior to a first heating treatment, the datum device 230 is adjusted to point at the nearest catheter shaft marking 242. For example, a physician may slide the pointer 240 until it lines up with a shaft marking 242 visible through the sleeve 238. This gives the physician a starting or reference point so that a fixed-length or measured-length index step can be performed by subsequently aligning other of the catheter markings 242 with the pointer 240. In certain embodiments, such a datum device 230 advantageously facilitates accurate alignment of the catheter 234 nearing fractions of a centimeter.

FIG. 20 illustrates an embodiment of a datum device 250 comprising an axially adjustable sleeve 252 provided adjacent to the proximal end of a catheter 254. In particular, the adjustable sleeve 252 is mountable to an introducer sheath hub 256. In certain embodiments, the tubular sleeve 252 attaches directly to the introducer sheath hub 256 and telescopes axially along the longitudinal axis of the sheath hub 256. In such embodiments, the sleeve 252 may preferably attach to the hub 256 using a snap fit, a threaded-fit, or another like interface, such that the sleeve 252 maintains its location relative to the hub 256 during use.

In certain embodiments, a proximal end of the sleeve 252 functions as the datum pointer. In such embodiments, portions of the sleeve 252 are preferably transparent or semi-transparent so that catheter markings 260 may be observed as they approach, or are substantially covered by, a reference marker 258 on the sleeve 252. For example, the reference marker 258 may comprise a colored line, or other identifying feature, that extends at least partially along or near the proximal edge of the sleeve 252.

In use, the adjustable sleeve 252 advantageously provides an adjustable datum or starting point from which each successive indexing position can be measured. For instance, the sleeve 252 may be coupled to the introducer hub 256 through a flexible (e.g., accordion-like) section that allows for extension/retraction of the sleeve 252 axially along the catheter 254. In other embodiments, the sleeve 252 may be movable (e.g., slidable) with respect to the hub 256. In yet other embodiments, other arrangements may be used as appropriate that allow for relative movement between the sleeve 252 and the hub 256 to provide for an adjustable return point. Such embodiments provide a user with information relating to a relative positioning of the catheter 254 and facilitates the prevention of a heating element (e.g., at the end of the catheter 254) from entering the introducer sheath. For example, in certain embodiments, and as illustrated in FIG. 20, the datum device 250 may further include a "stop" mark that indicates to the user to cease retracting the catheter into the sheath 256. Alternatively, the user may partially withdraw a sheath such that a portion of the sheath to be used as a datum (e.g., the proximal edge of the sheath hub) is aligned with a catheter mark.

FIGS. 21A-21D illustrate an example of another embodiment of a HAS indexing treatment device 270. In particular, FIG. 21A illustrates the treatment device 270 as including a catheter 272 comprising a slidable outer sleeve 277 with hub 274 and as having said outer sleeve 277 proximate a therapeutic element 280. For example, the therapeutic element 280 may comprise a heating element usable in the treatment of a HAS, such as in a method of treatment similar to that described with reference to FIGS. 16A-16D. Thus, in various embodiments, the therapeutic element 280 can comprise any of the devices disclosed herein as suitable for use as the heating element 208. The illustrated outer sleeve 277 further includes a terminal portion 279. For instance, the terminal portion 279 may comprise a different color and/or pattern than the remaining portion(s) of the outer sleeve 277. For example, the terminal portion 279 may be a red or yellow color to visually set apart the terminal portion 279.

FIG. 21B illustrates an equivalent length of an introducer sheath 282 next to the terminal portion 279 or the different color and/or pattern section. As this section emerges from the stationary introducer sheath 282, the physician is alerted to the proximity of the therapeutic element 280 to the tip of the introducer sheath 278, which advantageously indicates the end of the indexed set of treatments.

In certain embodiments, the therapeutic element 280 is configured to limit travel of the outer sleeve 277, such as by having an increased diameter and/or by providing a physical stop, such as, for example, a ring attached to the proximal end of the therapeutic element 280. In certain embodiments, the outer sleeve 277 is shorter in length than the main body of the catheter 272 by approximately one index section.

In certain embodiments, during use just prior to the initial treatment, the position of the outer sleeve 277 is adjusted (see FIG. 21C) until a change in the markings on the outer sleeve 277 is visible, as is shown in more detail in FIG. 21D. In such an embodiment, a seal or anchor between the outer sleeve 277 and the catheter 272 may be loosened and then the outer sleeve 277 moved proximally relative to the catheter 272 while the main shaft of the catheter 272 with heating element 280 remains stationary. Once the introducer sheath 282-outer sleeve 277 interface reaches the next index step transition, the seal or anchor between the outer sleeve 277 and the catheter 272 may be tightened. Such positioning advantageously provides a user with a starting point such that subsequent full indexed treatment steps can be more easily performed.

Figure 22A:
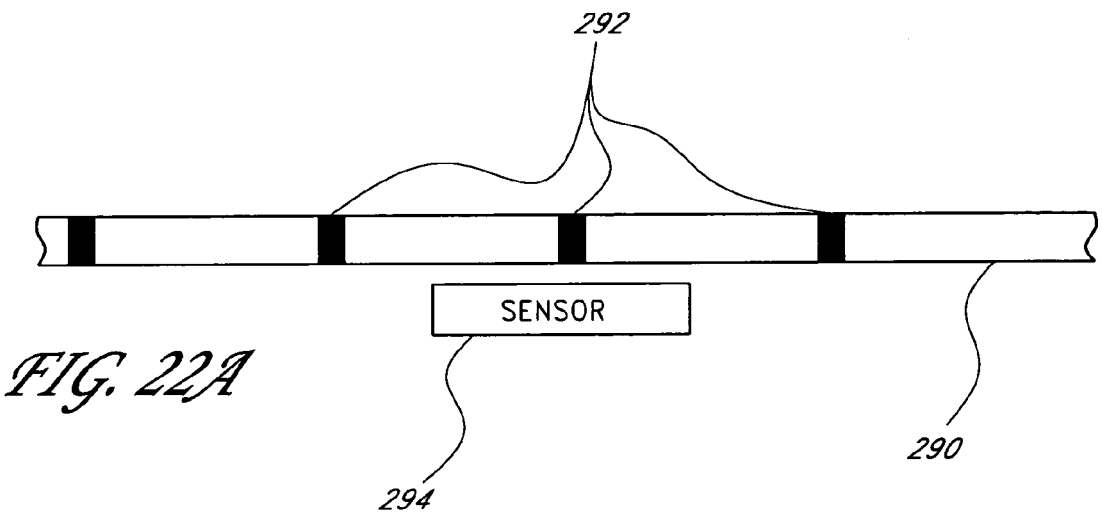
FIG. 22A illustrates an exemplary embodiment of an indexing system having a sensor configured to detect markings on a catheter shaft.

FIG. 22A illustrates an embodiment of a portion of an indexing system configured to facilitate the positioning of a heating element during each indexing step. In particular, the depicted embodiment provides automatic verification of a catheter position within a HAS without requiring manual, visual or tactile verification of the catheter position by the physician. In certain embodiments, a plurality of mechanically, electrically or magnetically detectable markings may be used to indicate to a physician or to an electronic controller system that an indexing position has been reached.

For example, as shown in FIG. 22A, a catheter shaft 290 includes a plurality of markings 292 that are detectable by a sensor 294 to determine the relative position of the catheter shaft 290. In certain embodiments, the markings 292 comprise printed magnetic ink marks that are detectable by a magnetic reading sensor. In such embodiments, the sensor 294 may be placed adjacent an introducer sheath hub and/or joined to a controller configured to produce an audible or visible alert when each magnetic marker passes underneath the sensor. This system allows for the index distance to be tracked and indicated to the physician visually and/or audibly without requiring the physician to observe the markings 292 on the catheter 290. In certain embodiments, the sensor 294 may further include an encoder, or other like circuitry, that monitors the relative position of the catheter shaft 290 and/or number of index steps performed.

Figure 22B:
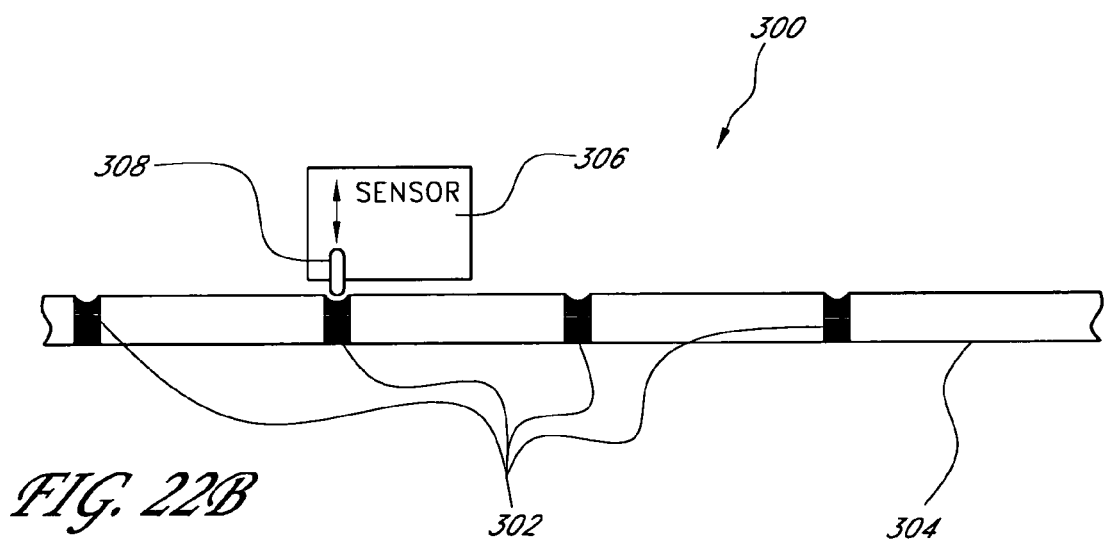
FIG. 22B illustrates another exemplary embodiment of an indexing system having a sensor configured to detect detents on a catheter shaft.

In an alternative embodiment, FIG. 22B shows a system 300 that uses a set of detents 302, or grooves, along a main body shaft of a catheter 304. A sensor 306, which is configured to detect the detents 302, is advantageously proximate the catheter main body shaft 304. For example, in certain embodiments, the sensor 306 may attach to an introducer sheath hub in order to hold the sensor 306 substantially stationary with respect to the hub. As the catheter 304 is moved proximally, a follower 308 of the illustrated sensor 306 physically "clicks" into each detent 302 that passes by the sensor 306.

In certain embodiments, the follower 308 may advantageously comprise a spring-loaded cam that provides an audible and tactile resistance indicating proper index placement. In other embodiments, the follower 308 may comprise a switch, or other like component, connected to a system controller. Such a switch may inform the system controller that the catheter 304 has been indexed to the next position. The system controller may also alert the physician that the catheter 304 is ready for treatment through audible and/or visual indicators.

FIG. 23 illustrates an embodiment of a HAS treatment system 310 having a temperature sensor 312 placed on a catheter shaft 314. In certain embodiments, the temperature sensor 312 comprises a thermocouple, a thermistor, a resistive temperature device (RTD) or a set of contacts that measures resistance. In certain embodiments, the temperature sensor 312 is positioned on the catheter 314 at a distance from a heating element 316 approximately equal to the length of an introducer sheath 318. In certain embodiments, a control system 320 may advantageously communicate with the temperature sensor 312 through wired or wireless means.

In certain embodiments, the control system 320 monitors the sensed temperature of the catheter 314 during treatment. For example, the control system 320 may monitor the sensed temperatures to determine when a treatment process has been completed. For instance, when the temperature sensor 312 detects a significant decrease in temperature relative to the patient's body temperature (such as, for example, a decrease to room temperature caused by the temperature sensor 312 leaving the HAS and entering the introducer sheath), the control system 320 alerts the physician that the treatment is complete. Such an alert may be, for example, in the form of a visible light, and audible sound and/or another alert signal.

FIG. 24 illustrates another embodiment of a HAS treatment system 330, which includes a catheter distal section 332 having two temperature sensors 334 and 336. The first temperature sensor 334 is positioned at or near a distal end 338 (e.g., approximately one centimeter from the distal end 338) of a heating element 340, and the second temperature sensor 336 is positioned at or near a proximal end 342 (e.g., approximately one centimeter from the proximal end 342) of the heating element 340. In embodiments in which the heating element 340 comprises an electrically resistive coil, one or more of the temperature sensors 334, 336 may be positioned in the coil winds, such as, for example, approximately one-half to approximately one centimeter from an end of the coil. In certain embodiments, the temperature sensors 334, 336 preferably communicate with a control system 344 configured to determine and compare the temperatures at each end of the heating element 340.

Comparison of temperatures may be advantageous in detecting heating with a portion of the heating element 340 within a sheath. For instance, for the same power input along the length of the heating element 340, a heating element portion within the sheath may rise to a higher temperature relative to the heating element portion outside the sheath. Furthermore, three or more temperature sensors may be incorporated at the catheter distal section. Alternatively, a thermocouple located proximal to the heating element may be positioned to indicate a cooler air temperature as the catheter shaft exits the introducer sheath.

In certain embodiments, the catheter 332 of FIG. 24 may be placed in a HAS at a desired initial treatment site, which can be located using any available technique. Energy can then be applied to the HAS in an initial treatment step. After the initial treatment, the catheter 332 is moved proximally, during which time the control system 344 monitors the temperatures sensed by the two temperature sensors 334, 336. In such a treatment, the section of the HAS treated in the initial step may be at a higher temperature than the surrounding portions of the HAS. A significant drop in the temperature detected by the second sensor 336 relative to the temperature detected by the first sensor 334 implies that the heating element 340 has been at least partially moved proximally out of the previously-heated region. Similarly, a significant drop in the temperature (e.g., body temperature) detected by the first temperature sensor 334 indicates that the heating element 340 has been indexed to the next adjacent treatment position. In certain embodiments, a power source may be manually activated or programmed to automatically engage power once the heating element 340 reaches its next indexed position.

In certain embodiments, by placing the temperature sensors 334, 336 between the ends 338, 342 of the heating element 340, the indexed treatments may create an overlap of adjacent treatment sections. In alternative embodiments, the temperature sensors 334, 336 may be positioned at or closer to the ends 338, 342 of the heating element 340 in order to eliminate or reduce the amount of overlap in adjacent indexing positions.

In other embodiments, rather than stopping the heating element at a discrete series of treatment positions, as described above, it is also possible to power the heating element to a target temperature at or above a minimal treatment temperature and then move the heating element along the complete treatment length of the HAS substantially without stopping the movement of the heating element while maintaining the treatment temperature. In one embodiment, the movement of the heating element may begin after an initial delay period that commences when the minimal treatment temperature is reached.

In these embodiments, the therapeutic object is to conduct treatment substantially continuously along the full length along which the HAS is to be treated. Unplanned temporary stoppages of the movement of the heating element, for example as a result of the physician becoming distracted, the patient's position becoming temporarily unfavorable, or for any other reason, are contemplated within these continuous treatment embodiments. In other embodiments, the movement of the heating element may be temporarily slowed or stopped when the temperature of the heating element deviates by a certain amount from the target temperature. In a further embodiment, this deviation amount is 10 degrees Celsius or less, and may be approximately 3 degrees Celsius in another embodiment.

In one embodiment, the treatment temperature is an internal temperature of the heating element, or is a temperature measured at or adjacent to the heating element. In one embodiment, the minimal treatment temperature is the temperature required to cause a durable reduction of the diameter of the HAS, or to cause an absence of patency in the HAS. This minimal treatment temperature may be within a range of 80-140 degrees Celsius, and may be, for example, approximately 120 degrees Celsius or approximately 95 degrees Celsius. Other minimal treatment temperatures are contemplated, and may be appropriately set by one of skill in the art depending on the conditions of use and the desired therapeutic outcome.

In another embodiment, power is applied to the heating element within a treatment power level range while the heating element is moved along the treatment length of the HAS. In a further embodiment, the treatment power level range is 20-40 W.

In one embodiment, the heating element may be elongated along its longitudinal axis, and the treatment length of the HAS is greater than the length of the heating element in the direction of movement. In a further embodiment, the heating element has a length that is at least fifteen times its width. In another embodiment, the heating element has a length that is at least ten times its width. In another embodiment, the heating element has a fixed profile in a plane orthogonal to a longitudinal axis thereof.

In a further embodiment, the treatment method also contemplates passing fluid through a lumen of the catheter to which the heating element is coupled, thus heating the fluid, which then exits at the catheter tip. The fluid may be saline, a venoconstrictor, sclerosant, high-impedance fluid, physiologic tissue adhesive, hydrogel, combinations of the same or the like. The heating element may extend to the distal end of the catheter. Furthermore, in one embodiment, the heating element may be a coil with a varying pitch and/or spacing. The varying pitch or spacing may be advantageously used to vary the heat output over the axial length of the resistive element, for example in order to compensate for the cooling effect of the fluid flow and maintain the treatment temperature, to provide a greater treatment temperature at certain areas of the coil for therapeutic reasons, or for any other reason known in the art. In one embodiment, the coil pitch is varied so as to provide a higher temperature at the proximal and distal end of the treatment length of the HAS.

In a further embodiment, laser light is applied to the HAS from the catheter to further reduce the patency of the HAS. In a further embodiment, the light is applied from the distal end of the catheter. The laser light may be generated by any means known to those of skill in the art. For example, a 980 nm diode laser may be employed, although generation of laser light having other wavelengths, for example, within a range of 700-1100 nanometers, is also contemplated.

Figure 25A:
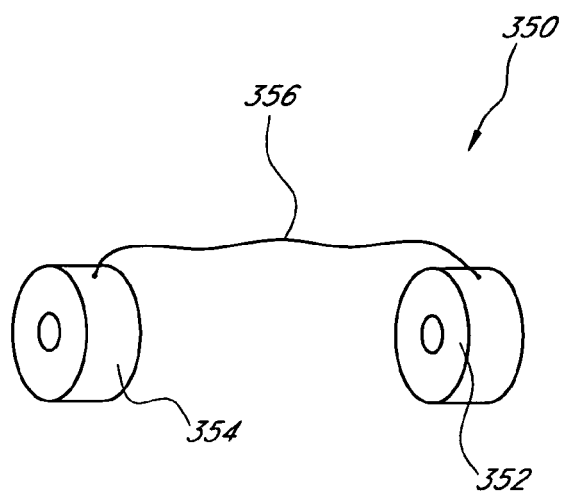
FIGS. 25A and 25B illustrate an exemplary embodiment of an indexing device usable for facilitating manual indexed movement of a catheter.
Figure 25B:
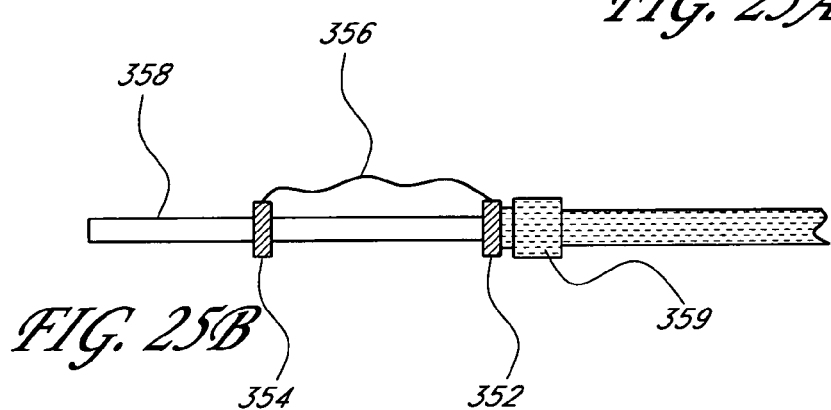

FIGS. 25A and 25B illustrate embodiments of an indexing device 350 usable with systems configured to facilitate regular indexing movements of a catheter. For example, certain embodiments of the device 350 may facilitate reproducible movement of a catheter from a first position a subsequent indexed position.

As illustrated in FIG. 25A, the indexing device 350 includes a pair of o-ring type donuts 352 and 354 configured to be movably positionable on a catheter shaft. The donuts 352 and 354 are joined together through a connector 356, such as a string. In other embodiments, the donuts 352 and 354 may be connectable through other flexible and/or collapsible devices such as, for example, wires, springs, and the like.

As further illustrated in FIG. 25B, in certain embodiments, during use the first donut 352 is positioned on a catheter 358 proximate an introducer sheath hub 359. In certain embodiments, the first donut 352 is manually held against the introducer sheath hub 359. Alternatively, the first donut 352 may be configured to have an interference fit or a mechanical luer lock fit to physically and/or mechanically attach to the introducer sheath hub 359.

The second donut 354 is preferably permitted to move axially along the length of the catheter 358. In certain embodiments, the second donut 354 is further capable of gripping the catheter 358 to move the catheter 358 axially as the second donut 354 is moved toward the first donut 352. For example, the second donut 354 may comprise a flexible or semi-flexible material that allows a user to squeeze or apply pressure to the second donut 354 to grip the catheter 358 extending therethrough.

In certain embodiments, at least one of the donuts 352, 354 comprises an elastic material. For example, at least one of the donuts 352, 354 may comprise silicone, KRATON®, urethane, combinations of the same or the like. Such materials may advantageously allow the donut to be pushed onto the catheter shaft and to have an interference fit in order to help anchor the donut in place until it is manually moved.

In certain embodiments, the device 350 is used to adjust the position of the catheter 358 during the treatment of a section of a HAS. For example, once the catheter 358 is placed in its initial position such that a corresponding therapeutic element (e.g., heating element) is located at a desired initial treatment site, both donuts 352, 354 are placed adjacent (such as by sliding at least one of the donuts 352, 354) the introducer sheath hub 359. At that point, the initial treatment process is performed.

Next, the catheter 358 is repositioned for the second treatment process. In certain embodiments, the second donut 354 is used to grip the catheter shaft 358 and both are moved in tandem away (proximally) from the first donut 352 and introducer sheath hub 359 until the movement of the second donut 354 and catheter shaft 358 is arrested, or stopped, by the connector 356. At this point, a therapeutic element of the catheter 358 is preferably in a new adjacent section for the second treatment.

In certain embodiments, the connector 356 is preferably of a length that corresponds to the length of the desired indexing step. For example, in certain embodiments, the length of the connector 356 may be substantially the same as the length of the corresponding therapeutic element. In yet other embodiments, the length of the connector 356 may be shorter than the length of the therapeutic element such that successive indexed treatments have a partial overlap. In yet other embodiments, the length of the connector 356 may be adjustable to facilitate use of the device 350 with different catheters having different sized therapeutic elements or to facilitate the adjusting of the length of each treated portion.

Figure 26A:
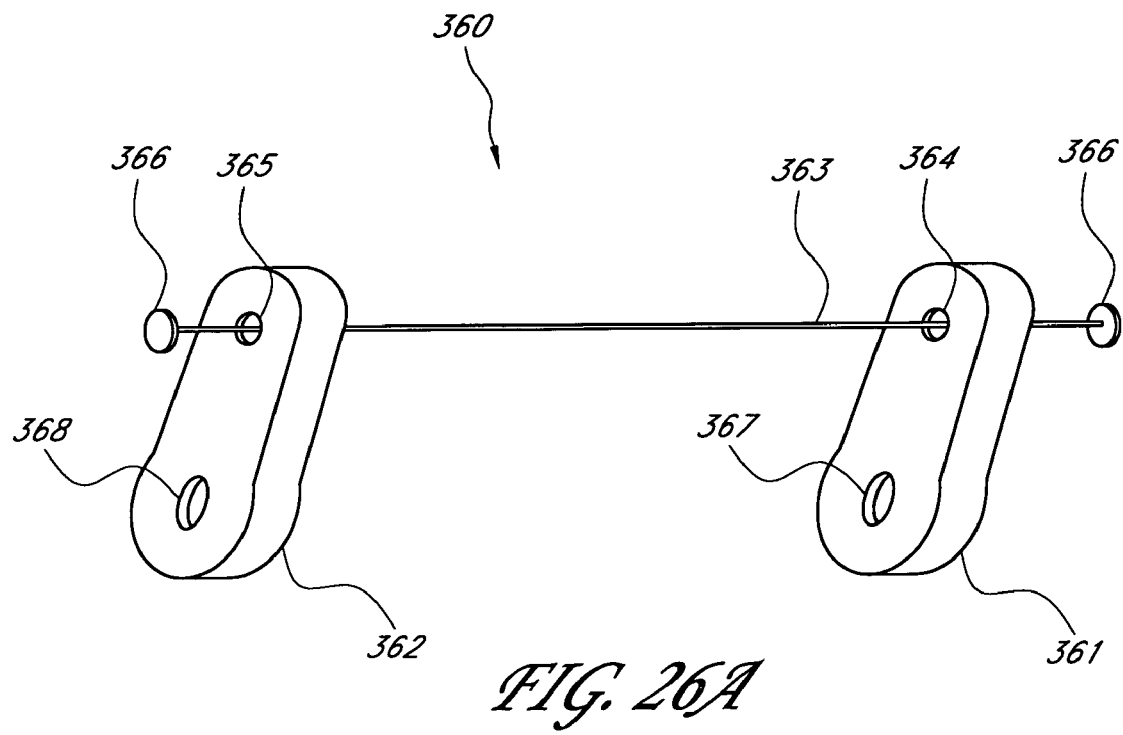
FIGS. 26A and 26B illustrate other exemplary embodiments of indexing devices usable for facilitating manual indexed movement of a catheter.
Figure 26B:
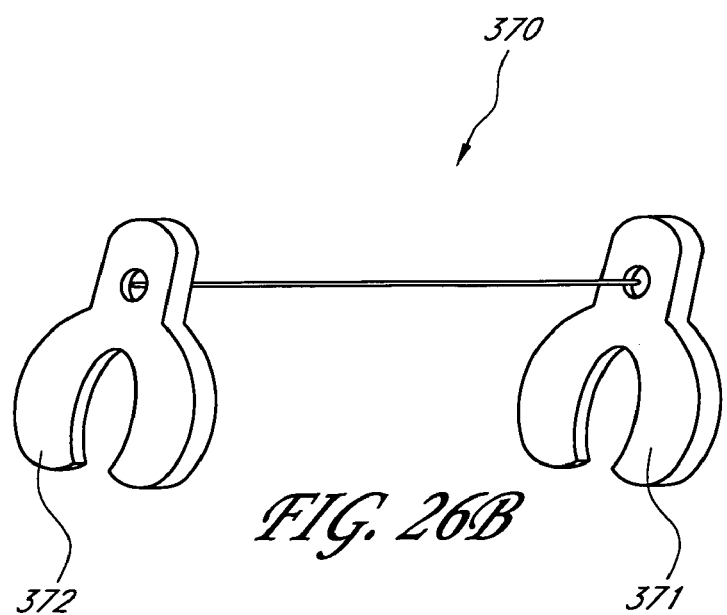

FIGS. 26A and 26B illustrate alternative embodiments of indexing devices usable with systems configured to facilitate regular indexing movements of a catheter. In particular, FIG. 26A illustrates an indexing device 360 having a pair of elongated rings 361 and 362 connected by a rigid sliding rod 363. In the illustrated embodiment, the rod 363 extends through openings 364 and 365 of the rings 361 and 362, respectively, and is preferably configured to limit relative axial movement between the first ring 361 and second ring 362 beyond a predefined distance. As shown, the rod 363 further comprises stops 366 at opposing ends of the rod 363 that are configured to limit travel of the first and second rings 361, 362. In particular, the stops 366 comprise a disk-shaped head and are advantageously of a larger size than the openings 364 and 365 such that the openings 364, 365 cannot easily pass over the stops 366.

As shown in FIG. 26A, the rings 361 and 362 further comprise catheter openings 367 and 368, respectively, that allow for a corresponding catheter to pass therethrough. Use of the indexing device 360 is similar to the use of the indexing device 350 described with reference to FIGS. 25A-25B. That is, the elongated rings 361, 362 are used similarly to the donuts 352, 354 to move a catheter shaft a predefined distance, which distance is determined by the length of the rod 363.

FIG. 26B illustrates an alternative embodiment of an indexing device 370 that includes first and second rings 371 and 372 having a wish-bone like shape. In such an embodiment, the legs of at least one of the rings 371, 372 may fit around the surface of a catheter shaft. In certain embodiments, such a configuration advantageously allows a user to more easily slide at least one of the rings 371, 372 along the catheter shaft and to remove the device 370 from the catheter shaft.

In certain embodiments, at least one of the rings 371, 372 comprises an elastic material. For example, at least one of the rings 371, 372 may comprise silicone, KRATON®, urethane, combinations of the same or the like. Such materials may advantageously allow the ring to be pushed onto the catheter shaft and to have an interference fit in order to help anchor the ring in place until it is manually moved. In certain embodiments, the rings 371 and 372 may be connectable by a sliding rod, a string, or other like device as described in more detail above.

Figure 27:
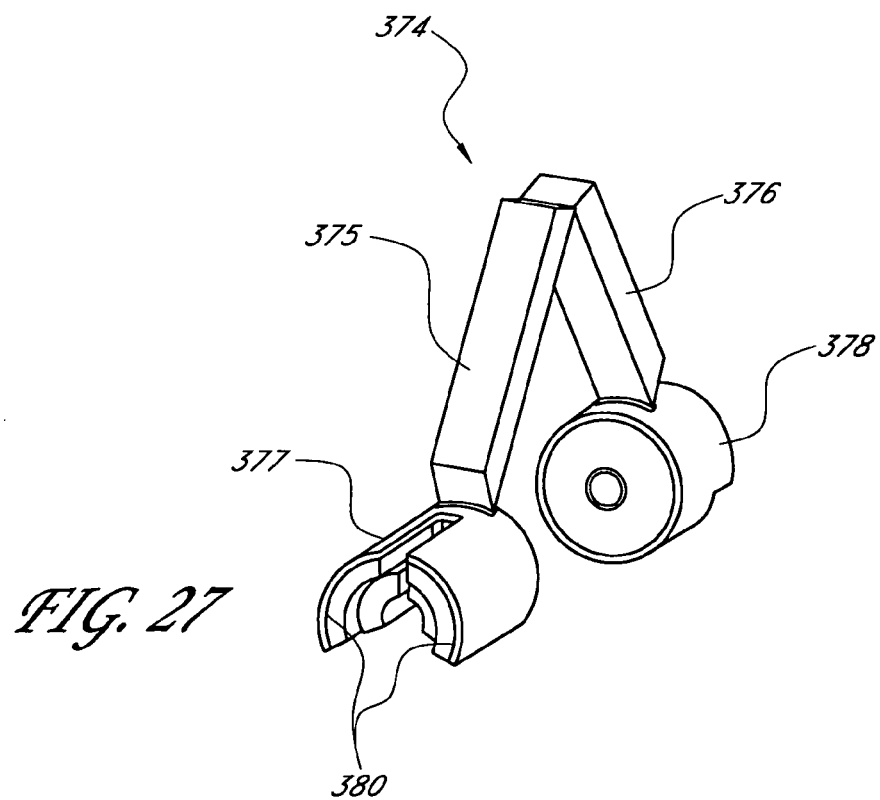
FIG. 27 illustrates an exemplary embodiment of an indexing device having linkage arms usable for facilitating indexed movement of a catheter.
Figure 28B:
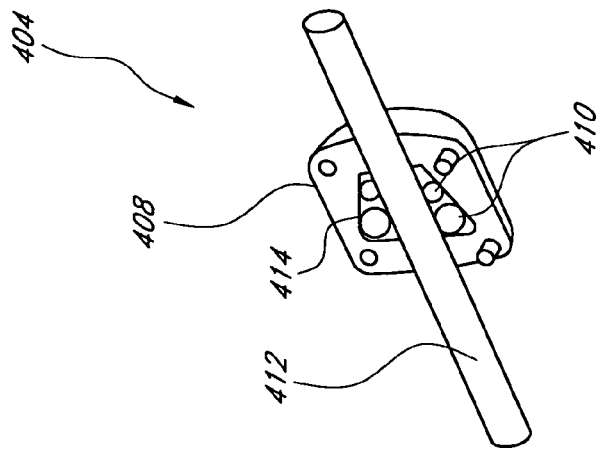
FIGS. 28A and 28B illustrate other exemplary embodiments of an indexing device having linkage arms usable for facilitating indexed movement of a catheter.
Figure 28A:
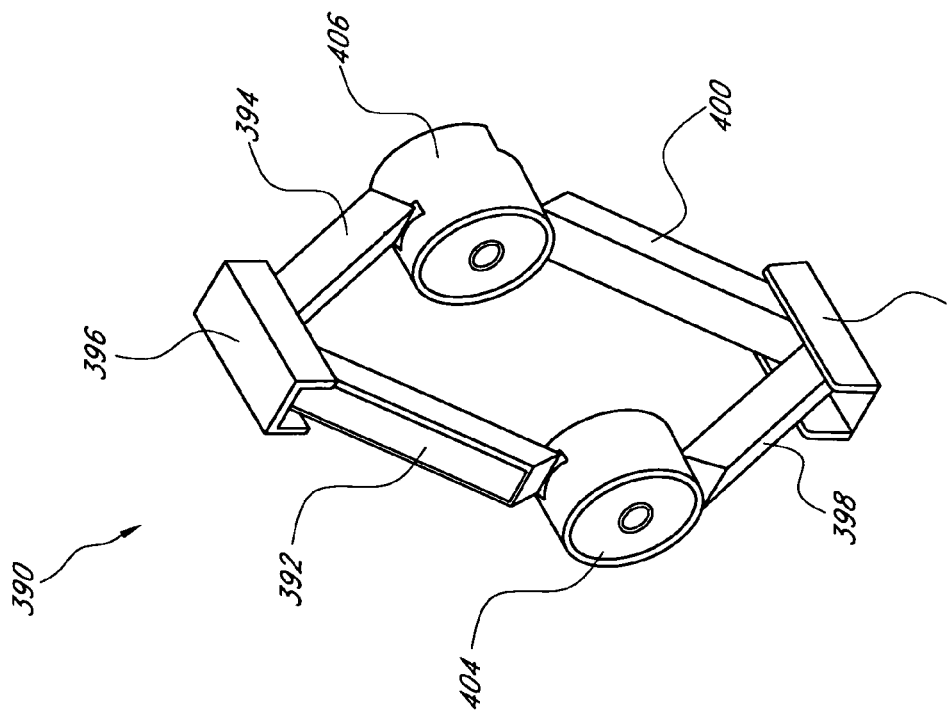

FIGS. 27, 28A and 28B further illustrate embodiments of indexing devices employing various linkages to index a catheter by a desired amount. FIG. 27 illustrates an indexing device 374 comprising a linkage with two arms 375 and 376. In certain embodiments, the linkage arms 375, 376 are of substantially equal length and are hingedly joined together at one end. In certain embodiments, the range of movement of the linkage arms 375, 376 is from approximately 0 degrees (e.g., the arms 375, 376 extending in parallel directions) to approximately 180 degrees (e.g., the arms 375, 376 fully extended). In certain embodiments, the range of motion of the arms 375, 376 may be limited by attached cylindrical ends 377 and 378 coming together (e.g., at approximately 0 degrees) and when the linkage arms 375, 376 are in tandem.

As shown, the first linkage arm 375 is connected to the cylindrical end 377, and the second linkage arm 376 is connected to the cylindrical end 378. In certain embodiments, the first and second cylindrical ends 377, 378 are configured to anchor the indexing device 374 to a catheter shaft. For example, the second cylindrical end 378, which may be hingedly attached to the linkage arm 376, may be configured to attach to an introducer sheath hub associated with a catheter.

In certain embodiments, the first cylindrical end 377 comprises a grip structure 380 that is hingedly attached to the linkage arm 375. For example, the grip structure 380 may allow the first cylindrical end 377 to selectively maneuver along a catheter. In certain embodiments, the grip structure 380 is configured to straddle a catheter shaft. As shown, the grip structure 380 may comprise an open section that allows reception of the catheter therein without the need for threading the catheter through the center of the grip structure 380. The open section advantageously includes two tab-like extensions that a user may pinch (such as with a thumb and a forefinger) to capture the catheter shaft. In certain embodiments, the inner radial surface of the grip structure 380 may comprise, for example, a soft tacky type of silicone or KRATON®.

In certain embodiments, during use, the indexing device 374 is coupled to a catheter shaft such that the catheter shaft extends through both the ends 377, 378. Prior to an initial treatment, the end 378 is moved along the catheter shaft and brought proximate an introducer hub, and the end 377 is moved adjacent the end 378. After treatment of the section has been completed, the user grips the end 377 and draws out the catheter until the device 374 is in a fully extended position (e.g., the legs 375 and 376 are in line). Such a full extension preferably corresponds to the index treatment length. The user then loosens the grip of the end 377 on the catheter shaft and moves the end 377 proximate the end 378. At this point, a second treatment may be performed and the process is repeated as appropriate.

In certain embodiments, the indexing device 374 may further comprise a spring or elastic component (not shown) further linking the two linkage arms 375 and 376 to keep the device 374 in a preferred position when not in use. For example, such a preferred position may include the grip structure 380 being located adjacent to the second cylindrical end 378 and a corresponding introducer sheath hub.

FIG. 28A illustrates another embodiment of an indexing device 390 similar to the indexing device 374 of FIG. 27. As shown, the indexing device 390 comprises two sets of arms. In particular, the indexing device 390 comprises a top set of arms 392 and 394 that are hingedly connected by a first connector 396. The illustrated indexing device 390 further comprises a bottom set of arms 398 and 400 that are hingedly connected by a second connector 402.

The indexing device 390 also includes a first anchor 404 that is hingedly connected to the first top arm 392 and the first bottom arm 398. Likewise, a second anchor 406 hingedly couples the second top arm 394 and the second bottom arm 400. In certain embodiments, the second anchor 406 comprises a structure similar to the cylindrical end 378 of FIG. 27 and is configured to attach to, or be included as part of, an introducer sheath hub.

In certain embodiments, at least one of the sets of linkage arms 392, 394 and 398, 400 may also include a spring or elastic component to keep the indexing device 390 in a preferred, or default, position when not in use. In certain embodiments, the preferred position may include the first and second anchors 404 and 406 substantially adjacent to an introducer sheath hub.

In certain embodiments, the two linkage arms sets are preferably made of two structures of substantially equal length. For example, all four linkage arms 392, 394, 398 and 400 may be of a substantially equal length, with each pair being hingedly attached together. In certain embodiments, the range of movement of each hinged pair of arms is preferably from approximately 0 degrees to approximately 180 degrees. In other embodiments, the range of movement of the hinged arms of the device 390 may be limited to narrower ranges as desired.

In certain embodiments, the first anchor 404, includes a grip structure that is hingedly attached to arms 392 and 398. FIG. 28B illustrates further details of inner components of the first anchor 404. In particular, FIG. 28B illustrates a portion of a housing 408 of the first anchor 404. Within a housing 408 are two rings 410 usable, for example, to grip a catheter shaft 412 extending through the first anchor 404. In certain embodiments, the two rings 410 may provide an interference fit on the catheter shaft 412. When the first anchor 404, for example, is moved away from an introducer sheath hub, the rings 410 may be moved toward a tapered inner surface 414 of the housing 408, which may cause the rings 410 to tighten their fit on the catheter shaft 412. In certain embodiments, the tapered inner surface 414 may be of an angle to accommodate two rings of different sizes, a single ring, or more than two rings, for improved gripping forces on the catheter shaft 412.

In certain embodiments, the first connector 396 and second connector 402 advantageously facilitate movement of the indexing device 390. For example, a user may press on one or both of the connectors 396, 402 to extend the indexing device 390 such that the angles between the sets of arms increase. Use of the indexing device 390 may be similar to the method of use described with reference to the indexing device 374 of FIG. 27.

Figure 29A:
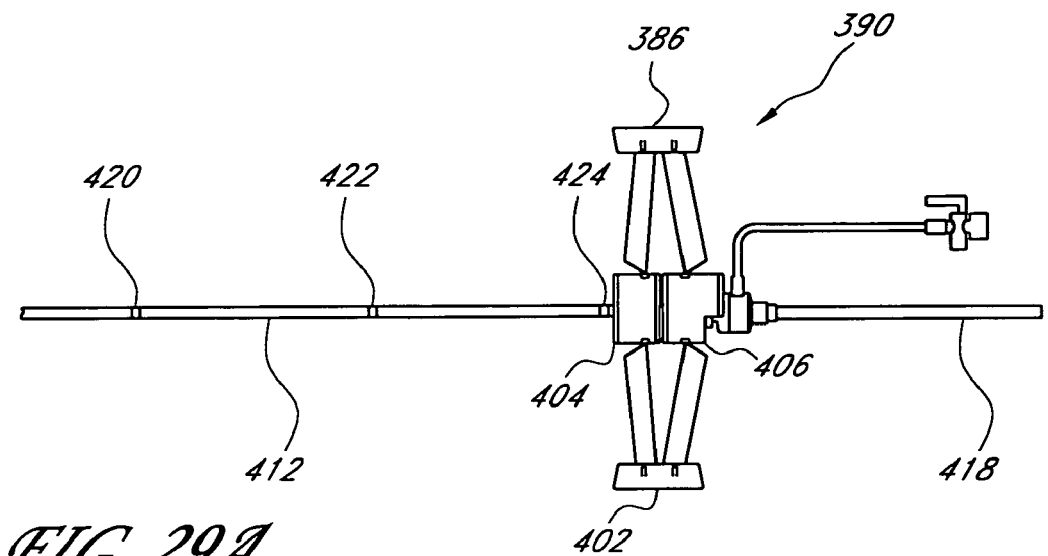
FIGS. 29A-29E illustrate a method of using the indexing device of FIG. 28A to perform an indexed movement of a catheter during a treatment process.

FIGS. 29A-29E illustrate one method of use of the indexing device 390. For example, a single indexing step during a treatment process. In FIG. 29A, the indexing device 390 is in a default or "zero point" position and is located on the catheter shaft 412 such that the catheter shaft 412 extends though the first and second anchors 404 and 406 of the indexing device 390. The first anchor 404 is located proximate the second anchor 406, which is adjacent a hub of an introducer 418. In certain embodiments, the "zero point" position corresponds to the position and/or configuration of the indexing device 390 during treatment of a patient.

FIG. 29A further illustrates the catheter shaft 412 including several markings, including a first mark 420, a second mark 422 and a third mark 424. As shown, the first anchor 404 of the indexing device 390 is substantially aligned with the third mark 424 on the catheter shaft 412.

Figure 29B:
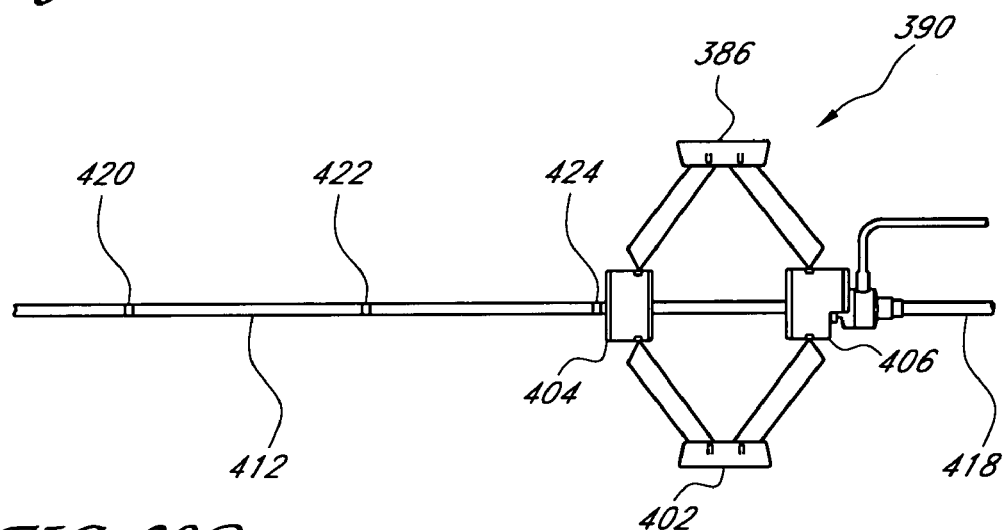

FIG. 29B illustrates the position of the indexing device 390 during an indexing step. In particular, FIG. 29B illustrates the indexing device 390 being in a partially extended position as a result of pressure being applied to one or both of the connectors 396, 402. As the user presses one or both of the connectors 396, 402, the hinged arms of the indexing device 390 begin to extend radially (i.e., the angles between each set of arms increases), and the first anchor 404, which advantageously grips the catheter 412, draws the catheter 412 from the introducer 418.

Figure 29C:
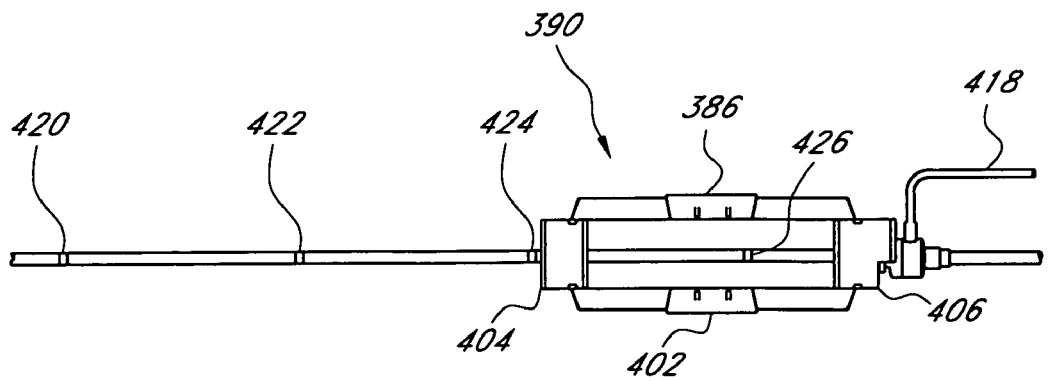

FIG. 29C illustrates the indexing device 390 in a fully extended position such that the pairs of legs each have approximately a 180 degree angle therebetween. In FIG. 29C, a fourth mark 426 along the catheter shaft 412 also becomes visible as it is drawn from the introducer 418.

Figure 29D:
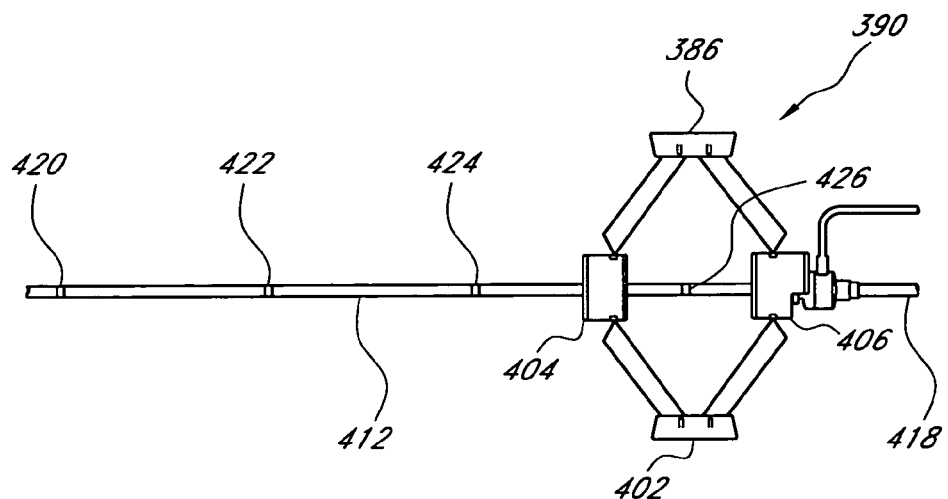

FIG. 29D illustrates a configuration of the indexing device 390 as it returns to the "zero point" position. In particular, during this return state, the first anchor 404 releases its grip on the catheter 412 and slides toward the second anchor 406. Thus, the catheter 412 remains substantially stationary during the indexing device's return to the "zero point" position. In certain embodiments, an elastic or spring-like mechanism causes the indexing device 390 to automatically return to the "zero point" position once pressure is released from one or both of the first and second connectors 396 and 402.

Figure 29E:
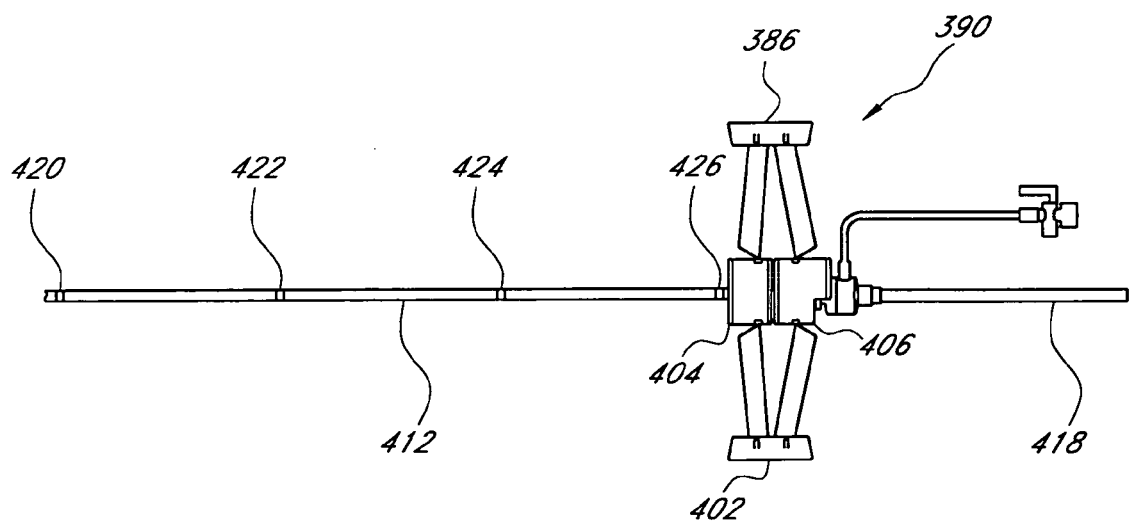

FIG. 29E illustrates the final state of a single indexing step during a treatment process. In particular, the indexing device 390 is returned to the "zero point" position. Furthermore, the first anchor 404 is substantially aligned with the next catheter mark (i.e., the fourth mark 426). At this point, a second indexed treatment may be performed.

Figure 30A:
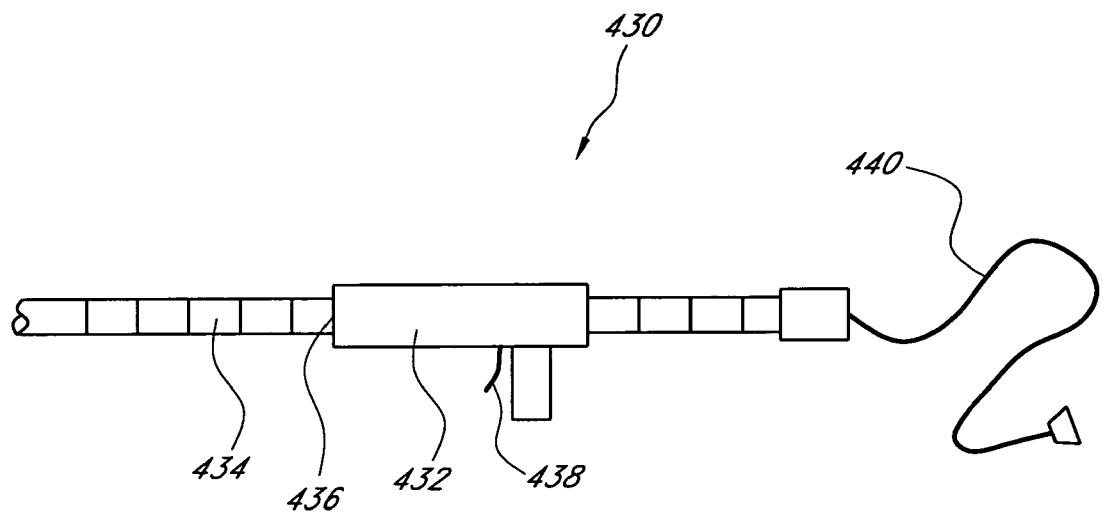
FIGS. 30A and 30B illustrate exemplary embodiments of automatic indexing systems including a mechanical indexing handle.

FIG. 30A illustrates another embodiment of an indexing system 430 that comprises a mechanical indexing handle 432. In certain embodiments, the indexing handle 432 is threaded over a main body of a catheter 434. In certain preferred embodiments, the indexing handle 432 is removable from the catheter 434.

As shown, the illustrated indexing handle 432 further comprises a distal end 436 that may be configured to securely attach to a hub of an introducer sheath. The indexing handle 432 further includes a trigger 438, the activation of which causes a corresponding movement of the catheter 434 through the indexing handle 432. For example, the indexing handle 432 may be configured to incrementally move proximally the main body of the catheter 434 a set distance relative to the introducer sheath hub.

In certain embodiments, a catheter cable 440 extends from the catheter 434 and is configured to communicate with a remote generator. For example, the generator may provide energy to the catheter 434 to activate a therapeutic element associated therewith.

In certain embodiments, the indexing handle 432 has a set trigger travel or a set index distance. As the trigger 438 is activated, a gripping mechanism within the indexing handle 432 grasps the catheter 434 and moves the catheter 434 in a proximal direction relative to the indexing handle 432, which preferably remains stationary. At the end of the incremental movement of the catheter 434, the inner mechanism of the indexing handle 432 then releases the catheter 434 and returns to an initial position, such as a "zero point" position, within the indexing handle 432.

In certain embodiments, the inner gripping mechanism comprises a structure similar to the structures described with reference to FIG. 28B. In yet other embodiments, the inner gripping mechanism of the indexing handle 432 comprises a cam-action component that is pushed against the main body of the handle 432 as the component starts to pull the catheter 434 and then is released at the end of the travel or index distance. In certain embodiments, motive force for the catheter movement may be provided by a motor-driven worm gear, a pneumatic piston, or other means.

Figure 30B:
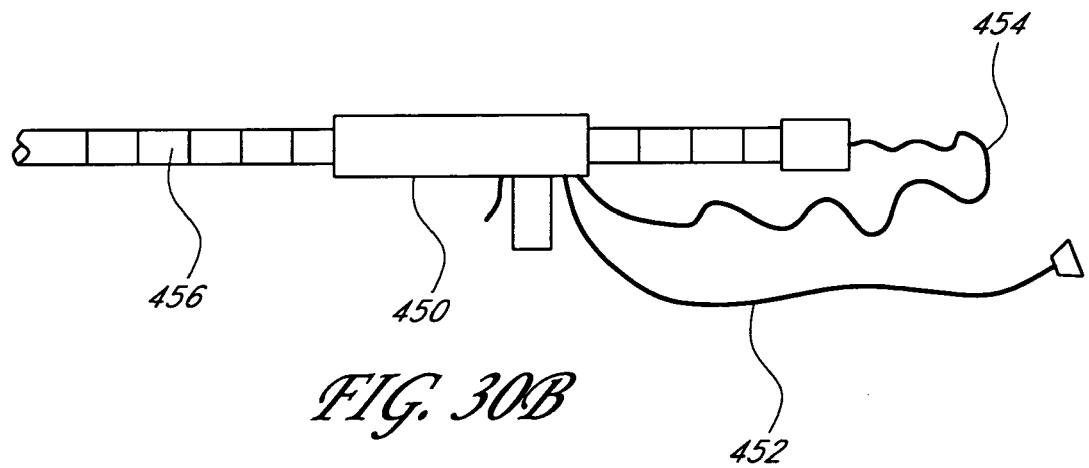

Another embodiment of an index handle 450 is illustrated in FIG. 30B. As shown, the index handle 450 comprises a first cable 452 and a second cable 454. In certain embodiments, the first cable 452 extends to a remote generator capable of supplying energy to the catheter 456. The second cable 454 may extend from the indexing handle 450 to a catheter 456.

In certain embodiments, the indexing handle 450 may include one or more switches or controls for controlling power supplied by the generator to the catheter 456. For example, the indexing handle 450 may include an ON/OFF button to remotely control the power from the generator during treatment. In certain embodiments, the indexing handle 450 may comprise a switch that signals the generator to power up or power down.

Figure 31A:
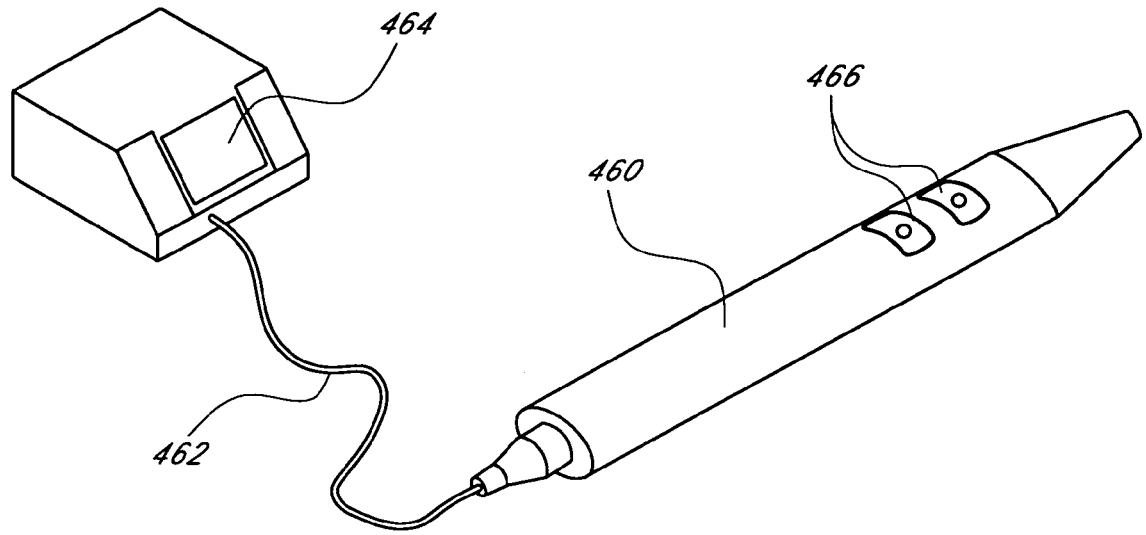
FIGS. 31A-31D illustrate exemplary embodiments of indexing systems having controls and/or a remote device to control power applied by a therapeutic element during a treatment process.

FIGS. 31A-31D illustrate several embodiments that include a remote switch usable to control the supplying of energy to a catheter. In particular, FIG. 31A shows a catheter handle 460 connected through a cable 462 to a generator 464. The handle 460 further comprises a set of buttons 466 usable to control energy supplied by the generator 464. Although two buttons are shown for exemplary purposes, one or more buttons may be incorporated on the handle 460.

Figure 31B:
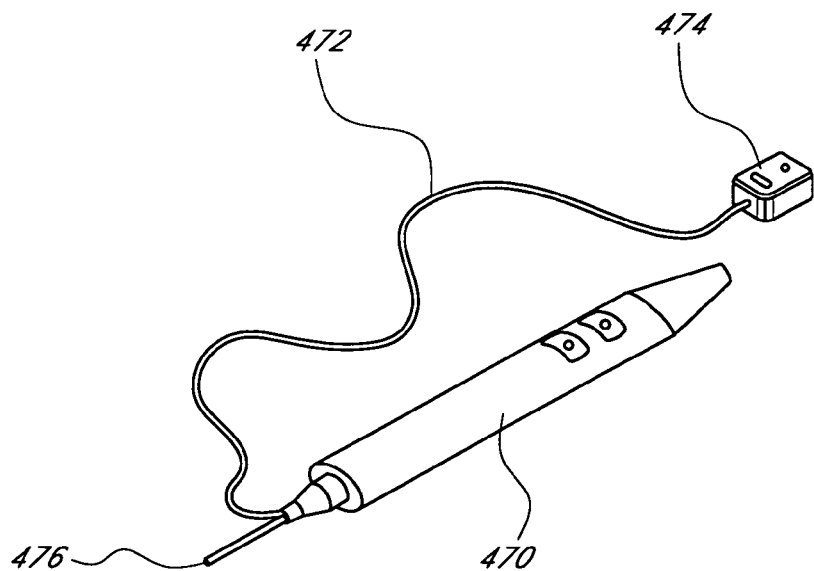

FIG. 31B illustrates an alternative embodiment wherein a catheter handle 470 is coupled through a cable 472 to a remote switch 474 separate from the handle 470. In certain embodiments, the cable 472 and a cable 476 from the generator couple to the catheter handle 470. The remote switch 474 and/or switches on the handle 470, for example, may be used to control the associated generator.

Figure 31C:
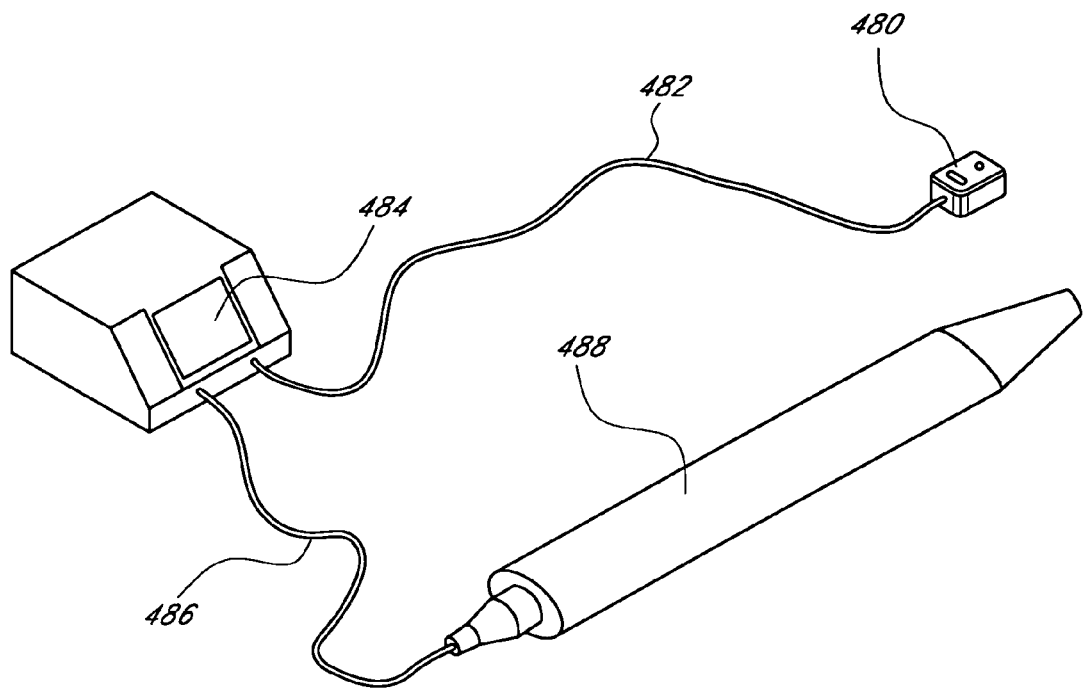
Figure 31D:
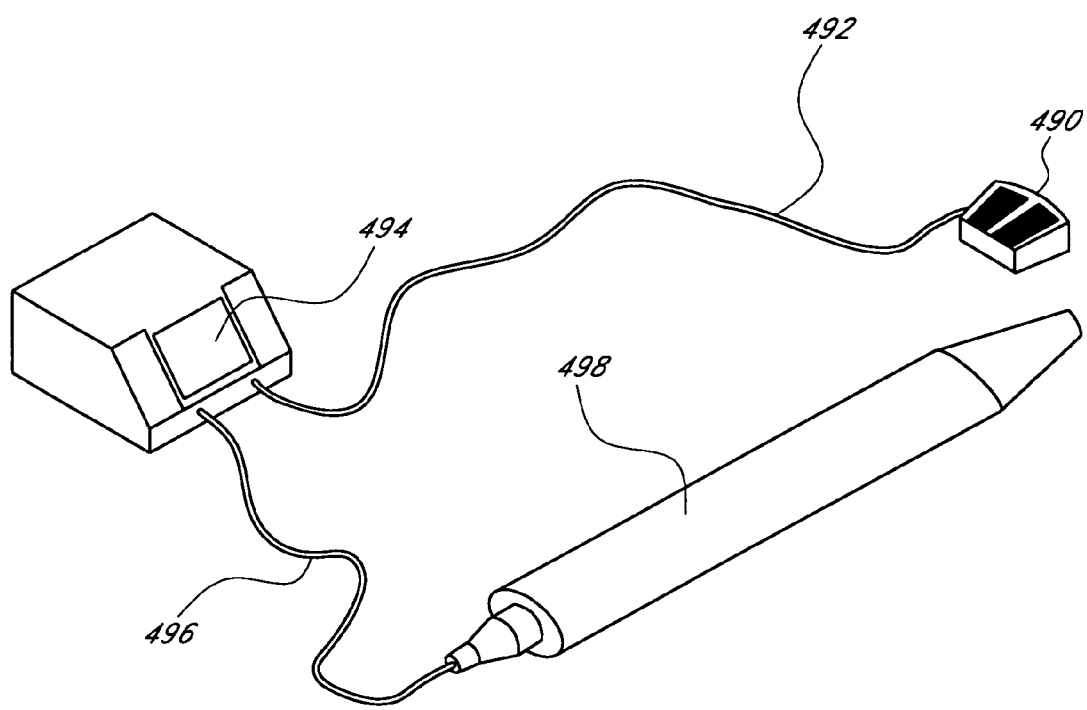

FIG. 31C illustrates yet another embodiment showing a remote switch 480 directly coupled through a cable 482 to a power generator 484. Also shown is a separate cable 486 coupling the generator 484 to an indexing handle 488. FIG. 31D illustrates a similar embodiment wherein a remote foot switch 490 is directly coupled through a cable 492 to a generator 494. Also shown in FIG. 31D is a second cable 496 coupling the generator 494 to an indexing handle 498.

Although described with reference to particular embodiments, other configurations for indexing systems may be used for a treatment process of a HAS. For example, communication between an indexing device and a generator may take place through wired or wireless (e.g., radio frequency) communications. In certain embodiments, communications between one or more switches and/or controls may take place through wired or wireless communication channels.

Figure 32:
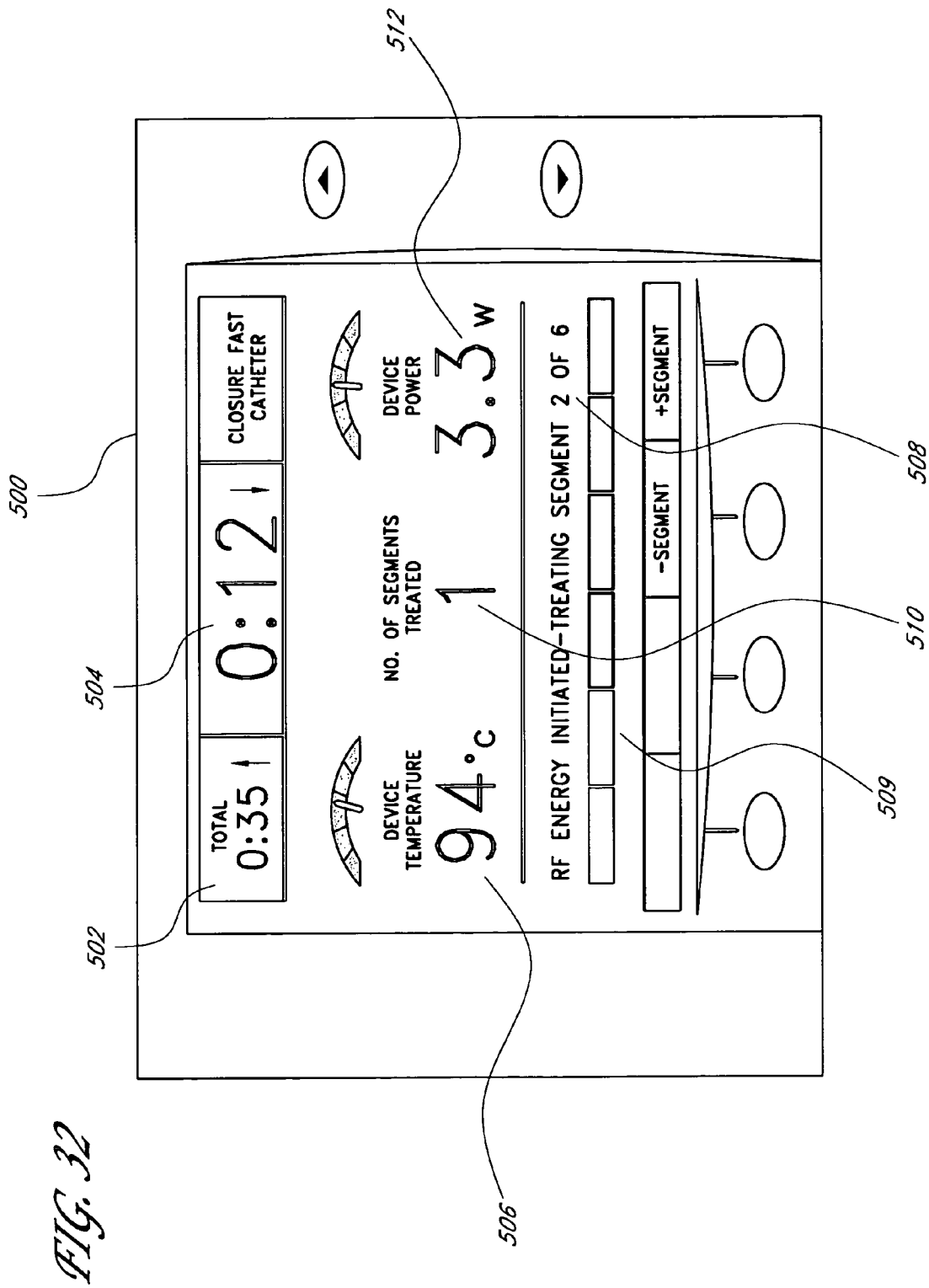
FIG. 32 illustrates a screen shot of an exemplary embodiment of a control system display usable with an indexing system.

FIG. 32 illustrates an embodiment of screen shot of an interface 500 of an electronic control system usable with embodiments of indexing systems disclosed herein. In certain embodiments, software of the control system determines the length and/or number of index steps performed and/or to be performed based on the information input by the user. For example, relevant information may include, but is not limited to, the length of the inserted portion of the catheter and the overall length of the introducer sheath from its tip to the back end of the hub. Appropriate software modules may then be used to determine the length of an index step so that successive treatments can overlap.

As shown, the illustrated interface 500 includes multiple display components to provide a user with information concerning a treatment process and input devices for receiving information from a user. In particular, the interface 500 includes a total elapsed time display 502 that indicates how much time has passed since the beginning of the procedure. An index elapsed time 504 indicates the amount of time passed for a particular index treatment.

A temperature display 506 provides the temperature of the current treatment, and an index step display 508 and a progress display 509 indicate which step is currently being performed with respect to the entire treatment process. In certain embodiments, information for one or both of the index step display 508 and progress display 509 is determined by a controller using physician input relating to the length of the catheter portion inserted into the introducer and/or the length of the introducer sheath.

Although the interface 500 is depicted with reference to a particular embodiment, various other displays and/or input devices may be used. Furthermore, not all display components depicted in FIG. 32 need be part of the interface 500.

Figure 33:
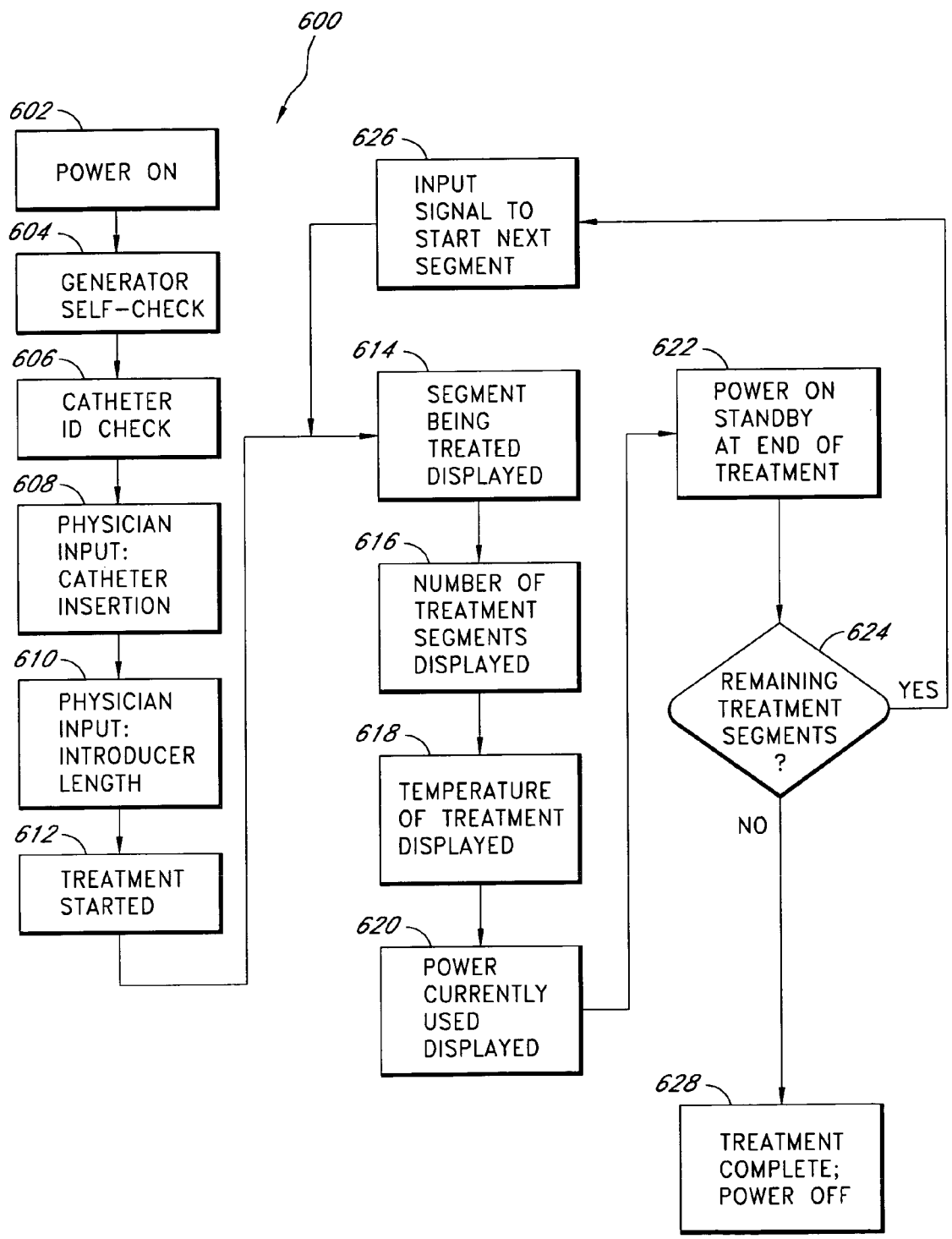
FIG. 33 illustrates an exemplary flowchart of an indexed treatment process.

FIG. 33 illustrates a general flowchart of an indexing treatment process 600, according to one embodiment. In certain embodiments, the process 600 is carried out, at least in part, by one of the indexing systems described previously herein.

As illustrated, the process 600 begins at Block 602 by powering on an indexing treatment system. At Block 604, a generator of the indexing system performs a self-check to determine, among other things, if the generator is in proper condition to perform a treatment. At Block 606, the catheter is coupled to the generator and a catheter identification check is performed to associate the proper software to the treatment catheter. For example, a physician may visually verify that the correct catheter has been selected, or such verification may be performed automatically by a control system, such as by electronically reading a tag associated with the catheter.

At Block 608, a physician inputs data into the control system indicating that the catheter has been inserted into a HAS of a patient. Alternatively, the catheter and/or software may sense body temperature as an indication that the device has been inserted into the body. In certain embodiments, the physician inputs the length of the inserted portion of the catheter. In other embodiments, the physician may input a specific catheter marking that is initially aligned with a introducer sheath associated with the catheter.

At Block 610, the physician inputs into the control system the length of the introducer sheath. At Block 612, the treatment process begins. In certain embodiments, a therapeutic element, such as a heating element, of the catheter is energized through the use of at least one power generator. For example, the therapeutic element may treat a section of the HAS through heat, RF energy, or the like.

Following Block 612, Blocks 614, 616, 618, and 620 may be performed concurrently or substantially concurrently. At Block 614, an identification of the specific segment being treated is displayed to the user. For example, the control system may correlate a first segment with a number "1" and display this number to the user, such as in a manner described with reference to the display illustrated in FIG. 32. At Block 616, an identification of the number of treated segments is displayed. At Block 618, a temperature of the current treatment is displayed. At Block 620, the power being currently used during the treatment is displayed.

After the treatment for the specific segment has completed, the process 600 proceeds with Block 622. At Block 622, the process 600 causes the generator to enter a standby mode such that little or no power is applied to the therapeutic element of the catheter. The process 600 then determines at Block 624 whether there are remaining segments of the HAS to be treated. If there are segments that remain to be treated, the process 600 proceeds with Block 626, wherein the therapeutic portion of the catheter is moved to the next segment and an input signal is provided to the control system to begin the next indexed treatment. For example, in certain embodiments, one of the indexing devices described previously herein is used to adjust the catheter position between successive indexing treatments. If there are no segments remaining to be treated, the process 600 proceeds with Block 628, wherein the physician powers down the generator.

Although the process 600 has been described with reference to particular embodiments, the process 600 may be performed without executing all the blocks illustrated in FIG. 33, or some of the illustrated blocks may be modified. For example, either or both of Blocks 608 and 610 may be performed automatically by the control system. For instance, in certain embodiments, the control system may monitor the length of the catheter portion inserted into the HAS.

In addition, the order of the blocks illustrated in FIG. 33 may be modified in other embodiments. For example, the process 600 may perform any combination of Blocks 614, 616, 618 and 620 simultaneously or in any order to provide the user with the pertinent information relating to the treatment process.

Certain methods of using an indexing HAS treatment system will now be described. The methods described herein can employ any suitable device described above or otherwise known to the skilled artisan. In the methods described below, the direction "distal" or "proximal" will generally refer to the catheter orientation, wherein "distal" is toward the catheter end inserted into the body and "proximal" is toward the end the user holds during operation.

For example, in certain embodiments, an indexing method may comprise inserting a heating element with a length of about five to about seven cm into a distal-most section of a HAS to be treated. For instance, for a saphenous vein, where the catheter is advanced antegrade from the knee area to the groin area, the catheter-distal direction is limb-proximal).

The heating element is then aligned with the starting treatment location within the HAS. In certain embodiments, a tumescent solution may be injected to surround and compress the HAS (assisting in evacuation of fluid from within the HAS, providing a thermal heat sink to protect surrounding tissue, and providing anesthetic to the surrounding tissue). Compression of the HAS, such as through manual compression by the physician, may also be performed.

Power is then be applied to the heating element for a desired length of time to treat the segment of the HAS adjacent to the heating element. After a desired dwell time, the power supply to the heating element can be reduced or shut off. With the power off (or substantially reduced), the heating element may then be indexed proximally (i.e., the heating element can be moved proximally until the distal end of the heating element is adjacent to the proximal end of the previously-treated segment of the HAS).

An example of an index treatment includes treatment at a temperature between approximately 95° C. and approximately 150° C. for a dwell time of approximately twenty seconds or less. In a more preferred embodiment, the preferred index treatment is performed at approximately 120° C. for a dwell time of approximately twenty seconds. The ramp time to temperature may be approximately ten seconds or less, with a preferred time of approximately four seconds or less. In certain embodiments, the intent of a short ramp time is to advantageously reach and maintain the treatment temperature quickly in order to apply heat to the HAS in a highly-localized manner.

In certain embodiments, the HAS heating is advantageously applied for a sufficient time to allow thermal conduction along collagen-dense regions (such as a vein wall) to cause fully-circumferential HAS (e.g., vein) wall shrinkage. In certain embodiments, the heating element may be provided a constant power input, independent of thermal measurement.

Once a section is treated, the distal therapeutic portion of the catheter is moved to the adjacent section. In certain embodiments, the indexing of the catheter provides an overlap portion of approximately one centimeter or less to substantially reduce or eliminate the number of under-treated sections or gaps as mentioned earlier. This process is repeated until the treatment of the HAS is complete. In some embodiments, an automatic mode may provide a signal (visual and/or audible) to the user to alert them when to move the catheter to the next treatment section.

In other embodiments, higher temperatures such as, for example, approximately 200° C. or approximately 500° C., at a shorter dwell time are also possible depending on circumstances of the treatment. In yet other embodiments, the treatment process may comprise a multi-step heating process, such as a planned initial temperature overshoot followed by a lower temperature. For example, the HAS may be treated at a first temperature (e.g., approximately 110° C.) for a first portion of the process and a second temperature (e.g., approximately 95° C.) for a second portion of the process. Alternatively, a succession of heating and dwell periods may be employed (e.g., ten one-second heating periods spaced by nine one-second off periods, or five three-second heating periods at approximately 140° C. spaced by four one-second off periods) to limit the spread of conductive heating such as in the case where the dwell time may allow thermal relaxation. The total energy input to the HAS, as dependant upon the power level over time, may preferably be within the range of 40 to 200 Joules per centimeter and, more preferably, within the range of 70 to 140 Joules per centimeter.

In certain embodiments of the catheter system, fluid may be injected through a lumen of the catheter to flow through a region heated by the heating element such that the injected fluid becomes heated to a therapeutic temperature (e.g., approximately 80-100° C.) to extend the length of heating along the HAS. The rate of fluid injection may be controlled by a fluid drip rate within a drip chamber, by a fluid pump such as a peristaltic pump, by regulated pressure input to the lumen optionally with a resistive orifice, or by other means.

Figure 34A:
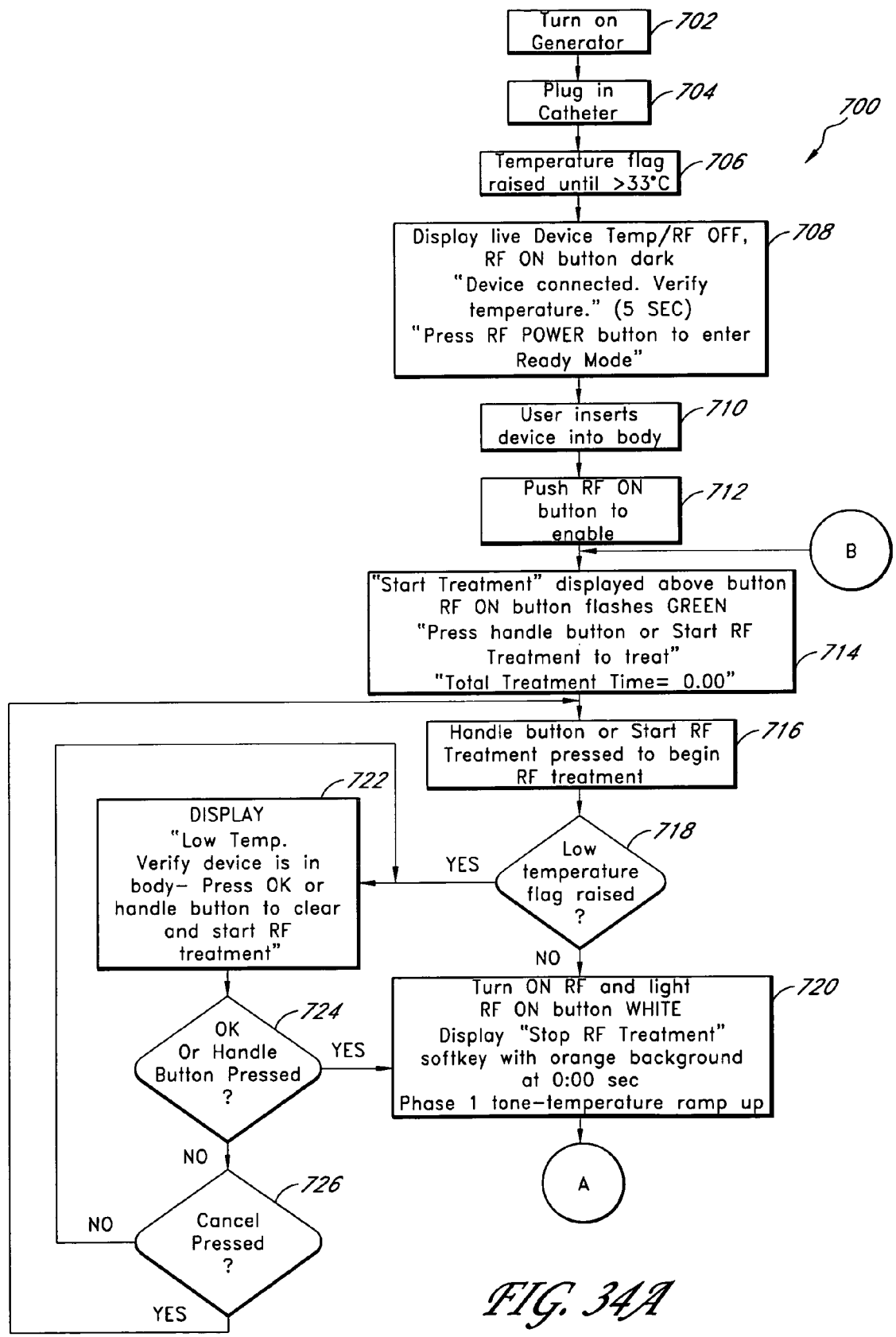
FIGS. 34A-34C illustrate an exemplary flowchart of an embodiment of a method of use of a system for treating hollow anatomical structures.
Figure 34B:
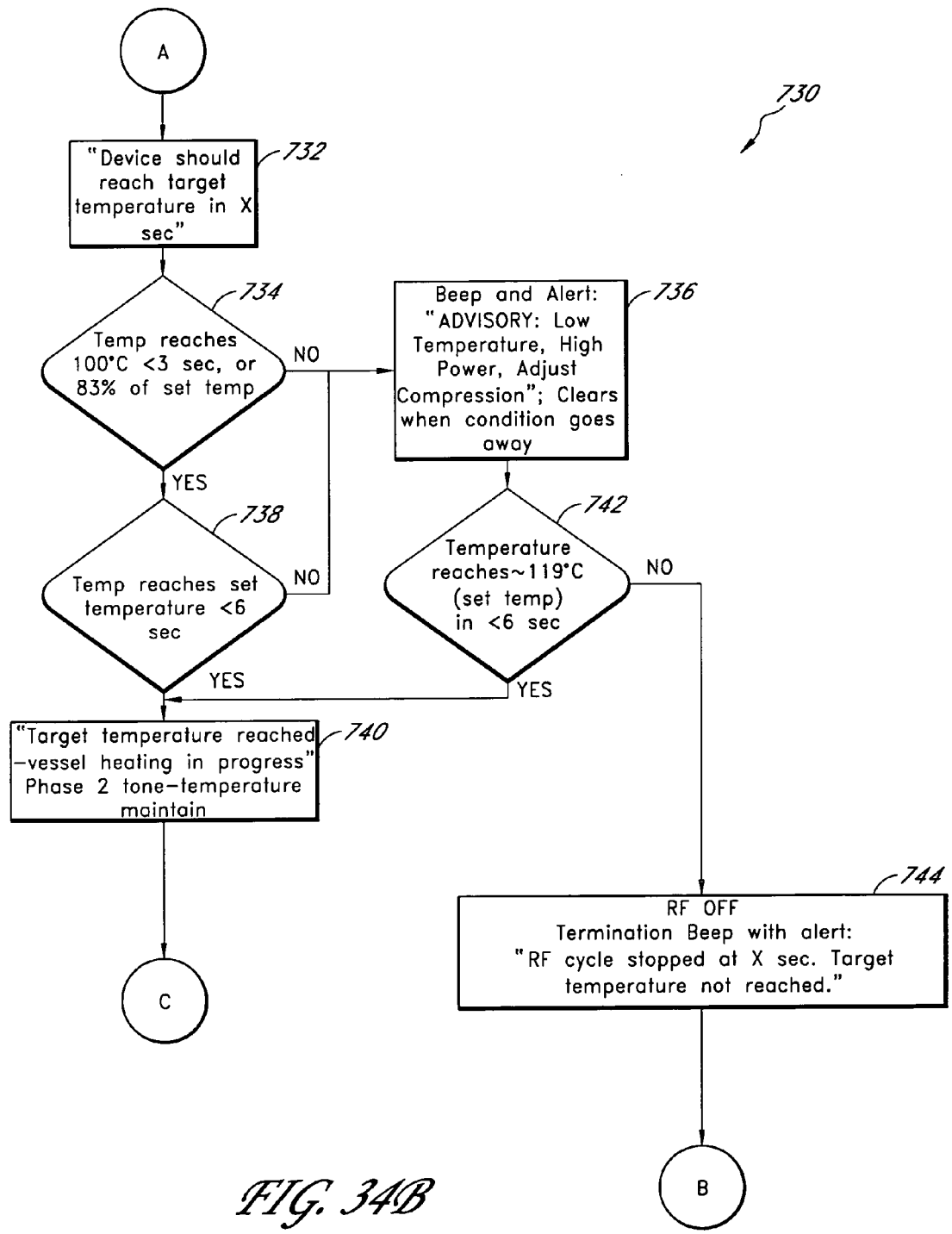
Figure 34C:
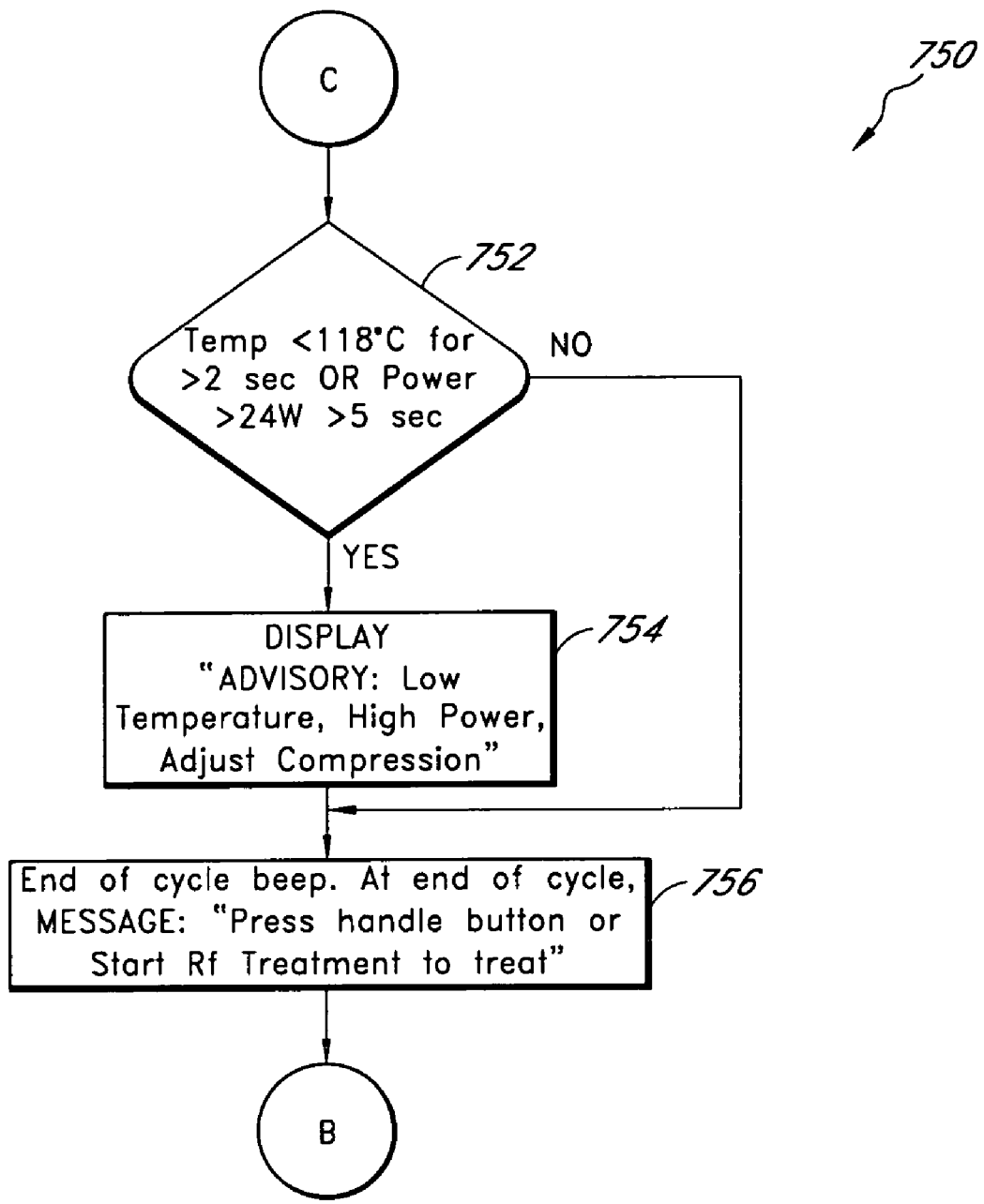

FIGS. 34A-34C illustrate one embodiment of a method of use of a system for treating a HAS. In certain embodiments, the treatment system may comprise one of the indexing treatment systems disclosed herein, such as any of the catheters 202, 202', 900, 950. For ease of description, each of FIGS. 34A-34C illustrates one of three different processes or stages of the method of use. A skilled artisan will recognize, however, that any of the described processes/stages may be combined into a single process or stage and/or may be subdivided into additional processes or stages.

In particular, FIG. 34A illustrates a catheter preparation process 700 that begins with Block 702, wherein a user turns on a generator. In certain embodiments, the generator may comprise an RF generator, such as, for example, the RFGPlus RF generator. Once the generator is turned on, an interface of the generator, such as a display, may prompt the user to connect an appropriate treatment device, such as one of the catheter devices disclosed herein, to the generator.

At Block 704, the user couples the catheter device to the generator. In certain embodiments, to determine if the catheter is properly coupled to the generator and/or if the appropriate catheter is being used, the generator may sense an identification resistor or other identifying information associated with the catheter. In yet further embodiments, the generator may also determine from the identification information certain attributes and/or operational characteristics of the attached catheter device. For instance, the generator may determine the length of the catheter being used (e.g., 60 or 100 centimeters). The generator may also specify a certain logic set (e.g., program, or set of default parameters) to associate with the catheter being used.

At Block 706, a temperature flag of the generator is raised until a temperature of the attached catheter is greater than 33° C. Such a flag, in certain embodiments, helps prevent a user from powering-up the treatment system while the catheter is still positioned outside the patient's body. For instance, the temperature may be read from one or more temperatures sensors or like devices positioned near or on a heating coil of the catheter. Once the temperature of the catheter exceeds 33° C., the flag is preferably removed. If at some point during the treatment of the patient the catheter temperature drops below approximately 25° C., the generator may raise the flag again.

At Block 708, the generator interface displays that the catheter device is properly connected to the generator. For instance, the interface may display the message "DEVICE CONNECTED. VERIFY TEMPERATURE." In certain embodiments, the message is displayed for approximately five seconds. At Block 708, the generator may also display the message "PRESS RF POWER BUTTON TO ENTER READY MODE." In certain embodiments, an "RF ON" control (e.g., button) of the generator remains dark (e.g., not lit or highlighted) until the catheter is ready to receive power from the generator.

At Block 710, the user inserts the catheter into the body of the patient. At Block 712, the user activates the "RF ON" button on the generator to enable power delivery to the catheter. At Block 714, in certain embodiments, a start treatment message is displayed above the "RF ON" button, the "RF ON" button flashes green, and/or a message is displayed reading "PRESS HANDLE BUTTON OR START RF TREATMENT TO TREAT." The generator interface may also indicate a total treatment time (such as the cumulative time of treatment of a group of segments).

At Block 716, the user activates a control (e.g., a button) on the handle of the treatment device or a start RF treatment button on the generator to begin the RF treatment. At Block 718, the catheter preparation process 700 determines if the low temperature flag is raised or if it has been lowered. Such a determination may advantageously indicate to the user if the catheter device has been inserted into the patient's body. This may help to prevent unintentional delivery of power with the catheter device outside of the patient. If the low temperature flag is not raised, the catheter preparation process 700 proceeds with Block 720.

At Block 720, the generator initiates delivery of power to a therapeutic portion (e.g. a heating coil) of the catheter device. In certain embodiments, the generator also provides one or more indications to the user that delivery of power has initiated. For instance, the "RF ON" button may turn white, the generator interface may display a "STOP RF TREATMENT" option, the generator may provide an audible tone, combinations of the same or the like. In certain embodiments, the generator then begins to ramp up the temperature of the catheter device to initiate treatment.

If at Block 718 the low temperature flag is raised, the catheter preparation process 700 continues to Block 722. At Block 722, the generator interface displays "LOW TEMPERATURE. VERIFY DEVICE IS IN THE BODY—PRESS OK OR HANDLE BUTTON TO CLEAR AND START RF TREATMENT." At Block 724, the catheter preparation process 700 determines if the "OK" button or the handle button has been pressed. If either button has been pressed, the catheter preparation process 700 proceeds with Block 720. If neither button was pressed, the catheter preparation process 700 continues with Block 726. At Block 726, the process 700 determines if the cancel button was pressed. If the cancel button was not pressed, the catheter preparation process 700 returns to Block 722. If the cancel button was pressed, the process 700 returns to Block 716.

Once RF power is initiated, the catheter preparation process 700 moves to a Phase 1 process 730, an embodiment of which is illustrated in more detail by the flowchart of FIG. 34B. In certain embodiments, the generator provides approximately forty watts of power to the catheter device for approximately six seconds during the Phase 1 process 730.

As illustrated, the Phase 1 process 730 begins with Block 732, wherein the generator interface displays the message "DEVICE SHOULD REACH TARGET TEMPERATURE IN 'X' SECONDS," wherein "X" represents a time limit such as, for example, five seconds. In yet other embodiments, other appropriate time limits may be used, such as, for example, ten seconds.

At Block 734, the Phase 1 process 730 determines if the temperature of the device has reached, for example, a set temperature of 120° C., 100° C. or 83% of the set temperature in less than three seconds. For instance, in certain preferred embodiments, the set temperature is generally attained within approximately 1.7 seconds after the initiation of power. If the indicated temperature has not been reached in the allotted time, the Phase 1 process 730 moves to Block 736, wherein the generator may issue an audible and/or visual alert. For instance, the generator display may show a message "ADVISORY: LOW TEMPERATURE, HIGH POWER. ADJUST COMPRESSION." In certain embodiments, the displayed message remains until the error condition is corrected.

At Block 734, if the temperature reaches the appropriate level within the allotted time, the Phase 1 process 730 continues with Block 738. At Block 738, the Phase 1 process 730 determines if the temperature of the device has reached the set temperature in less than, for example, six seconds. If the temperature has not reached the set temperature in less than six seconds, the Phase 1 process 730 returns to Block 736.

If the temperature has reached the set temperature in less than six seconds, the Phase 1 process 730 proceeds with Block 740. At Block 740, the generator interface displays the message "TARGET TEMPERATURE REACHED—VESSEL HEATING IN PROGRESS." In certain embodiments, at this point, the generator issues a Phase 2 tone and maintains the current (e.g., set) temperature.

Returning to Block 736, once the error condition is cleared, the Phase 1 process 730 moves to Block 742, wherein the generator determines if the temperature of the catheter device has reached approximately 119° C. (approximately the set temperature) in less than six seconds. If so, the Phase 1 process 730 proceeds with Block 740.

If the catheter temperature has not reached the set temperature in the allotted amount of time, the Phase 1 process 730 proceeds with Block 744. At Block 744, the RF power delivery is terminated. In certain embodiments, the generator may issue a termination beep and/or display the message "RF CYCLE STOPPED AT "X" SECONDS. TARGET TEMPERATURE NOT REACHED." In certain embodiments, this message may remain until any generator key is pressed, the handle button is pressed, the RF treatment is resumed at a new location, and/or after a ten-second time out. The Phase 1 process 730 then returns to Block 714 of the catheter preparation process 700.

After Block 740, the Phase 1 process 730 continues with a Phase 2 process 750, an embodiment of which is illustrated in more detail by the flowchart of FIG. 34C. In certain embodiments, the generator reduces the power output to the catheter device during the Phase 2 process 750, which preferably lasts for approximately fourteen seconds.

The Phase 2 process 750 begins at Block 752, wherein the process 750 monitors (i) if the temperature of the catheter device drops below 118° C. (approximately the set temperature) for more than two seconds or (ii) if the power exceeds twenty-four watts for more than five seconds. Such conditions may occur, for example, if there is too much fluid present in the treatment region of the HAS (e.g., insufficient compression applied to the patient's limb). In certain embodiments, such monitoring is performed until the final five seconds of the Phase 2 process 750. Thus, such embodiments of the process 750 ignore temperature decreases and/or power increases during the final five seconds of the treatment.

If either condition described in Block 752 does occur, the Phase 2 process 750 proceeds with Block 754, wherein the generator interface displays the message "ADVISORY: LOW TEMPERATURE, HIGH POWER. ADJUST COMPRESSION." In certain embodiments, when such a condition is corrected, the generator clears the warning message. Following Block 754, or if neither of the specified conditions occurs at Block 752, the Phase 2 process 750 continues with Block 756. At Block 756, the generator provides an "end of cycle" alert (e.g., a beep). In addition, in certain embodiments, a message on the generator interface may read "PRESS HANDLE BUTTON OR START RF TREATMENT TO TREAT." The Phase 2 process 750 then returns to Block 714 of the catheter preparation process 700 to begin another treatment (e.g., a treatment of another section of the HAS).

FIGS. 34A-34C thus illustrate one embodiment of a method of treating a hollow anatomical structure, comprising: inserting a heat delivery device into a hollow anatomical structure; delivering power to the heat delivery device during a temperature ramp-up phase; measuring time elapsing during power delivery; monitoring operation of the heat delivery device; and if the operation of the heat delivery device during or shortly after said temperature ramp-up phase is acceptable, delivering power to the heat delivery device after said temperature ramp-up phase.

In variations of the method, the method further comprises: delivering power to the heat delivery device to reach a first treatment temperature; and delivering power to the heat delivery device to reach a subsequent second treatment temperature which is lower than said first treatment temperature.

In further variations of the method, the heat delivery device is an electrically driven heating element, an electrode, or a laser. When the heat delivery device comprises an electrically driven heating element, an energy coupling surface of the heating element may have a distal-to-proximal length which is at least fifteen times the width of the heating element.

Further variations of the method additionally comprise measuring a temperature of at least one of (i) at least a portion of the heat delivery device, and (ii) a portion of the hollow anatomical structure being treated. An example of this is shown in FIG. 34B in Blocks 734, 738, and 742, which employ the temperature data measured. In another variation of the method, monitoring operation of the heat delivery device comprises determining whether the measured temperature reaches or exceeds a target temperature within a time limit. An example of this is shown in FIG. 34B in Block 738, in which the process checks whether the temperature has reached a set temperature (in one variation, 120° C.). In another variation, monitoring operation of the heat delivery device comprises determining whether the measured temperature falls below a target temperature within a time limit.

In a further variation, the method additionally comprises proceeding to deliver power to the heat delivery device after the temperature ramp-up phase only when the target temperature is reached or exceeded within the time limit. An example of this is shown in Block 744 in FIG. 34B, in which the power to the heat delivery device is turned off when the set temperature is not reached within a period of six seconds.

In another variation of the method, monitoring operation of the heat delivery device comprises comparing a measurement of electrical impedance with a reference waveform.

A further variation of the method additionally comprises displaying an instruction to adjust treatment of the hollow anatomical structure if the operation of said heat delivery device during said temperature ramp-up phase is not acceptable. In a further variation of this method, displaying an instruction to adjust treatment of said hollow anatomical structure comprises displaying an instruction to adjust the compression of the hollow anatomical structure. An example of this is shown in FIG. 34B in Block 736, in which a display indicates that compression should be adjusted when the temperature has not reached 100° C. within three seconds, or 83% of the set temperature.

In a variation of the method, the hollow anatomical structure is a vein.

Although the foregoing method of use has been described with reference to particular embodiments, in other embodiments not all of the disclosed blocks need be performed, or additional blocks may be included. For example, different types of messages may be displayed on the generator interface and/or on a computer display coupled to the generator. In yet other embodiments, certain blocks may be combined into a single block, or one or more blocks may be subdivided into multiple blocks. In yet other embodiments, the blocks may be performed in a different order than the order described herein.

For example, in certain embodiments, the method of use described herein further utilizes a process of detecting poor or non-uniform HAS fluid evacuation (e.g., exsanguination) and tissue contact with the heating element, such as can be achieved through external compression. The detection process may include detecting fluid evacuation and tissue contact with the associated heating element by: measuring the ramp rate during heating; comparing temperatures from multiple heat sensors along the heating element; and/or determining the heating element temperature through RTD detection of temperature by impedance and then comparing that temperature to the temperature measured by at least one heat sensor. Through such a detection process, the treatment system may detect unfavorable conditions, such as, for example, the absence or release of external compression and/or a portion of the heating element being positioned within an introducer sheath. In yet other embodiments, the thermal environment of the heating element may be detected through providing an initial power pulse to the heating element and then measuring the rate of temperature decay. Such a characterization of the thermal environment may also advantageously be used to detect if the heating element is positioned outside the patient, such as during an accidental start before the catheter has been properly inserted into the HAS.

In certain embodiments, a boiling sensor may also be integrated into the catheter device, such as by providing at least two electrodes on the exterior of the catheter and then measuring the resistance to current flow between the two electrodes (e.g., to indicate an air gap). In such embodiments, the power delivered by the generator may be adjusted relative to the indication of boiling, such as by reducing the delivered power when boiling occurs.

It will also be understood that, in certain embodiments, one or more blocks of the flowcharts illustrated in FIGS. 34A-34C may be implemented by computer program instructions. For instance, the computer program instructions may be provided to a processor of the RF generator or other treatment device power source, a general purpose computer, special purpose computer, or other programmable data processing apparatus, such that the instructions, which execute via the processor of the RF generator, power source, computer or other programmable data processing apparatus, create means for implementing the acts specified in the flowchart blocks. In certain embodiments, the blocks may be executed by one or more modules that comprise logic embodied in hardware or firmware of the RF generator, computer, etc., or in software stored in the RF generator, power source, computer, etc. It will be further appreciated that hardware modules may comprise connected logic units, such as gates and flip-flops, and/or may comprise programmable units, such as programmable gate arrays or processors.

The computer program instructions may also be stored in a computer-readable medium that can direct the RF generator, power source, a computer or other programmable data processing apparatus to operate in a particular manner, such that the instructions stored in the computer-readable medium produce an article of manufacture including instruction means which implement the acts specified in the flowchart blocks.

FIGS. 34A-B thus illustrate one embodiment of a method of facilitating the treatment of a hollow anatomical structure. The method involves (A) initiating power delivery to an energy application device of a hollow anatomical structure treatment device; (B) measuring an operating parameter of the treatment device, the operating parameter being relevant to energy coupling between the energy application device and its surroundings; (C) determining whether the operating parameter satisfies a first energy coupling condition within a first time interval following the initiating; and (D) if the operating parameter does not satisfy the first energy coupling condition within the first time interval, providing a warning.

In variations of this method of facilitating treatment, the measured operating parameter can be any one or combination of the following: the temperature of at least a portion of the treatment device; the temperature of at least a portion of the energy application device; and/or the power delivered to the energy application device. Where power is delivered to the energy application device by electric current, the measured operating parameter can be any one or combination of the following: the electrical power delivered to the energy application device; the magnitude of the electric current delivered to the energy application device; and/or the electrical impedance of the energy application device. Where power is delivered to the energy application device by electric current, the energy application device can comprise a conducting coil.

In further variations of this method of facilitating treatment, where the measured operating parameter is the temperature of at least a portion of the energy application device, the first energy coupling condition can comprise meeting or exceeding a first target temperature value for the temperature of at least a portion of the energy application device; or meeting or exceeding the first target temperature value within a prescribed period of time after initiating power delivery. In FIG. 34B, examples of this are shown in Block 734, where the process checks for a target temperature (100 degrees C) within a prescribed time period (3 seconds) after initiation of power delivery; in Block 738, where the process checks for a different target temperature (the "set" temperature which can be a desired treatment temperature; in this case, 120 degrees C) within a prescribed time period (6 seconds) after initiation of power delivery; and in Block 742, where the process checks for a different target temperature (approximately the set temperature) within a prescribed time period (6 seconds) after initiation of power delivery.

In further variations of this method of facilitating treatment, where the measured operating parameter is the temperature of at least a portion of the energy application device, the first energy coupling condition can comprise the absence of sudden, relatively large changes to the temperature of at least a portion of the energy application device. This particular variation provides a method of or involving detecting sudden insufficient compression of the portion of the HAS in which the energy application device is positioned (or detecting the removal of compression of the HAS), which increases fluid flow around the energy application device and thereby drains heat from the energy application device.

In further variations of this method of facilitating treatment, where the measured operating parameter is the power delivered to the energy application device, the first energy coupling condition can comprise a delivered power magnitude which is substantially similar to a reference waveform of expected power magnitude; and/or a rate of change of the magnitude of power delivered to the energy application device which is substantially similar to a reference waveform of expected power delivered after achievement of a target temperature value. To implement checking for these energy coupling conditions, a reference waveform (indicating magnitude vs. time) of expected power magnitude can be stored in memory accessible to the power source (e.g. RF generator) processor. The delivered power magnitude, and/or a rate of change thereof, can be monitored, either continuously, intermittently, or at selected "checkpoints," and compared to the reference waveform. Substantial similarity (e.g. deviating no more than 1%, 5%, or 10% at any point, in various embodiments) to the reference waveform indicates normal power-up or operation of the energy application device. In the variation where the energy coupling condition is a delivered power magnitude substantially similar to the reference waveform, this particular variation provides a method of or involving detecting power-up of the energy application device in air, the absence or insufficiency of local HAS compression at the initiation of power delivery, and/or the absence or insufficiency of local HAS compression later during power delivery, as these conditions are associated with improper delivered power magnitude. In the variation where the energy coupling condition is a rate of change of delivered power magnitude substantially similar to the reference waveform, this particular variation provides a method of or involving detecting removal or insufficiency of local HAS compression, and/or movement of the energy application device during heating, as these conditions are associated with improper delivered power magnitude.

In further variations of this method of facilitating treatment, where the measured operating parameter is the electric current delivered to the energy application device, the first energy coupling condition can comprise a delivered electric current magnitude which is substantially similar to a reference waveform of expected electric current magnitude; and/or a rate of change of the magnitude of electric current delivered to the energy application device which is substantially similar to a reference waveform of expected electric current delivered after achievement of a target temperature value. To implement checking for these energy coupling conditions, a reference waveform (indicating magnitude vs. time) of expected electric current magnitude can be stored in memory accessible to the power source (e.g. RF generator) processor. The delivered electric current magnitude, and/or a rate of change thereof, can be monitored, either continuously, intermittently, or at selected "checkpoints," and compared to the reference waveform. Substantial similarity (e.g. deviating no more than 1%, 5%, or 10% at any point, in various embodiments) to the reference waveform indicates normal power-up or operation of the energy application device.

In further variations of this method of facilitating treatment, where the measured operating parameter is the electrical impedance of the energy application device, the first energy coupling condition comprises a measured electrical impedance magnitude which is substantially similar to a reference waveform of expected electrical impedance of the energy application device; and/or a measured rate of change of the magnitude of the electrical impedance of the energy application device which is substantially similar to a reference waveform of expected electrical impedance of the energy application device. To implement checking for these energy coupling conditions, a reference waveform (indicating magnitude vs. time) of expected electrical impedance magnitude can be stored in memory accessible to the power source (e.g. RF generator) processor. The electrical impedance magnitude, and/or a rate of change thereof, can be monitored, either continuously, intermittently, or at selected "checkpoints," and compared to the reference waveform. Substantial similarity (e.g. deviating no more than 1%, 5%, or 10% at any point, in various embodiments) to the reference waveform indicates normal power-up or operation of the energy application device.

In further variations of this method of facilitating treatment, if the operating parameter does not satisfy the first energy coupling condition within the first time interval, power delivery to the energy application device is reduced or terminated. In FIG. 34B, examples of this are shown in Block 734, where failure to satisfy the first energy coupling condition (temperature above 100 degrees C) during a time interval (within 3 seconds after initiation of power delivery) can lead to power shutdown in Block 744; and in Blocks 738 and 742, which also set forth energy coupling conditions (target temperatures) and time intervals (within 6 seconds after initiation of power delivery), wherein failure to satisfy the coupling condition in the specified time can also lead to power shutdown in Block 744.

In further variations of this method of facilitating treatment, the warning provided (if the measured operating parameter does not satisfy the first energy coupling condition within the first time interval) comprises a message to adjust the environment of the hollow anatomical structure treatment device within the patient. Examples of this are shown in Blocks 736 and 754. Accordingly, one variation of the message can instruct a user to adjust or improve compression of the portion of the hollow anatomical structure containing the treatment device.

Further variations of this method of facilitating treatment can also involve: determining whether the operating parameter satisfies a second energy coupling condition within a second time interval following the first time interval; and, if the operating parameter does not satisfy the second energy coupling condition within the second time interval, providing a warning. Examples of this are shown in Blocks 738, 742 and 752. Still further variations of this method can also involve terminating or reducing power delivery to the energy application device if the operating parameter does not satisfy the second energy coupling condition within the second time interval. An example of this is shown in Block 744.

Further variations of this method of facilitating treatment can also involve taking corrective measures such as any one or more of the following: applying compression in the vicinity of the hollow anatomical structure containing the energy application device; adjusting the location or force of existing compression in the vicinity of the hollow anatomical structure containing the energy application device; and/or verifying effective occlusion of flow within the hollow anatomical structure in the vicinity of the energy application device.

In further variations of this method of facilitating treatment, the energy application device comprises a resistance temperature device; the method further comprises computing a temperature of the energy application device based on the electrical impedance of the energy application device; and the first energy coupling condition comprises correlation of the measured temperature of the energy application device to the computed temperature of the energy application device. This particular variation provides a method of or involving detecting the presence of non-uniform temperature of the energy application device, and/or detecting non-uniform or inadequate local HAS compression, as these conditions are associated with lack of correlation between measured temperature and computed temperature of the energy application device.

In view of FIGS. 34A-B and the disclosure of treatment devices such as the catheters 202, 202', 900 and 950, one embodiment of apparatus for use in treating a hollow anatomical structure comprises: (A) an energy application device adapted to receive power from a power source; (B) a measuring device that measures an operating parameter of the energy application device, the operating parameter being relevant to energy coupling between the energy application device and its surroundings; (C) a module in communication with the measuring device, the module configured to determine whether the operating parameter satisfies a first energy coupling condition within a first time interval following the initiation of power delivery to the energy application device; and (D) a warning device in communication with the module, the module further configured to cause the warning device to provide a warning if the operating parameter does not satisfy the first energy coupling condition within the first time interval.

In various embodiments, the energy application device can comprise any of the heating elements, electrodes, therapeutic devices, etc. disclosed herein, including but not limited to the resistive element 14, the heating element 208, or therapeutic element 280; or a laser, fluid-conducting heat exchanger, chemical reaction chamber or any other device suitable to impart energy to an HAS. The measuring device can comprise a thermocouple, a thermistor, an RTD (which can be the energy application device itself where the energy application device is an electrically driven coil or other electrically driven heating element), a photodetector, an ammeter, ohm meter, volt meter; or hardware or software components of the treatment power source, RF generator, computer, etc. The module can comprise hardware such as a treatment power source, RF generator, computer, etc., or software executing on any of these devices, or firmware, or a combination of hardware, software and/or firmware.

FIG. 34A thus illustrates one embodiment of a method comprising: (A) sensing a temperature on or near at least a portion of a heat application device of a hollow anatomical structure treatment device; (B) determining whether the temperature satisfies a required initial temperature condition; (C) receiving a request to initiate power delivery to the heat application device of the hollow anatomical structure treatment device; and (D) if the temperature does not satisfy the required initial temperature condition, performing a safety procedure to interrupt a normal power-up process for the heat application device.

As one example of determining whether the sensed temperature satisfies a required initial temperature condition, in Block 718 the process checks for the presence of a low temperature flag, which remains raised until the required initial temperature condition (in this case, having sensed a temperature above 33 degrees C since the catheter was plugged in, and/or currently sensing a temperature above 33 degrees C) has been satisfied. As examples of receiving a request to initiate power delivery, Block 716 mentions two alternatives: sensing the press of a power activation button on the catheter handle, or sensing the press of a Start RF Treatment button or "softkey" on the power source. As an example of performing a safety procedure, Blocks 722-726 show the disabling of therapeutic power delivery start-up, the display of a low temperature warning and prompt for the user to insert (or verify insertion of) the energy application device, and the actions to be taken if the user presses the power activation button on the catheter or power source, or a cancel button.

One variation of this method involves allowing a normal power-up process for the heat application device to proceed, if the sensed temperature satisfies the required initial temperature condition. One example of this is shown in Blocks 718-720, wherein device power-up proceeds if the low temperature flag is not raised.

In another variation of this method, determining whether the temperature satisfies a required initial temperature condition comprises determining whether the temperature has satisfied the required initial temperature condition at any time during a temperature sensing period. The temperature sensing period can begin after connection of the treatment device to a power source (Block 704), and/or end before delivery of therapeutic energy from the power source to the treatment device (Block 720).

In further variations of this method, the safety procedure can comprise preventing the initiation of power delivery to the heat application device (e.g., Blocks 722-724), and/or ceasing the delivery of power to the heat application device.

In further variations of this method, the required initial temperature condition can be that the sensed temperature meet or exceed a minimum temperature. The minimum temperature can be any one or more of: significantly above an expected ambient room temperature; substantially at an expected internal temperature of the hollow anatomical structure to be treated with the treatment device; and/or 5 to 10 degrees Celsius lower than the normal physiologic internal temperature of a hollow anatomical structure of the type normally treated with the treatment device.

In further variations of this method, the required initial temperature condition can be that the sensed temperature fall within an acceptable temperature range. The acceptable temperature range can be any one or more of: significantly above an expected ambient room temperature; bracketing an expected internal temperature of the hollow anatomical structure to be treated with the treatment device; and/or bracketing a temperature which is 5 to 10 degrees Celsius lower than the normal physiologic internal temperature of a hollow anatomical structure of the type normally treated with the treatment device.

Further variations of this method comprise providing a warning if the sensed temperature does not satisfy the required initial temperature condition. One example of this is seen in Block 722.

Further variations of this method comprise verifying that the heat application device is properly disposed within a hollow anatomical structure of a patient; and manually overriding the safety procedure and initiating a power-up process for the heat application device. One example of this is seen in Block 724.

In view of FIGS. 34A-B and the disclosure of treatment devices such as the catheters 202, 202', 900 and 950, one embodiment of apparatus for use in treating a hollow anatomical structure comprises: (A) a heat application device adapted to receive power from a power source; (B) a user interface adapted to receive a request from a user to initiate power delivery to the heat application device; (C) a temperature measuring device for measuring a temperature within or near the heat application device; (D) a module in communication with the temperature measuring device and the user interface, the module configured to determine whether a temperature measured by the temperature measuring device satisfies a required initial temperature condition; wherein the module is further configured to follow a safety procedure to interrupt a normal power-up process for the heat application device if the temperature measured by the temperature measuring device does not satisfy the required initial temperature condition.

In various embodiments, the heat application device can comprise any of the heating elements, electrodes, therapeutic devices, etc. disclosed herein, including but not limited to the resistive element 14, the heating element 208, or therapeutic element 280; or a laser, fluid-conducting heat exchanger, chemical reaction chamber or any other device suitable to impart heat energy to an HAS. The temperature measuring device can comprise a thermocouple, a thermistor, an RTD (which can be the energy application device itself where the energy application device is an electrically driven coil or other electrically driven heating element), or a photodetector; or hardware or software components of the treatment power source, RF generator, computer, etc. The module can comprise hardware such as a treatment power source, RF generator, computer, etc., or software executing on any of these devices, or firmware, or a combination of hardware, software and/or firmware.

Figure 35:
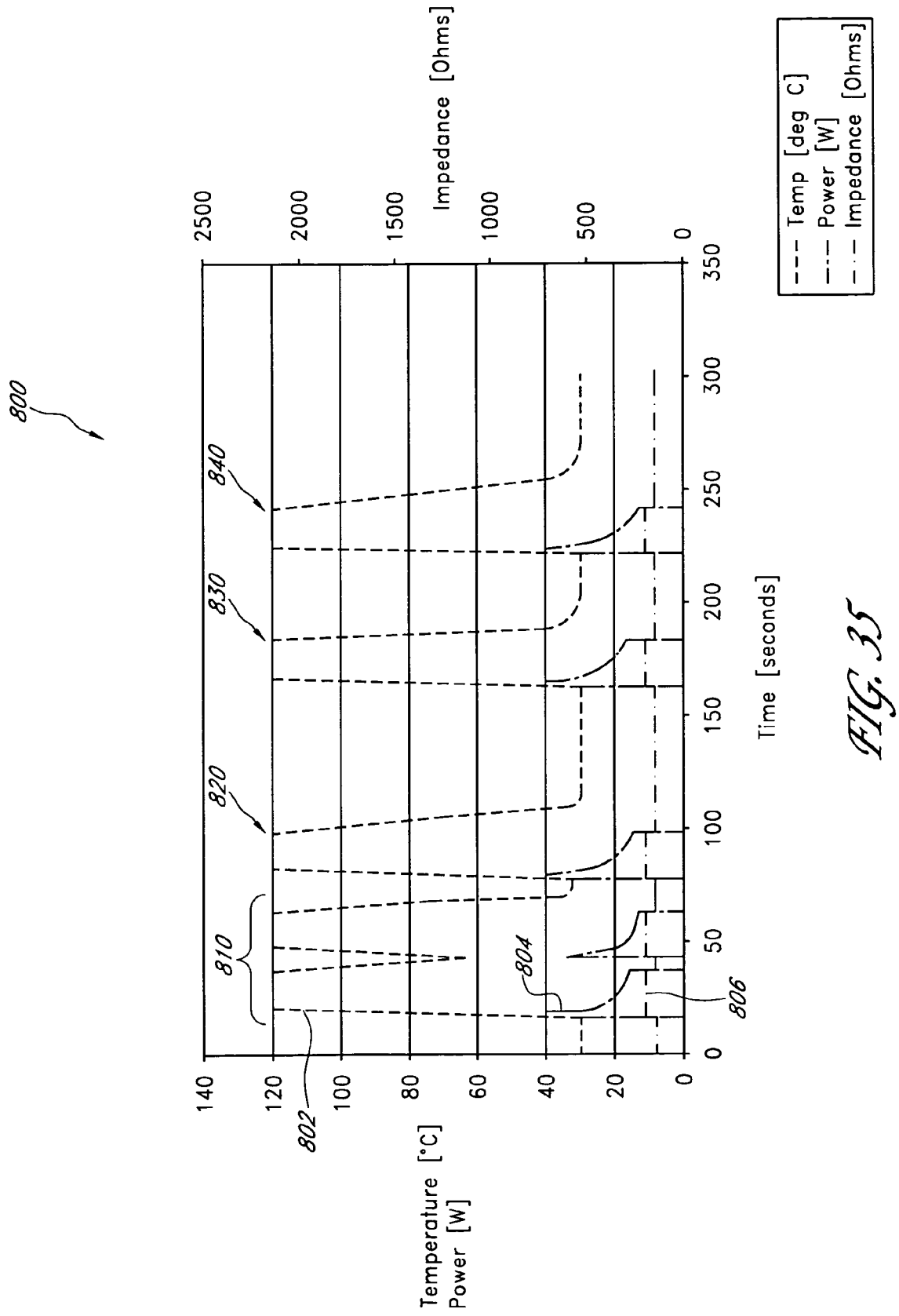
FIG. 35 illustrates an exemplary graph depicting temperature, power and resistance values during a treatment process.

FIG. 35 illustrates a graph 800 of exemplary embodiments of power, time, and temperature measurements that may be encountered during the treatment of a HAS of a patient. As illustrated, the x-axis of the graph 800 plots a time (in seconds) of the treatment process. The left y-axis of the graph 800 displays the temperature values of the catheter (in ° C.) and power values of the generator (in Watts). The right y-axis of the graph 800 illustrates the impedance values of the heating element of the catheter device (in Ohms) throughout the treatment.

As can be seen, the graph 800 comprises a temperature curve 802, a power curve 804 and an impedance curve 806 that each depicts measurements during five treatments of a patient. In particular, the graph 800 illustrates a treatment that initiates approximately at a time 20 seconds. At this point, the power delivered by the generator is ramped up to forty Watts, which causes a corresponding increase in the temperature of the catheter device (e.g., to approximately 120° C.). In certain embodiments, the catheter device reaches a target temperature of approximately 120° C. about 1.7 seconds after the power delivery is initiated.

After approximately six seconds, the power delivered by the generator is reduced to twenty-five Watts, while the temperature of the device remains at approximately 120° for approximately fourteen more seconds. Thus, the graph 800 illustrates, for example, that to maintain a target temperature of 120°, the generator need not maintain a constant power output of 40 watts once the catheter device has reached the set (target) temperature. As can also be seen from the graph 800, the impedance of the catheter device has a direct relationship to the device temperature. That is, as the temperature of the catheter device (e.g., heating coil) increases, so does the impedance of the catheter device. In certain embodiments, the graph 800 is indicative of a use of a catheter device having a heating coil made of Alloy 52.

The graph 800 also illustrates a double treatment of the first portion of a HAS, which is shown by reference numeral 810. In particular, the double treatment includes a re-application of power at a time of approximately 45 seconds such that the temperature of the catheter device does not cool to body temperature between successive treatments. Rather, the temperature of the catheter device drops to approximately 65° C., at which point power delivery is re-initiated. The temperature of the catheter device increases again to approximately 120° C. The graph 800 also illustrates a third treatment 820, a fourth treatment 830, and a fifth treatment 840. In certain embodiments, the third through fifth treatments 820, 830 and 840 correspond to treatments in different segments of the target HAS.

Accordingly, the graph 800 can be considered to depict a method of treating an HAS in which multiple treatments are administered to the HAS. The first treatment 810 is performed at the distal-most treatment location within the HAS, and the second through fourth treatments 820, 830, 840 are performed at successively more proximal locations, as the catheter is moved proximally between each treatment. As depicted, the first treatment 810 can involve applying energy to the first treatment location in the HAS at two (or more) distinct times, and the subsequent treatments 820, 830, 840, etc. can involve applying energy to the subsequent treatment locations within the HAS only once. Alternatively, multiple distinct energy applications can be employed in any one or more of the subsequent treatments. Whether one or multiple energy applications are employed in the first treatment 810 (or in the subsequent treatments 820, 830, 840), in certain embodiments, the treatment method depicted by the graph 800 can comprise applying energy to the first treatment location in the HAS (in the first treatment 810) for a longer total duration than to any one of the subsequent treatment locations (in the subsequent treatments 820, 830, 840). This can be done in treatment situations where the HAS has a larger cross-sectional profile, as viewed along a longitudinal axis of the HAS, in the first treatment location than in any one of the subsequent treatment locations. Such a situation is often encountered when treating the GSV as depicted in FIGS. 16A-16D, when the catheter is drawn proximally from the SFJ as the treatment progresses. In this type of GSV treatment, the first treatment location (the site of the first treatment 810) is closer to the SFJ than is any of the subsequent treatment locations.

Figure 36A:
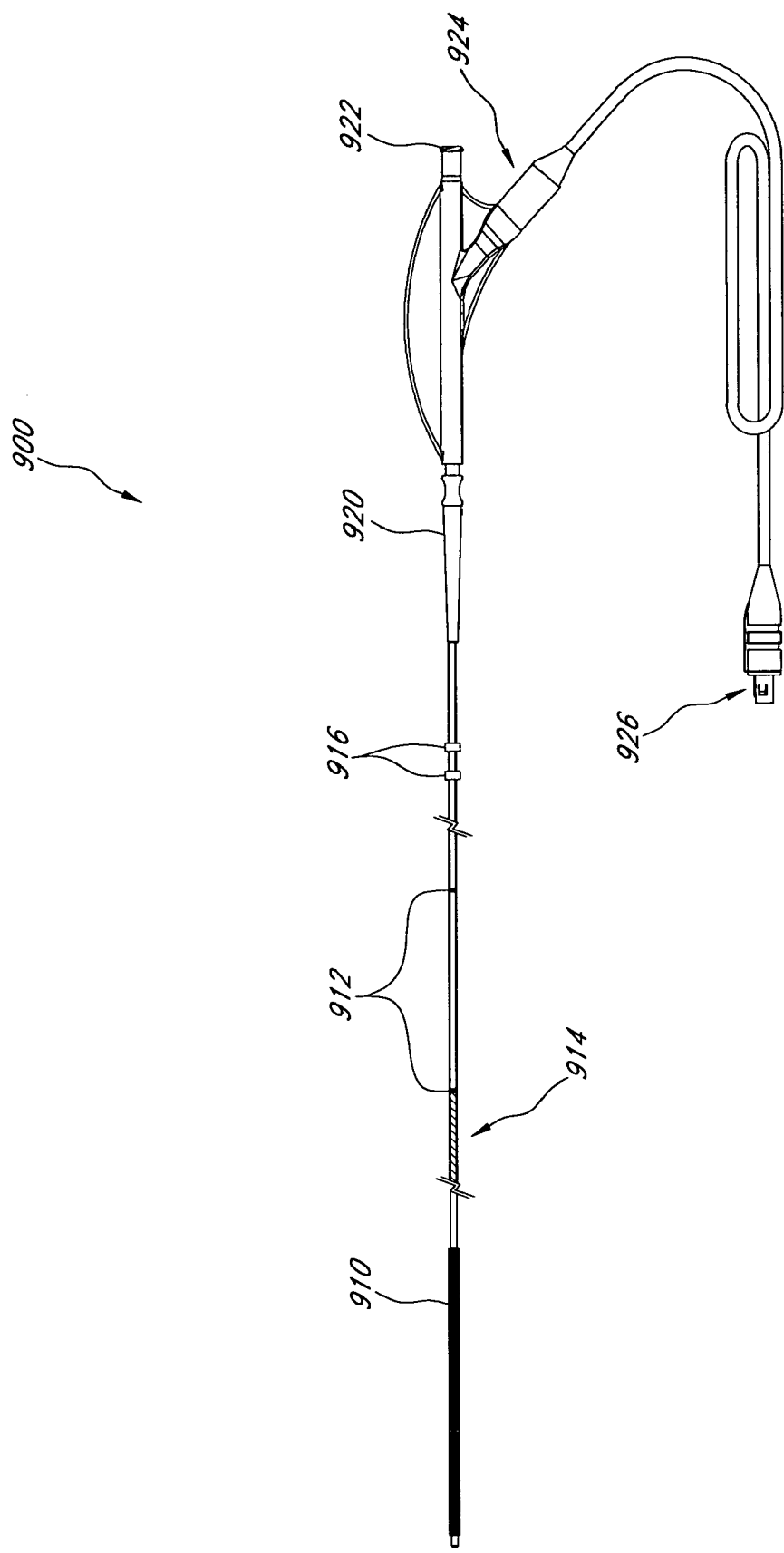
FIG. 36A illustrates another embodiment of an indexing treatment system for hollow anatomical structures.

FIG. 36A illustrates an embodiment of a catheter system 900 usable to treat a HAS of a patient, such as, for example, according to the treatment methods described herein. The catheter system 900 includes a heating element 910, which may comprise any of the heating elements or therapeutic elements described herein. Thus, in various embodiments, the heating element 910 can comprise any of the devices disclosed herein as suitable for use as the resistive element 14, heating element 208 or the therapeutic element 280. The catheter system 900 also includes indexing marks 912 to assist in the positioning of the heating element 910 during successive treatments of the patient. Warning lines 914 are also included on the catheter shaft to indicate to a user the last treatment of the catheter (e.g., to prevent power delivery while the heating element is in an introducer sheath). The catheter system 900 also includes adjustable markers 916 and a strain relief 920.

As is further depicted in FIG. 36A, a luer adaptor 922 is positioned on the proximal end of the catheter system 900. In certain embodiments, the luer adaptor is in fluid communication with an internal lumen of the catheter, allowing for delivery of fluid and/or passage of a guidewire. The system 900 further includes an integrated cable 924 with an instrument cable connector 926 that couples to a generator, such as one of the RF generators disclosed herein.

Figure 36B:
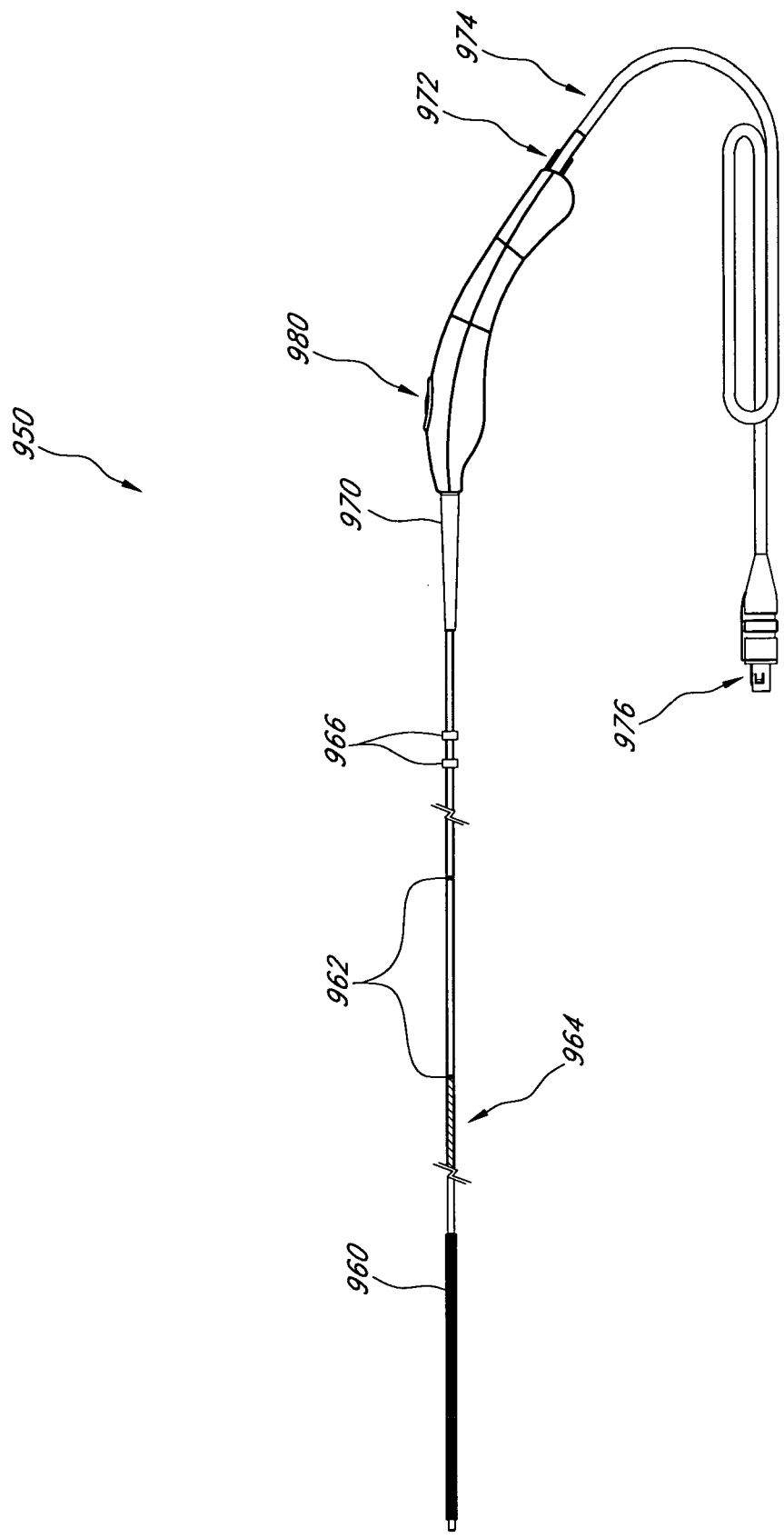
FIG. 36B illustrates another embodiment of an indexing treatment system for hollow anatomical structures.

FIG. 36B illustrates a catheter system 950 similar to the catheter system 900 of FIG. 36A. The catheter system 950 includes a heating element 960, indexing marks 962, and warning lines 964 to indicate the final treatment section of the catheter. In various embodiments, the heating element 960 can comprise any of the devices disclosed herein as suitable for use as the resistive element 14, heating elements 208 or 910, or the therapeutic element 280. The catheter system 950 also includes adjustable markers 966, a strain relief 970, a luer adaptor 972, an integrated cable 974, and an instrument cable connector 976. The catheter system 950 further includes a start/stop switch 980. In certain embodiments, the start/stop switch 980 allows a user to control the delivery of RF power to the heating element 960 without having to activate a control on an associated RF generator.

In certain embodiments, it may also be advantageous to limit the number of times that a catheter device is clinically used. For example, one or more methods may be employed by which the power generator detects how many times a catheter has been used. For instance, in certain embodiments, the catheter device may incorporate a smart electronic signature or a radio frequency identification (RFID) tag (such as, for example, in the handle). In other embodiments, the catheter device may comprise an identifying resistor with a fuse that is shorted by the initial energy delivery. In such embodiments, the generator and/or computing device associated therewith may maintain in memory data that identifies that an unused device has been used for the first time and that allows the device (a used device) to be used for a particular period of time.

Except as further described herein, any of the catheters disclosed herein may, in some embodiments, be similar to any of the catheters described in U.S. Pat. No. 6,401,719, issued Jun. 11, 2002, entitled "METHOD OF LIGATING HOLLOW ANATOMICAL STRUCTURES;" or in U.S. Pat. No. 6,179,832, issued Jan. 30, 2001, titled "EXPANDABLE CATHETER HAVING TWO SETS OF ELECTRODES;" or in U.S. patent application Ser. No. 11/222,069, filed Sep. 8, 2005, entitled "METHODS AND APPARATUS FOR TREATMENT OF HOLLOW ANATOMICAL STRUCTURES." In addition, any of the catheters disclosed herein may, in certain embodiments, be employed in practicing any of the methods disclosed in the above-mentioned U.S. Pat. Nos. 6,401,719 or 6,179,832, or the above-mentioned U.S. patent application Ser. No. 11/222,069 filed Sep. 8, 2005. The entirety of each of these patents and application is hereby incorporated by reference herein and made a part of this specification.

For exemplary purposes, a method of treatment will now be described with reference to embodiments of the treatment systems described herein. In certain preferred embodiments, the treatment method comprises endovascular vein treatment using a catheter with an integrated heating element. The description of the treatment method will be divided into three stages: a patient preparation stage; a treatment stage and a follow-up stage. A skilled artisan will recognize that the three different stages are for reference purposes only and that, in other embodiments, the acts described hereinafter may occur in different stages, in more than one stage, and/or in a different order.

The treatment method begins with the patient preparation stage. During this initial stage, a mapping of the veins intended for treatment is performed. For instance, duplex ultrasound (DU) imaging or other like methods may be used to map the vessels. In certain embodiments, the mapping includes recording the diameters of the veins for treatment. In certain embodiments, mapping further includes noting the GSV track and depth, locations of significant tributaries, aneurysmal segments and/or potential vein access sites. An indelible marker may also be used to record particular landmarks on the surface of the patient's skin. In certain embodiments, the mapping is performed on the same day as the actual vein treatment or may be performed prior to the treatment day.

Following mapping, a local anesthetic is optionally administered at the vein access site. In certain embodiments, a mild sedation may also be given to the patient. In certain embodiments, it is also advantageous to avoid during this initial stage certain factors (e.g., certain drugs, a cold environment, patient anxiety, combinations of the same or the like) that may induce venospasm, which may hinder the ability to access the target vein.

The patient is then preferably positioned to facilitate vein access, such as by positioning the patient so as to increase the diameter of the target vein. For example, the patient's legs may be positioned below the level of the patient's heart. As discussed in more detail below, prior to and/or during treatment, the patient's legs may then be moved to a horizontal position or preferably above the level of the patient's heart to assist in reducing vein diameter and/or reduce venous filling.

In certain embodiments, the physician accesses the target vein via a percutaneous stick using, for example, an 18 gauge (thin-walled) or a 19 gauge ultra thin-walled needle or via a small cut-down. The physician then inserts an introducer sheath, such as, for example, a seven-French introducer sheath with an eleven-centimeter length, into the patient.

Prior to insertion of the catheter into the sheath, the inner lumen of the catheter is preferably flushed with a heparinized saline. The lumen is then capped, and the outer surface of the catheter is wiped with saline, heparinized saline or other like solution. Once the catheter is prepared and the introducer sheath is properly positioned, the catheter is placed into the introducer sheath, and the catheter tip is advanced to a point for treating the target vein.

For example, in certain embodiments, the catheter may be advanced to the saphenofemoral junction (SFJ), the tip of the catheter being initially positioned just inferior to the ostium of the superficial epigastric vein or, alternatively, one to two centimeters distal to the SFJ. In certain embodiments, catheter navigation to the treatment site may be performed using ultrasound guidance, palpation, and/or with a guidewire. For example, a 0.025 inch guidewire with a 150 or 260 centimeter length may be used to navigate the catheter through the patient's venous anatomy. It may also be advantageous to avoid advancing the catheter against resistance from the vein so as to avoid vein perforation.

Following placement of the catheter, a local anesthetic may be optionally administered, which may preferably include perivenous tumescent anesthesia along the vein segment to be treated. In embodiments in which the target vein is located near the skin surface (e.g., less than one centimeter below the skin surface), a sufficient subcutaneous distance between the vein and skin may be created by tumescent infiltration of saline or dilute local anesthetic solution. For instance, a 20 or 22 gauge, 3.5 inch long spinal needle may be used for the tumescent fluid infiltration.

In certain embodiments, the treatment method further includes using a tumescent infiltration of dilute local anesthetic or saline into the perivascular space to create a circumferential fluid layer around the vessel to be treated. For instance, a sufficient volume of the fluid may be used to exsanguinate and/or compress the vein to achieve apposition of the catheter heating element and the vein wall. For example, the physician may confirm that the vein has been adequately compressed and that the tumescent solution has infiltrated circumferentially around the vein by scanning the entire treatment length with DU imaging.

In certain embodiments, the patient is advantageously placed in the Trendelenburg position so that the leg with the target vein is above the heart to facilitate vein collapse, apposition, and/or exsanguination. In one embodiment, the treatment method further includes partially withdrawing the introducer sheath until the sheath hub and nearest catheter index line are aligned, while also maintaining the catheter tip position. The physician then secures the introducer sheath to the skin of the patient. In another embodiment, a position datum is created in alignment with a catheter index line, such as by drawing a line or placing a piece of tape on the patient's skin.

In certain embodiments, the initial preparation stage of the treatment method includes verifying the position of the catheter tip using DU imaging or another appropriate method. For instance, the physician may verify that the heating element of the catheter is not positioned in the deep venous system. If a guidewire was used to advance the catheter within the venous system, the guidewire may then be removed.

The treatment stage follows the patient preparation stage. To begin the treatment stage, and prior to energy delivery, the physician preferably creates firm contact between the target vein wall and the heating element by compressing the HAS segment to be treated. For example, in certain embodiments, the physician may manually apply pressure to the patient's leg in order to create the desired contact. In other embodiments, the physician may wrap the patient's leg with an elastomeric wrap (e.g., an Esmark bandage) to create the desired contact along the full length of the catheter. The treatment method may also advantageously comprise creating a near-bloodless field for the catheter with little or no blood flow past the heating element.

To obtain the near-bloodless field, the physician may perform perivenous tumescent infiltration along with at least two of the following: (1) exerting external compression along the length of the heating element; (2) tightly wrapping the limb, such as, for example, with an Esmark bandage; and (3) further positioning the legs of the patient above the heart to facilitate vein collapse, apposition and/or exsanguination. In certain embodiments, the wrapping act need not be performed if a sufficient volume of tumescent infiltration is used to exsanguinate the vein and obtain apposition of the vein wall and catheter heating element.

The physician then enables RF energy delivery by activating an appropriate control (e.g., an "RF POWER" button) on the RF generator. In certain embodiments, the generator includes an indicator (such as a visual and/or audible indicator) to alert the physician that the generator is ready to deliver energy. For instance, the generator may include an RF control (e.g., an "RF POWER" button) that blinks when energy delivery is enabled. In certain further embodiments, if an error condition prevents energy delivery from being enabled, the generator may further display an error message, such as on a screen or like user interface.

Once energy delivery is enabled, the physician initiates energy delivery by activating the appropriate generator control (e.g., pressing a "Start RF" control on the generator) and/or activating a control on the catheter handle (e.g., an optional "START/STOP" button on the handle). RF energy delivery may be automatically terminated by the generator when the treatment cycle is complete, or alternatively the physician may terminate energy delivery earlier by pressing the appropriate control(s) on the generator and/or catheter handle.

Furthermore, in certain embodiments, the target vein is advantageously compressed onto the full length, or substantially full length, of the heating element during application of energy so as to avoid inconsistent effectiveness and/or possible failure by the catheter.

In certain embodiments, if a certain temperature is not reached within a predetermined period of time (e.g., six seconds) after initiation of the RF energy delivery, the treatment method includes terminating the RF energy delivery, verifying the effectiveness of flow occlusion and proper tip position, and re-initiating treatment of the HAS segment. In such embodiments, the inability to reach the set temperature within the predetermined period of time may indicate that fluid flow or presence of fluid within the vein is cooling the treatment segment. Furthermore, continuous temperature readings below the set temperature may result in incomplete treatment. If such occurs, the treatment method may include stopping the treatment, reconfirming vessel apposition to the catheter heating element, reconfirming the absence of blood flow in the vessel segment to be treated, applying more firm external compression if needed, and then retreating the HAS segment.

Following the treatment time interval, the RF energy delivery terminates automatically. The RF energy delivery may then optionally be repeated in a given vein segment according to the treatment procedures by the physician. Double-treatment, or multiple treatments, of a vein segment may be desirable at the first treatment nearest the SFJ, within an aneurismal vein segment, or near a large sidebranch vessel. In certain embodiments of the treatment method, it is preferable that the catheter is not re-advanced through an acutely treated vein segment.

In certain embodiments, the RF energy delivery may result in a target treatment temperature between approximately 100° C. and approximately 120° C. (e.g., 100° C., 110° C., or 120° C.). The treatment time per vein segment may have a duration of approximately ten seconds to approximately thirty seconds (e.g., 10, 15, 20, 25, or 30 second intervals). In certain preferred embodiments, a seven-centimeter vein segment is treated at approximately 120° C. for approximately twenty seconds. Moreover, a 45-centimeter vein may be treated in approximately three to five minutes.

After treatment of a particular segment is completed, the treatment method comprises quickly withdrawing the catheter until the next visible treatment index line is aligned with the hub of the introducer sheath or other established datum. During such withdrawal of the catheter, some friction may exist between the vein wall and catheter after a heating cycle.

Once the catheter is re-positioned appropriately, the next vein segment is treated in a manner similar to the treatment of the first section. This process is repeated until all the vein segments are treated. In certain embodiments, diagonal lines on the catheter shaft are used to indicate the last full treatment segment (e.g., when the lines are visible outside the introducer sheath). In certain embodiments, it is also advantageous to confirm that the heating element is in the vein before the last treatment in order to avoid energy delivery while the heating element is inside the introducer sheath.

In certain embodiments, the treatment method further comprises evaluating the treated vein segments to analyze the treatment outcome. For example, the physician may utilize ultrasound or other means to determine the extent of the treatment of the vein by observing for reduced vein inner diameter, thickening of the vein wall, and absence of blood flow or refluxing blood flow.

When terminating the treatment stage, the physician disables RF energy delivery by deactivating the appropriate control on the RF generator (e.g., an "RF POWER" button), withdrawing the catheter, removing the external compression, and obtaining hemostasis at the access site.

After the treatment stage, the treatment process includes a follow-up stage that comprises acts directed to facilitating and/or expediting patient recovery. The follow-up stage may include instructing the patient to ambulate frequently and/or to refrain from strenuous activities or heavy lifting for several days. Post-operative compression of the target limb is also recommended for at least one week following the treatment.

In certain embodiments of the treatment process, a follow-up examination is conducted within 72 hours of the treatment. Such an examination may preferably include an assessment to ensure that there is no thrombus extension into deep veins.

Although the foregoing treatment process has been with respect to particular embodiments, in other embodiments, the acts described herein may be combined, performed in a different order, and/or may be omitted from the treatment process. Furthermore, in certain embodiments, additional acts may be included in the treatment process in order to assist in the treatment and/or recovery of the patient.

Additional embodiments comprise methods of sterilization. Certain such methods can comprise sterilizing, either terminally or sub-terminally, any of the apparatus disclosed herein that are intended for insertion into (or other contact with) the patient or that are intended for use at or near the surgical field during treatment of a patient. Any suitable method of sterilization, whether presently known or later developed, can be employed.

Accordingly, certain methods comprise sterilizing, either terminally or sub-terminally, any one or combination of the following apparatus: the resistive element systems 10, 20 (with or without a working end of the types depicted in FIGS. 4, 5-7A, 7C-7E, and 8-13B) and/or the catheters 11, 21 or sheath 22 thereof; the HAS treatment system 200 and/or the catheters 202, 202' or introducer sheath 204 thereof; the datum devices 230, 250 (with or without a corresponding sheath 234/254 attached thereto); the HAS indexing treatment device 270 and/or the catheter 272, introducer hub 274 or outer sheath 277 thereof; the catheter shaft 290 with markings 292; the catheter 304 with detents 302; the HAS treatment system 310 and/or the catheter shaft 314 thereof; the HAS treatment system 330; the indexing devices 350, 360, 370, 390; the indexing system 430; the catheter handle 460; the catheter systems 900 and 950. Any suitable method of sterilization, whether presently known or later developed, can be employed. For example, the method can comprise sterilizing any of the above-listed apparatus with an effective dose of a sterilant such as cyclodextrin (Cidex(™)), ethylene oxide (EtO), steam, hydrogen peroxide vapor, electron beam (E-beam), gamma irradiation, x-rays, or any combination of these sterilants.

The sterilization methods can be performed on the apparatus in question while the apparatus is partially or completely assembled (or partially or completely disassembled); thus, the methods can further comprise partially or completely assembling (or partially or completely disassembling) the apparatus before applying a dose of the selected sterilant(s). The sterilization methods can also optionally comprise applying one or more biological or chemical indicators to the apparatus before exposing the apparatus to the sterilant(s), and assessing mortality or reaction state of the indicator(s) after exposure. As a further option, the sterilization methods can involve monitoring relevant parameters in a sterilization chamber containing the apparatus, such as sterilant concentration, relative humidity, pressure, and/or apparatus temperature.

In view of the foregoing discussion of methods of sterilization, further embodiments comprise sterile apparatus. Sterile apparatus can comprise any of the apparatus disclosed herein that are intended for insertion into (or other contact with) the patient or that are intended for use at or near the surgical field during treatment of a patient. More specifically, any one or combination of the following can be provided as a sterile apparatus: the resistive element systems 10, 20 (with or without a working end of the types depicted in FIGS. 5-7A, 7C-7E, and 813B) and/or the catheters 11, 21 or sheath 22 thereof; the HAS treatment system 200 and/or the catheters 202, 202', 202" or introducer sheath 204 thereof; the datum devices 230, 250 (with or without a corresponding sheath 234/254 attached thereto); the HAS indexing treatment device 270 and/or the catheter 272, introducer hub 274 or outer sheath 277 thereof; the catheter shaft 290 with markings 292; the catheter 304 with detents 302; the HAS treatment system 310 and/or the catheter shaft 314 thereof; the HAS treatment system 330; the indexing devices 350, 360, 370, 390; the indexing system 430; the catheter handle 460.

While certain embodiments have been described, these embodiments have been presented by way of example only, and are not intended to limit the scope of the disclosure. Indeed, the novel methods and systems described herein may be embodied in a variety of other forms; furthermore, various omissions, substitutions and changes in the form of the methods and systems described herein may be made without departing from the spirit of the disclosure.

A number of applications, publications and external documents are incorporated by reference herein. Any conflict or contradiction between a statement in the bodily text of this specification and a statement in any of the incorporated documents is to be resolved in favor of the statement in the bodily text.

What is claimed is:

1. A method of preventing a heating coil of a treatment device from powering up outside anatomy of a biological entity, the method comprising:
   sensing a temperature on a heating coil of a blood vessel treatment device, the heating coil having at least one insulated layer configured to prevent electrical conduction into tissue of a blood vessel to be treated while at the same time allowing heat conduction into that same tissue of the blood vessel;
   determining whether said heating coil is disposed within the anatomy of the biological entity by determining whether said temperature satisfies a required initial temperature condition, the required initial temperature condition comprising a temperature that is significantly above an expected ambient room temperature;
   receiving a request to initiate power delivery to said heating coil of said blood vessel treatment device;
   if said temperature does not satisfy said required initial temperature condition, performing a safety procedure to interrupt a normal power-up process for the heating coil by preventing the heating coil of the treatment device from powering up outside the anatomy of the biological entity having the blood vessel to be treated.

2. The method of claim 1, further comprising: if said temperature satisfies said required initial temperature condition, allowing said normal power-up process for the heating coil.

3. The method of claim 1, wherein determining whether said temperature satisfies said required initial temperature condition, comprises determining whether said temperature has satisfied said required initial temperature condition at any time during a temperature sensing period.

4. The method of claim 3, wherein said temperature sensing period begins after connection of said treatment device to a power source.

5. The method of claim 4, wherein said temperature sensing period ends before delivery of therapeutic energy from said power source to said treatment device.

6. The method of claim 1 wherein said safety procedure comprises preventing the initiation of power delivery to said heating coil.

7. The method of claim 1, wherein said safety procedure comprises ceasing the delivery of power to said heating coil.

8. The method of claim 1, wherein said required initial temperature condition comprises that said temperature meet or exceed a minimum temperature.

9. The method of claim 8, wherein said minimum temperature is substantially at an expected internal temperature of the blood vessel to be treated with the treatment device.

10. The method of claim 8, wherein said minimum temperature is 5 to 10 degrees Celsius lower than the normal physiologic internal temperature of a blood vessel of the type normally treated with the treatment device.

11. The method of claim 1, wherein said required initial temperature condition comprises that said temperature fall within an acceptable temperature range.

12. The method of claim 11, wherein said temperature range brackets an expected internal temperature of the blood vessel to be treated with the treatment device.

13. The method of claim 11, wherein said temperature range brackets a temperature which is 5 to 10 degrees Celsius lower than the normal physiologic internal temperature of a blood vessel of the type normally treated with the treatment device.

14. The method of claim 1, further comprising, if said temperature does not satisfy said required initial temperature condition, providing a warning.

15. The method of claim 1, further comprising, if said temperature does not satisfy said required initial temperature condition:
- verifying that said heating coil is properly disposed with a blood vessel of a patient; and
- manually overriding said safety procedure and initiating a power-up process for the heating coil.

16. An apparatus for use in treating a blood vessel, the apparatus comprising:
- a heat application device adapted to receive power from a power source, the heat application device comprising a heating coil, the heating coil having at least one insulated layer configured to prevent electrical conduction into tissue of the blood vessel while at the same time allowing heat conduction into that same tissue of the blood vessel;
- a user interface adapted to receive a request from a user to initiate power delivery to said heating coil of said heat application device;
- a temperature measuring device configured to measure a temperature on said heating coil of said heat application device in order to determine whether said heating coil is disposed within anatomy of a biological entity having the blood vessel to be treated; and
- a module in communication with said temperature measuring device and said user interface, said module configured to determine whether a temperature measured by said temperature measuring device satisfies a required initial temperature condition and said module configured to follow a safety procedure if said temperature measured by said temperature measuring device does not satisfy said required initial temperature condition;
- said module further configured to follow the safety procedure to interrupt a normal power-up process for the heating coil of the heat application device if said temperature measured by said temperature measuring device does not satisfy said required initial temperature condition by preventing delivery of power to the heating coil of the heat application device, the required initial temperature condition comprising a temperature that is substantially at an expected internal temperature of the blood vessel, thereby preventing the heating coil of the heat application device from powering up outside the anatomy of the biological entity having the blood vessel to be treated.

17. The apparatus of claim 16, wherein said module is further configured to follow a normal power-up process for the heating coil if said temperature measured by said temperature measuring device satisfies said required initial temperature condition.

18. The apparatus of claim 16, wherein said module is further configured to determine whether said temperature has satisfied said required initial temperature condition at any time during a temperature sensing period.

19. The apparatus of claim 16, wherein said safety procedure comprises preventing the initiation of power delivery to said heating coil.

20. The apparatus of claim 16, wherein said safety procedure comprises ceasing the delivery of power to the heating coil.

21. The apparatus of claim 16, wherein said required initial temperature condition comprises that said temperature meet or exceed a minimum temperature.

22. The apparatus of claim 21, wherein said minimum temperature is above an expected ambient room temperature.

23. The apparatus of claim 21, wherein said minimum temperature is 5 to 10 degrees Celsius lower than the normal physiologic internal temperature of a blood vessel of the type normally treated with the treatment device.

24. The apparatus of claim 16, wherein said required initial temperature condition comprises that said temperature fall within an acceptable temperature range.

25. The apparatus of claim 16, wherein said temperature range is significantly above an expected ambient room temperature.

26. The apparatus of claim 16, wherein said temperature range brackets a temperature which is 5 to 10 degrees Celsius lower than the normal physiologic internal temperature of a blood vessel of the type normally treated with the treatment device.

27. The apparatus of claim 16, further comprising:
- a warning device in communication with said module; and
- wherein said module is further configured to cause said warning device to provide a warning if said temperature does not satisfy said required initial temperature condition.

28. The apparatus of claim 16, wherein said user interface is further adapted to receive a request from a user to manually override said safety procedure; and wherein said module is further configured to initiate a power-up process for said heating coil upon receiving a user request to manually override said safety procedure.

29. A method of preventing a heating element of a treatment device from powering up outside anatomy of a biological entity to be treated, the method comprising:
- providing power to the treatment device;
- sensing a temperature on the heating element of the treatment device, the heating element comprising electrical insulation configured to prevent electrical conduction into tissue while allowing heat conduction into tissue;
- determining whether said heating element is disposed within the anatomy of the biological entity to be treated by determining whether said temperature satisfies a required initial temperature condition, the required initial temperature condition comprising a temperature that is 5 to 10 degrees Celsius lower than a normal physiologic internal temperature of a hollow anatomical structure of the biological entity to be treated;
- receiving a request to initiate power delivery to the heating element of the treatment device;
- if said temperature does not satisfy the required initial temperature condition, preventing power delivery to the heating element, thereby improving safety by preventing the heating element from powering up outside the anatomy of the biological entity.

* * * * *